(12) United States Patent
Helm et al.

(10) Patent No.: US 12,076,507 B2
(45) Date of Patent: Sep. 3, 2024

(54) INTEGRATED SEALING AND SECURING DEVICE FOR VASCULAR CATHETERS AND METHODS FOR USE OF SAME

(71) Applicant: One IV Solutions, LLC, Dunnellon, FL (US)

(72) Inventors: Robert E. Helm, Rye Beach, NH (US); Karl Leinsing, Dover, NH (US); Joseph M. Durant, Derry, NH (US)

(73) Assignee: One IV Solutions, LLC, Dunnellon, FL (US)

( * ) Notice: Subject to any disclaimer, the term of this patent is extended or adjusted under 35 U.S.C. 154(b) by 314 days.

(21) Appl. No.: 16/234,790

(22) Filed: Dec. 28, 2018

(65) Prior Publication Data

US 2019/0247623 A1  Aug. 15, 2019

Related U.S. Application Data

(63) Continuation of application No. PCT/US2017/039797, filed on Jun. 28, 2017.
(Continued)

(51) Int. Cl.
*A61M 25/02* (2006.01)
*A61F 13/00* (2024.01)
(Continued)

(52) U.S. Cl.
CPC .......... *A61M 25/02* (2013.01); *A61F 13/023* (2013.01); *A61F 13/0243* (2013.01);
(Continued)

(58) Field of Classification Search
CPC ............ A61M 25/02; A61M 2025/024; A61M 2025/0266; A61M 2025/0246;
(Continued)

(56) References Cited

U.S. PATENT DOCUMENTS 9,468,740 B2 * 10/2016 Bierman ............... A61M 25/02
2006/0240208 A1 * 10/2006 Ishikawa .................. C09J 7/241
428/40.1

(Continued)

OTHER PUBLICATIONS

BD Nexiva Catheter.PDF—features and benefits of BD Nexiva catheter system. www.bd.com (Year: 2021).*

*Primary Examiner* — Caitlin A Carreiro
(74) *Attorney, Agent, or Firm* — Dorsey & Whitney LLP

(57) ABSTRACT

A device for sealing and securing a catheter at its insertion site in order to provide for optimum safe catheter function, and to achieve maximum catheter longevity/dwell time is described. The sterile seal achieved by this device fully protects the catheter and its insertion site from external contamination. The unique sterile seal also functions to fully stabilize and secure the catheter, thereby minimizing traumatic catheter injury and loss. A means of continuously viewing the insertion site is also provided, as well as mechanisms for maintaining sterility of the sterile chamber that is formed around the catheter insertion site by the integrated sealing and securing device. Together these features allow for improved catheter safety and function, and allow catheters to safely remain in place for an extended period of time. The need to change catheter dressings at intervals is minimized or eliminated.

16 Claims, 99 Drawing Sheets

Related U.S. Application Data

(60) Provisional application No. 62/355,701, filed on Jun. 28, 2016.

(51) Int. Cl.
*A61F 13/02* (2024.01)
*A61F 13/0246* (2024.01)
*A61M 5/158* (2006.01)

(52) U.S. Cl.
CPC ...... *A61F 13/0253* (2013.01); *A61F 13/0266* (2013.01); *A61F 2013/00412* (2013.01); *A61F 2013/00676* (2013.01); *A61F 2013/00846* (2013.01); *A61F 2013/00855* (2013.01); *A61F 2013/0091* (2013.01); *A61M 2005/1586* (2013.01); *A61M 2025/0246* (2013.01); *A61M 2025/0273* (2013.01); *A61M 2025/028* (2013.01)

(58) Field of Classification Search
CPC .... A61M 2025/0273; A61M 2025/028; A61M 2005/1586; A61F 13/02; A61F 13/06; A61F 13/26; A61F 13/023; A61F 13/0243; A61F 13/0253; A61F 13/0266; A61F 13/00; A61F 13/00021; A61F 13/0246; A61F 13/0259; A61F 2013/00412; A61F 2013/00676; A61F 2013/00855; A61F 2013/0091; A61F 15/008
USPC ...... 602/41, 54, 57; 604/180, 304, 307, 308; 128/887–888
See application file for complete search history.

(56) References Cited

U.S. PATENT DOCUMENTS

| | | | | |
|---|---|---|---|---|
| 2008/0200880 | A1* | 8/2008 | Kyvik | A61M 25/02 604/180 |
| 2010/0100049 | A1* | 4/2010 | Godfrey | A61M 25/02 604/180 |
| 2011/0152779 | A1* | 6/2011 | Panotopoulos | A61M 25/02 206/364 |
| 2012/0136314 | A1* | 5/2012 | Ciccone | A61M 25/02 604/174 |

* cited by examiner

INTEGRATED SEALING AND SECURING DEVICE FOR VASCULAR CATHETERS AND METHODS FOR USE OF SAME

PRIOR APPLICATIONS

This Application is a Continuation of Application PCT/US17/39797 filed on Jun. 28, 2017. Application PCT/US17/39797 claims the benefit of U.S. Provisional Application 62/355,701 filed on Jun. 28, 2016.

FIELD

The present invention relates to methods and devices for sterilely sealing and securing medical devices, and more particularly to methods and devices for placing a sterile sealed dressing around an inserted catheter.

BACKGROUND

Intravenous (IV) catheter therapy, since the introduction of first plastic IV catheters about 70 years ago, has played a central role in patient care. Currently, the placement of an IV catheter into a patient body (e.g., for the direct administration of fluids medications into the bloodstream) is among one of the most common invasive hospital procedure performed worldwide.

Presently, over 300 million peripheral IV catheters are sold in the United States every year. Further, about 60 to 90% of hospitalized patients in the U.S. can require an IV catheter during their hospital stay. It is, therefore, disconcerting that even the most rigorously performed studies indicate that the overall IV catheter failure rate lies between 35% and 50%. Catheter failures can take the form of phlebitis, infiltration, occlusion/mechanical failure, dislodgement, and/or infection. Any of such failures can lead to removal of the catheter prior to the end of its intended dwell time, or prior to the 72-96 hour dwell time limit traditionally specified by the Centers for Disease Control, The Infusion Nurses Society, and/or the Royal College of Nursing.

Peripheral IV catheter failures and related complications can be costly to the health care system. For example, the average cost of a short peripheral IV catheter insertion in the US can be between $28.00 and $35.00 for straightforward "first stick" insertions, although actual costs can vary considerably, depending on geographic and institutional factors, as well as the type of IV catheter inserted, and type and extent of supportive technology employed (e.g., dressing, needleless connector, extension tubing, dedicated stabilization device). That initial insertion cost, as well as the costs of identifying, removing, and re-inserting the failed IV catheter, is repeated each time that a failed catheter is replaced. Unfortunately, the failure of one peripheral IV catheter can initiate a negative cycle of catheter removal and re-insertion, as the risk of failure of each subsequent catheter is progressively increased. Venous depletion resulting from repeated failed catheters is an increasingly recognized entity, leading to the need for placement of more invasive, risky, costly venous access devices.

Costs associated with treating peripheral IV failure related complications and their sequelae (e.g., bleeding, hematoma formation, infusate extravasation, thrombophlebitis and catheter-related or bloodstream infection) can be additive to the basic costs of catheter removal and re-insertion. Caustic medication extravasation from a failed IV catheter can lead to extensive tissue necrosis, and result in having to repeat surgical debridement and reconstruction. A single case of catheter-related bloodstream infection (CRBSI) has been estimated to add 7-20 days to hospital length of stay, and up to $56,000 in additional cost, with total costs reaching up to 2.3 billion dollars in the U.S. intensive care units alone each year. The increase in multi-antibiotic resistant, so-called "super-bugs," such as methicillin-resistant *Staphylococcus aureus* (MRSA), vancomycin-resistant *Enterococcus* (VRE), and carbapenem-resistant Enterobacteriaceae (CRE) is particularly alarming, and has created the a serious potential for simple peripheral IV catheter surface contamination, in even otherwise healthy patients, to have lethal consequences. Of particular importance, the widespread use of IV catheters occurs in hospitals and other health care facilities, which are the same places where rapidly emerging "superbugs," such as VRE and CRE can be created and exist. The legal-malpractice implications alone are enormous, and can be expected to increase as health care system-acquired injury continues to enter the spotlight, and ceases to be tolerated from both a cost and societal viewpoint. Consequently, any potential source of infection, especially one leading directly to the bloodstream such as peripheral IV catheters, must be definitively addressed. Further, any source of iatrogenic patient injury, such as premature catheter failure, must be addressed.

Further, although often overlooked, peripheral IV catheter failure can be costly to the individual patients. However, such patient-perspective costs are often unquantified, unstudied, and underemphasized both clinically and in the literature. When a peripheral IV catheter fails, this failure has traditionally been accepted by caregivers and healthcare institutions as necessary additional work to be performed. However, such catheter failures can be more significant to an individual patient, who is already affected by the illness for which he/she is being treated. A failed IV catheter can result in pain, dissatisfaction, prolongation of care, and venous depletion-negativity that is compounded by the need to additionally treat minor and severe IV catheter failure related sequelae. Therefore, struggles with obtaining and maintaining peripheral IV access can often adversely impact a patient's overall hospital experience.

More recently, catheters can be allowed to stay in a patient's body beyond the traditional dwell time limit of about 72-96 hours. This so-called "clinically indicated re-site movement" allows well-functioning catheters (e.g., catheters not having any evidence of infection or other compromise) to remain in place beyond the traditional time limits. This approach can theoretically decrease the need for repeated IV access. However, because a large number of catheters can fail prior to the 72-96 hour limit, this concept currently has had limited impact in the clinical arena. Specifically, although effort can be expended to develop novel guidelines, such as clinically indicated re-site, that allow for well-functioning catheters to be left in longer can be developed, such efforts can be marginal if very few catheters have the capacity for safe long-term function.

Each time that an IV fails, a preferred insertion site is lost, and a less optimal site from a movement standpoint must be chosen. A negative viscous cycle of catheter re-insertion is initiated, as the risk of failure of each subsequent catheter is progressively increased. Venous depletion resulting from repeated failed catheters is an increasingly recognized entity, leading to the need for placement of more invasive, risky, costly venous access devices. As the population ages and hospital acuity increases, it will become imperative that peripheral IV care is optimized toward safe long-term functionality.

SUMMARY

In one aspect, some embodiments disclosed herein relate to a dressing for use with an implantable catheter. The dressing comprises a catheter securement plate configured to receive and hold a catheter. The catheter securement plate can have a plate adhesive disposed on at least a portion of its bottom surface to facilitate attachment to a patient's skin at a catheter insertion site. The dressing also comprises a protective sheet for covering the adhesive prior to deployment of the securement plate on a patient's skin and a cover configured for placement over the securement plate to define a sealed chamber at the catheter insertion site. The cover can also have a cover adhesive disposed on at least a portion of its bottom surface to contact the securement plate or the patient's skin to enclosed an implanted catheter.

In a related aspect, a medical dressing is disclosed. The medical dressing comprises a cover configured for placement over a catheter insertion site. The cover can have an cover adhesive disposed on at least a portion of its bottom surface to contact a catheter securement plate or the patient's skin to surround an implanted catheter. The cover can further have at least one aperture above the catheter insertion site. The medical dressing can also include a clear film configured to be placed on a top surface of the cover to define a sealed chamber at the catheter insertion site while also permitting viewing of the insertion site.

In other examples, any of the aspects above, or any system, method, apparatus described herein can include one or more of the following features.

The securement plate can further a slit configured to allow an length of catheter extension tubing to pass through. Additionally or alternatively, the securement plate can comprise a receptacle for an antiseptic configured receive an antiseptic for release into the chamber. The antiseptic can be chlorhexidine, isopropyl alcohol, or a combination thereof. Further, the securement plate can be adapted to receive a BD Nexiva™ catheter.

In some embodiments, the plate adhesive can comprise a double-sided adhesive tape. The adhesive tape can be a non-woven tape, such as silicone or hydrocolloid tape. Further, the clear film can be a breathable film.

Further, the cover can be configured to completely cover the securement plate. The cover can further comprise at least one window for viewing the catheter insertion site. The cover adhesive can be a hydrocolloid adhesive. Additionally or alternatively, the cover adhesive can be configured to remain adherent to a patient for about 3 to about 14 days. The cover can also be adapted to mate with a BD Nexiva™ catheter.

The medical dressing can further comprise a catheter securement clip that secures the implanted catheter or an extension tubing connected to the catheter. The securement clip can further comprise a sealing cap.

Other aspects and advantages of the invention can become apparent from the following drawings and description, all of which illustrate the principles of the invention, by way of example only.

BRIEF DESCRIPTION OF THE DRAWINGS

Features and advantages of the invention described herein, together with further advantages, may be better understood by referring to the following description taken in conjunction with the accompanying drawings. The drawings are not necessarily to scale, emphasis instead is generally placed upon illustrating the principles of the invention

FIGS. 1F-1N illustrate various example sterile dressings according to embodiments disclosed herein.

FIGS. 2A-2M illustrate various views of another embodiment of a catheter dressing according to some embodiments described herein.

FIGS. 2N-2AA illustrate the procedures for placing a dressing according to embodiments disclosed herein on an inserted catheter.

DETAILED DESCRIPTION

Figure 1A:
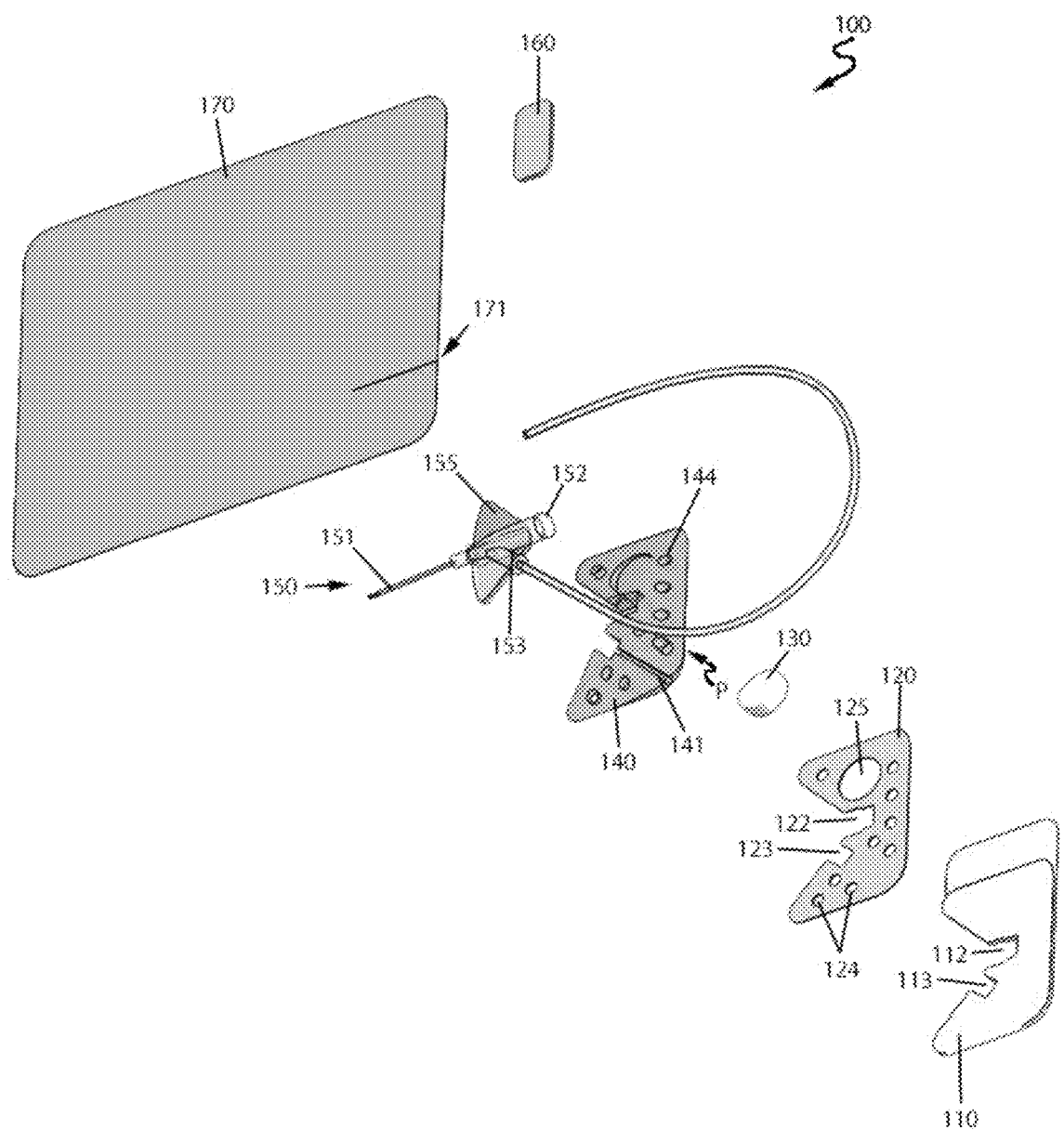
FIG. 1A illustrates an example of a sterile dressing for securing a catheter according to some embodiments disclosed herein.

Given the high incidences of infiltration, occlusion, and accidental removal of IV catheters (e.g., presently up to 90% of catheters can fail before therapy is complete), in order for clinically indicated re-site movement to be successful, a means of extending safe dwell time is needed. Further, since routine replacement of catheters is ineffective, interventions to reduce the complications associated with catheter removal are needed. Improved survival of intravenous catheters for even small increments of time can further reduce the number of insertions, staff workloads, and costs. Such improvement can be accomplished by improving the manner in which IV catheters are inserted, secured, or flushed.

Securement can be an important factor in extending the safe dwell time of a catheter because without some form of securement (e.g., by tape, adhesive dressing, or a combination of the two) all peripheral IV catheters can quickly fall out. Cloth tapes have been traditionally used as the primary securement means, with operators using highly variable ways of placing non-sterile adhesive tape securement patterns. Initially combined with gauze dressings, the gauze and tape dressing remains one of the two forms of peripheral IV catheter dressings sanctioned by the CDC. Most clinicians are familiar with the various taping patterns that have been developed, with specifically torn non-sterile tape pieces placed in specified patterns (e.g., u-shape) to adhere the catheter hub to the skin around the insertion site. These taping patterns necessarily introduce contaminants to the immediate hub and insertion site, as these nonsterile tape strips are applied using non-sterile gloves in a non-sterile field.

More recently, the gauze and tape dressing have largely been supplanted by adhesive film type dressings (e.g., 3M Tegaderm®), with supplemental non-sterile tape still applied in various supportive fashions to help secure the catheter into the desired position. Both forms of peripheral IV catheter dressings have the common drawback of being "patch-type" dressings, acting by pressing the catheter hub (which is non-sterile as it has been grasped by non-sterile gloves) against the skin to effect securement, with only a portion of the circumference of the hub actually exposed to the stabilizing adhesive. The adhesive film dressing can be tented up by the round catheter hub, leaving channels beneath the dressing on either side of the hub that lead directly to the catheter insertion site. Over time, movement of the partially secured hub can serve to loosen the adhesive dressing, further increasing the channel size and decreasing the amount of catheter securement and stabilization. This can lead to increased external catheter and insertion site contamination, and increased traumatic catheter injury and loss.

As stated, many existing and sanctioned (CDC, INS, etc.) vascular catheter dressings rely on the simple Band-Aid® type covering mechanism, which can act by simply covering the catheter and its insertion site and pressing the catheter against the skin. However, use of the simple patch-type dressing appears to be directly related to the high rate of IV catheter failure, due to the inability of the dressing to prevent or eliminate the two main underlying causes of IV catheter failure: (1) catheter-related trauma, and (2) external catheter and catheter insertion site contamination.

Traumatic forces applied to IV catheters can also, directly and indirectly, lead to catheter failure. These forces can cause direct inadvertent full dislodgement of the catheter from the patient, or they can cause acute or chronic movement of the catheter that leads to injury of the blood vessel wall and/or surrounding soft tissues. Further, "pistoning" of the catheter-movement of the catheter and its tip inside the vessel wall, can be an important cause of IV catheter failure.

Catheter stabilization and securement can also be important for decreasing traumatic catheter failure and increasing safe catheter dwell time. As discussed, traditional CDC sanctioned tape and gauze or tape and adhesive film catheter dressings can only provide partial and highly variable securement of the catheter. Variability can be attributable, for example, to the large number of taping patterns available, and to the innate flexibility of tape securement that still allows movement of the catheter. While additional adhesive securement can be provided by the adhesive film dressing that is placed over the taped hub, this can provide only marginal additional securement benefit as only a portion of the circumference of the catheter hub is actually contacted. The remainder of the circumference of the hub can be either pressed against the skin (posterior aspect of the hub) of left open to air (lateral aspect of the hub with tented up dressing). Any movement of the catheter hub can serve to progressively detach and decrease this limited adhesive surface area.

Additionally, because of the general tapering (e.g., conical or step-wise decrease in diameter) shape of all existing catheter hubs, there is no mechanical anchor or stop-point on the hub to prevent outward migration, once adhesion is lessened or lost. The progressively narrowing conical shape of the catheter hub can provide for an actual mechanical disadvantage; any movement or moisture-related loss of adhesion allows for outward hub movement, bringing a smaller diameter hub segment into the initial adhesive securement point. Once the hub begins outward migration, there is no anchor point to hold the catheter in position, and this can ultimately lead to dislodgement and loss of the catheter.

A number of compensatory measures have been developed and applied to improve catheter securement. For example, in order to minimize direct movement and manipulation of the catheter during clinical use, it is now common to attach a segment of extension tubing "j-loop" to the catheter hub. A needle or needleless connector attached to this j-loop can become the (remote) working end of the catheter. Additional tape can then be applied to secure the extension tubing-connector complex-IV catheter complex, typically resulting in a large bulky catheter-tubing-connector dressing-tape complex, with an extensive uncomfortable adhesive surface area (which can cause discomfort e.g., by sticking of tape to body hair). The size, complexity, and protuberance of this complex can predispose the complex to catch on clothing or surrounding structures, particularly the often exposed tubing j-loop, which is often prone to being hooked and pulled with mechanical advantage.

However, the use of extension tubing can decrease the incidence of inadvertent catheter dislodgement over time. Loops extending outward from the dorsum of the hand can be at highest risk for dislodgement. IV catheters with integrated extension tubing side arms have become available (e.g., the BD Nexiva™ catheter). These catheters can decrease the clinical complexity and number of steps needed to attach an add-on extension tubing segment at the time of insertion. While these catheters have improved the previous simple non-integrated catheter technology, the primary problem of inadequate sealing at the extension tube exit site at the periphery of the dressing persists. Non-sealing channels on either side of the tented up dressing (that lead directly to the catheter-skin insertion site) continue to remain present. These channels increase the potential for catheter insertion site contamination over time, and decrease the ability for the patient to be exposed to water (e.g., bathing or showering) and can significantly compromise the patient's hygiene.

Dedicated securement devices, such as Bard's StatLock® device, have shown significant benefit in improving catheter longevity, with a direct effect on reducing overt catheter dislodgement and traumatic blood vessel and soft tissue injury rates, as evidenced by decreased failure rates (including dislodgement, infiltration, phlebitis). Those devices, however, also add bulk to the catheter-dressing complex, extend adhesive surface area, and act to tent the dressing upward, further allowing outside contamination. They also increase the moist dead-space area/volume beneath the dressing space that is directly and indirectly connected to the catheter skin insertion site. Dedicated stabilization devices (e.g., StatLock®) can also add significant cost and complexity to peripheral IV catheter care.

Catheter stabilization continues to be a central issue in efforts to improve IV catheter outcomes, and several dedicated stabilization products (e.g., StatLock®) have been clinically introduced. Increased catheter stabilization with these dedicated stabilization device has shown clear benefit in several prospective trials. In fact, the benefit of catheter stabilization is now reflected in the 2011 INS Standards, which requires considering the use of a catheter stabilization device as the preferred alternative to tape or sutures, when feasible.

Catheter contamination and infection can also cause IV catheter failure. While the rate of overt bloodstream infection that can be directly linked to peripheral IV catheters is relatively low in the literature, this rate is likely underreported. The rates of sub-bloodstream infection are significantly higher, and lead to premature catheter failure through a variety of end mechanisms including phlebitis, infiltration, extravasation, pain, and thrombotic occlusion. For example, a single case of catheter-related bloodstream infection (CRBSI) has been estimated to add 7-20 days to hospital length of stay, and up to $56,000 in additional cost with total costs reaching up to 2.3 billion dollars in U.S. intensive care units alone each year. The increase in multi-antibiotic resistant "super-bugs," such as methicillin-resistant *Staphylococcus aureus* (MRSA), vancomycin-resistant *Enterococcus* (VRE), and carbapenem-resistant Enterobacteriaceae (CRE) is particularly alarming, and has created the very real potential for simple peripheral IV catheter surface contamination, in even otherwise healthy patients, to have lethal consequences. Further, since IV catheters are often used in the same environment (e.g., hospitals and other health care facilities) as where rapidly emerging "superbugs," such as VRE and CRE are created, catheter failures caused by catheter contamination and infection can result in potential legal-malpractice implications for facilities at which the catheters are employed.

Clearly a dressing strategy that allows direct penetration of bacterial and other pathogens to the catheter skin insertion site is inadequate in today's era of multi-resistant superbugs. The fact that access to the insertion site can increase over time, as the overlying patch-type dressing loosens with clinical use and patient activity, only compounds the problem. Acting in a viscous negative cycle with movement related trauma, catheter contamination allowed by existing dressing care leads to not only premature catheter failure, but to unsafe treatment of hospitalized patients day after day. Further, the fact that an increasing number of patients are being treated in an outpatient setting, and return to their normal activities such as bathing and showering, only increases the need to move toward dressing technology that not only seals and protects the catheter form outside contamination, but that also fully secures and stabilizes the catheter against traumatic injury and loss.

Some embodiments described in the present disclosure relate to an improved integrated sterile sealing and securing dressing that can be used with a vast variety of IV catheters. The dressing can achieve a durable sterile seal that can, in turn, serve to fully stabilize and secure an inserted catheter, lead to longer safe dwell time, and simplify and improve the functions of the catheter. The dressing can be designed to seal and secure all existing catheters, including those with a built-in extension tubing side arm.

In one aspect, a single-piece (one-piece) integrated sterile dressing is described. The dressing can include various features such as (1) a main adhesive pad composed of hydrocolloid or other adhesive compatible with the desired durable adhesion to the patient's skin, (2) a clear/transparent breathable insertion site viewing window, (3) a form fitting portion of the dressing itself (or a separate body fused/attached to the underside of the dressing) that mates in stabilizing and securing fashion with the hub contour of the inserted catheter, (4) a sealing flange that durably circumferentially seals around the portion of the catheter hub exiting the dressing (in the case of a BD Nexiva™ catheter this can correspond to the extension tubing side-arm), (5) an ancillary support device to optimize the integrity of the seal provided for by the sealing flange, (6) a means for maintaining or re-establishing/propagating sterility of the sealed sterile insertion site viewing chamber, and (7) a separate secondary/ancillary device for stabilizing the segment of extension tubing that has exited the device such that disruptive forces exerted upon and by this extension tubing are minimized In another related aspect, a two-piece dressing that utilizes a catheter securement plate having a plate adhesive is disclosed. The catheter securement plate can achieve a seal around a portion of the catheter that exits the catheter (e.g., the extension tubing side-arm of a BD Nexiva™ catheter) to fully stabilize and durably seal the inserted catheter. The dressing can also include an anti-microbial agent configured to aid in maintaining sterility of the sealed viewing chamber over time. The dressing can also utilize a secondary and/or ancillary extension tubing stabilization device.

In yet another related aspect, a hybrid combination dressing is described. The dressing can have a central body that mates to specific features of an inserted catheter hub. The central body can be integrally fused and/or formed with a main adhesive plate to form a one piece device. This hybrid dressing can be applied in a similar fashion as the one-piece dressing described above. The dressing can also have similar sealing and securing support characteristics, as well as antimicrobial support capabilities. In another related aspect, a one-piece folding dressing that achieves the same desired result as the one-piece and the two piece dressings (described above) is disclosed.

Further, the catheters described herein can utilize a sticky dot sheeting (described in more details below) that can further secure the catheter to a patient's skin at an insertion site.

A dressing according to some embodiments disclosed herein can provide a sterile means for sealing and securing a catheter system. FIG. 1A is an example of a sterile dressing 100 according to some illustrative embodiment disclosed herein. The sterile dressing 100 can be used to seal and secure a catheter system 150. The catheter system 150 can be any suitable catheter system 150 known and available in the art. For example, the catheter system 150 can be BD Nexiva™ catheter system 150. The catheter system 150 can include a catheter 151 having a side arm 153 with an extension tubing 154. The catheter system 150 can also include one or more stabilization wings 155 and a back arm 152 that are coupled to the catheter 151. A flexible tube seal and securement member 140 (e.g., catheter securement plate) can be configured to receive and mate with the catheter system 150. The tube seal and securement member 140 can be made from any appropriate materials available in the art. For example, the tube seal and securement member 140 can be made from materials such as silicone rubber and polyurethane.

Figure 1B:
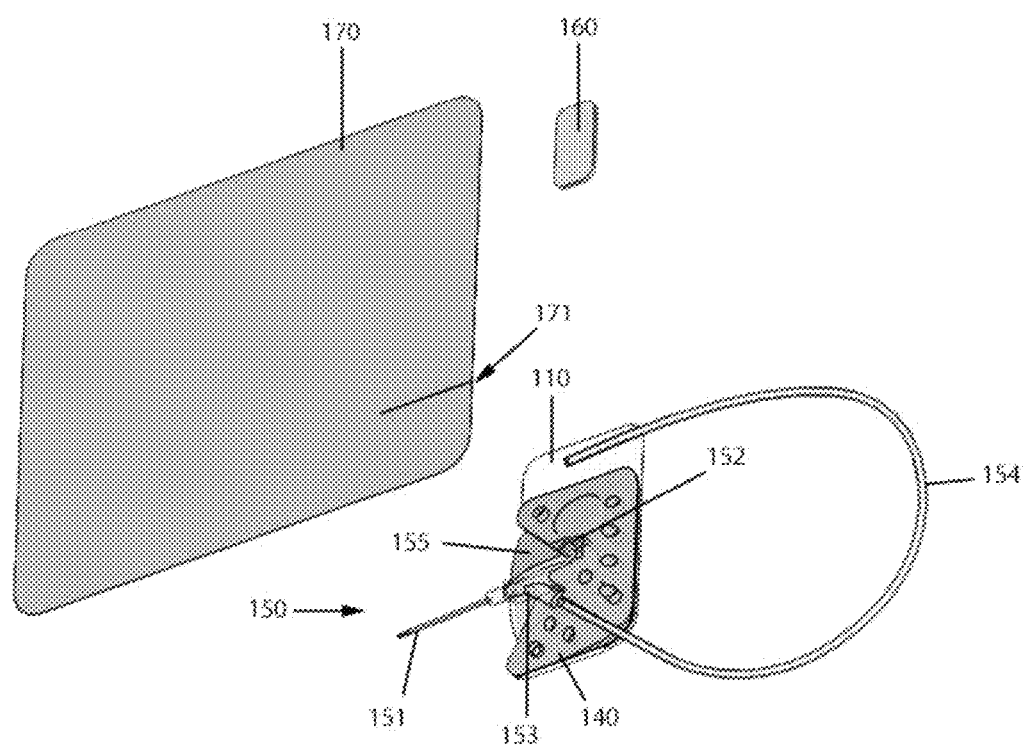
FIG. 1B is another example of a sterile dressing for securing a catheter according to some embodiments disclosed herein.
Figure 1C:
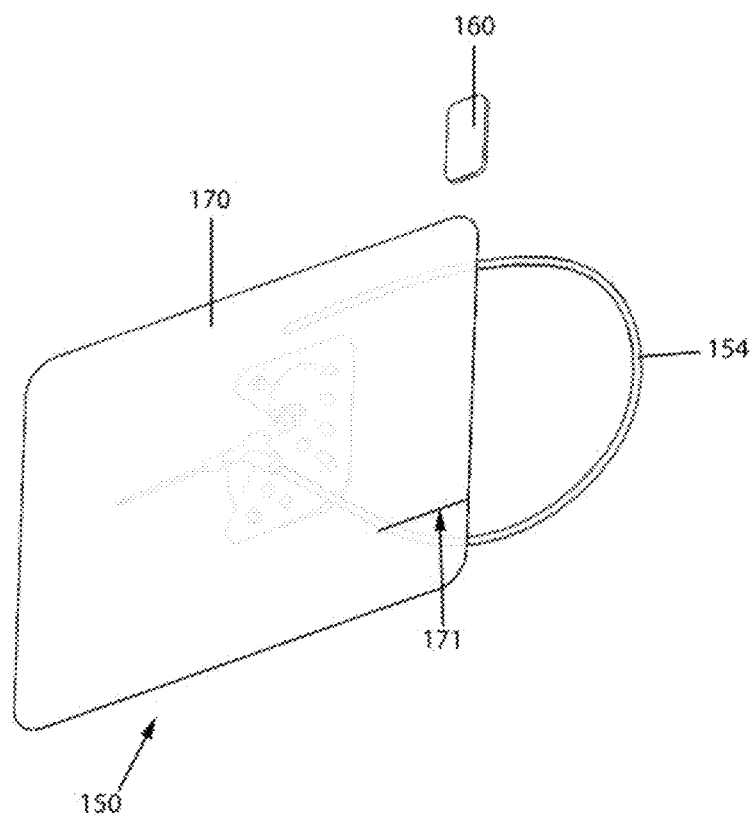
FIG. 1C is yet another example of a sterile dressing for securing a catheter according to some embodiments disclosed herein.
Figure 1D:
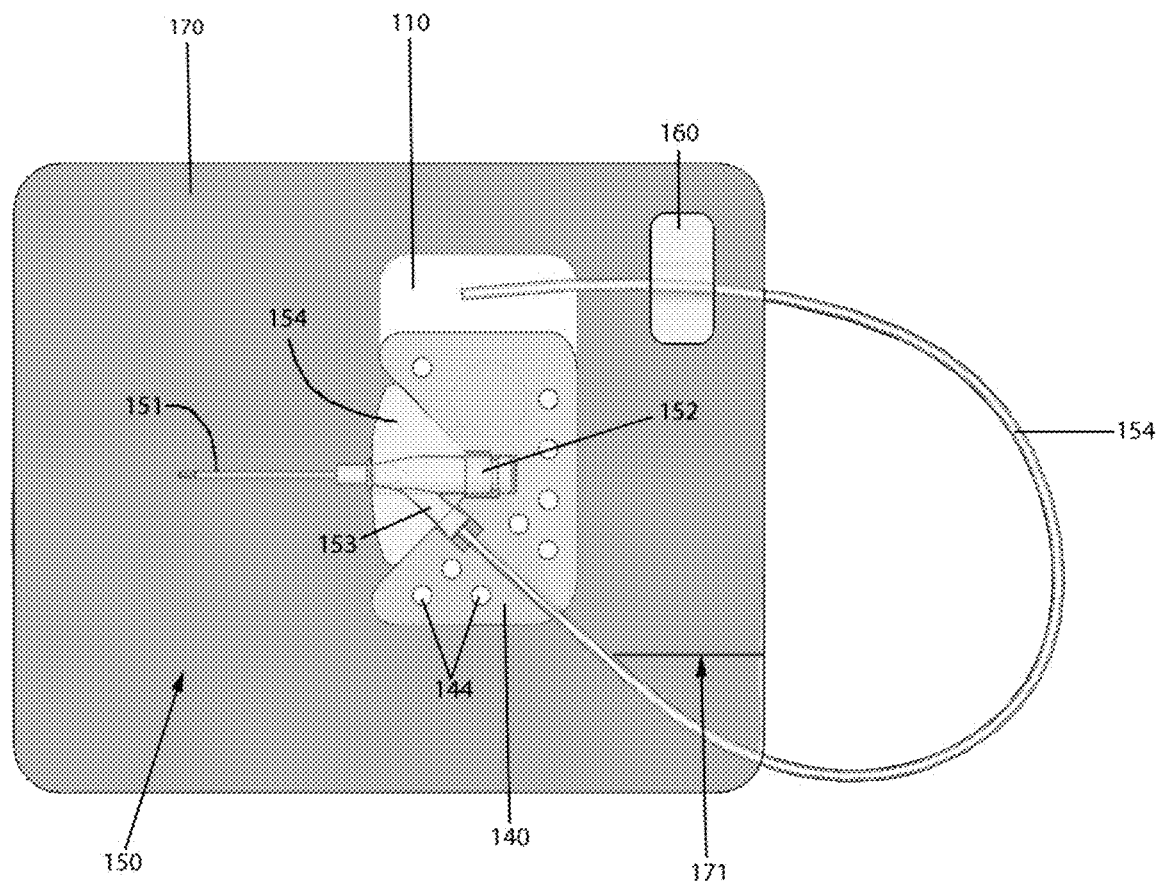
FIG. 1D is yet another example of a sterile dressing for securing a catheter according to some embodiments disclosed herein.
Figure 1E:
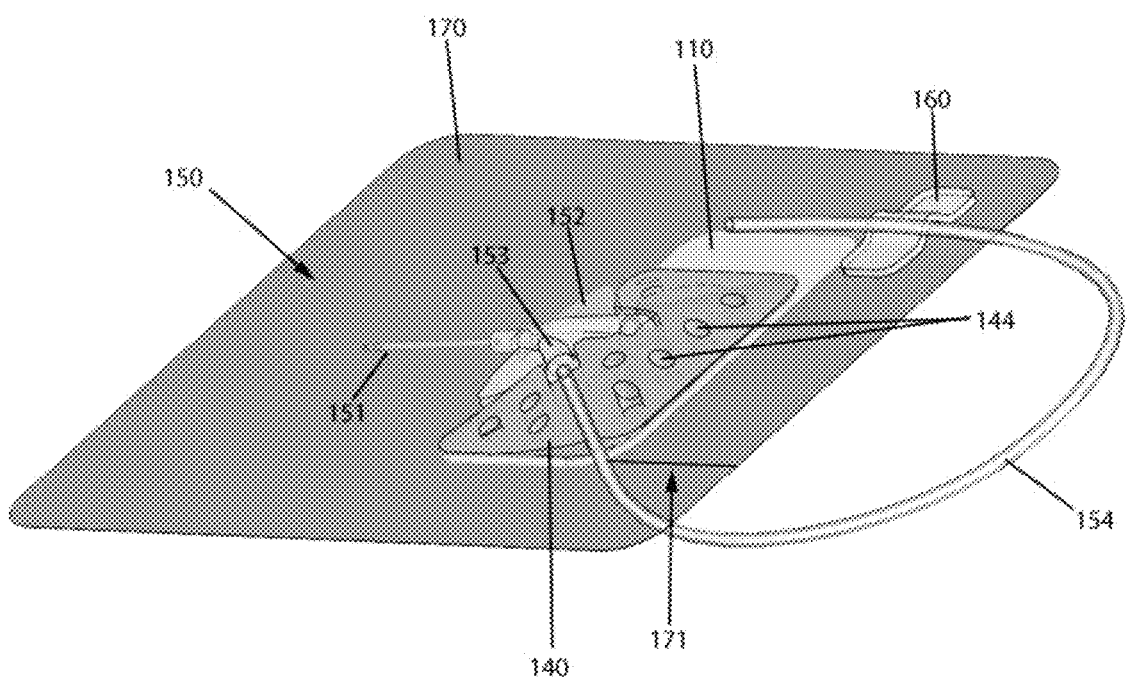
FIG. 1E is yet another example of a sterile dressing for securing a catheter according to some embodiments disclosed herein.
Figure 1F:
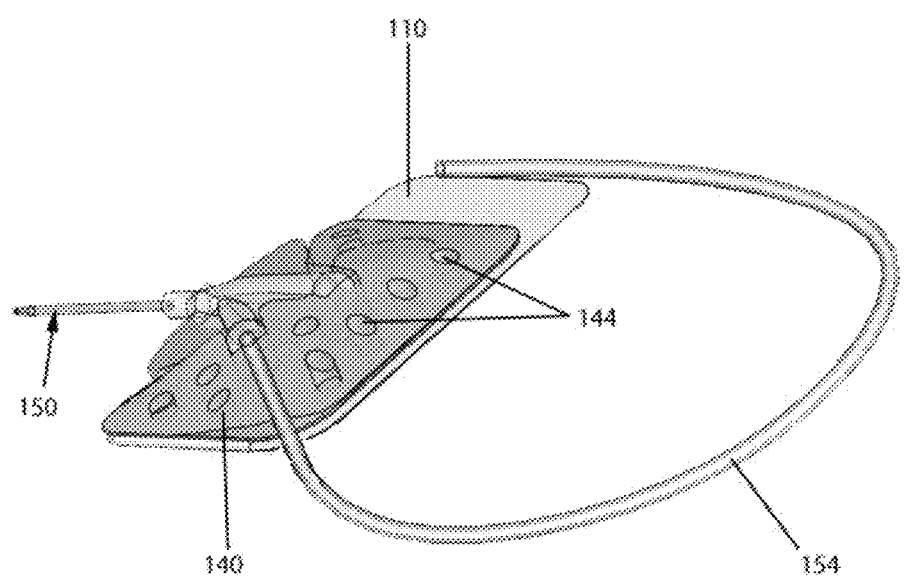
Figure 1G:
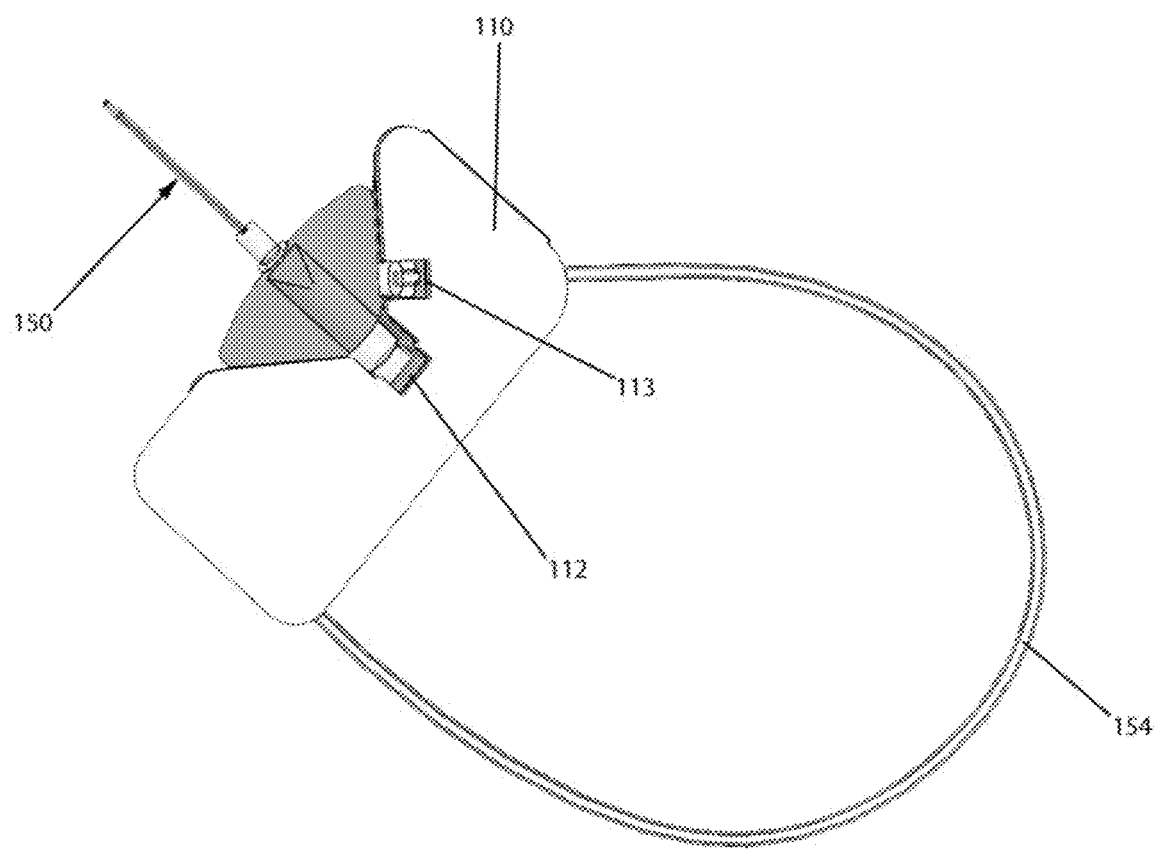
Figure 1H:
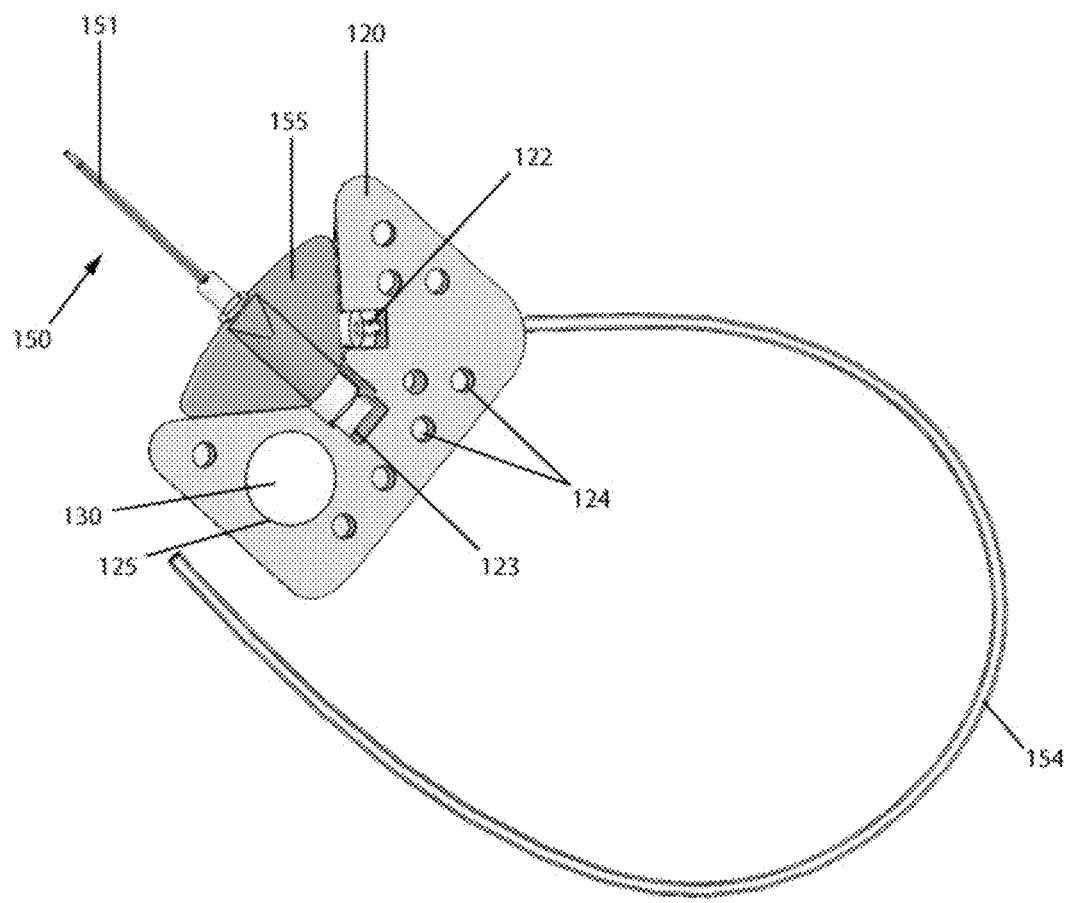
Figure 1J:
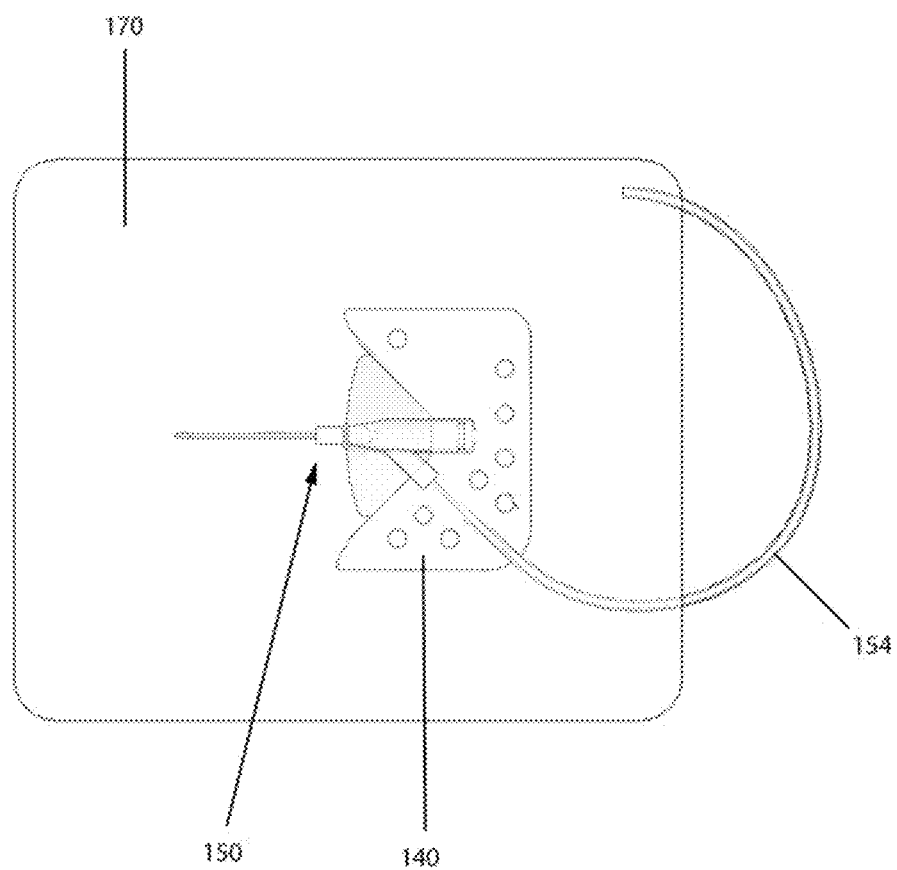
Figure 1K:
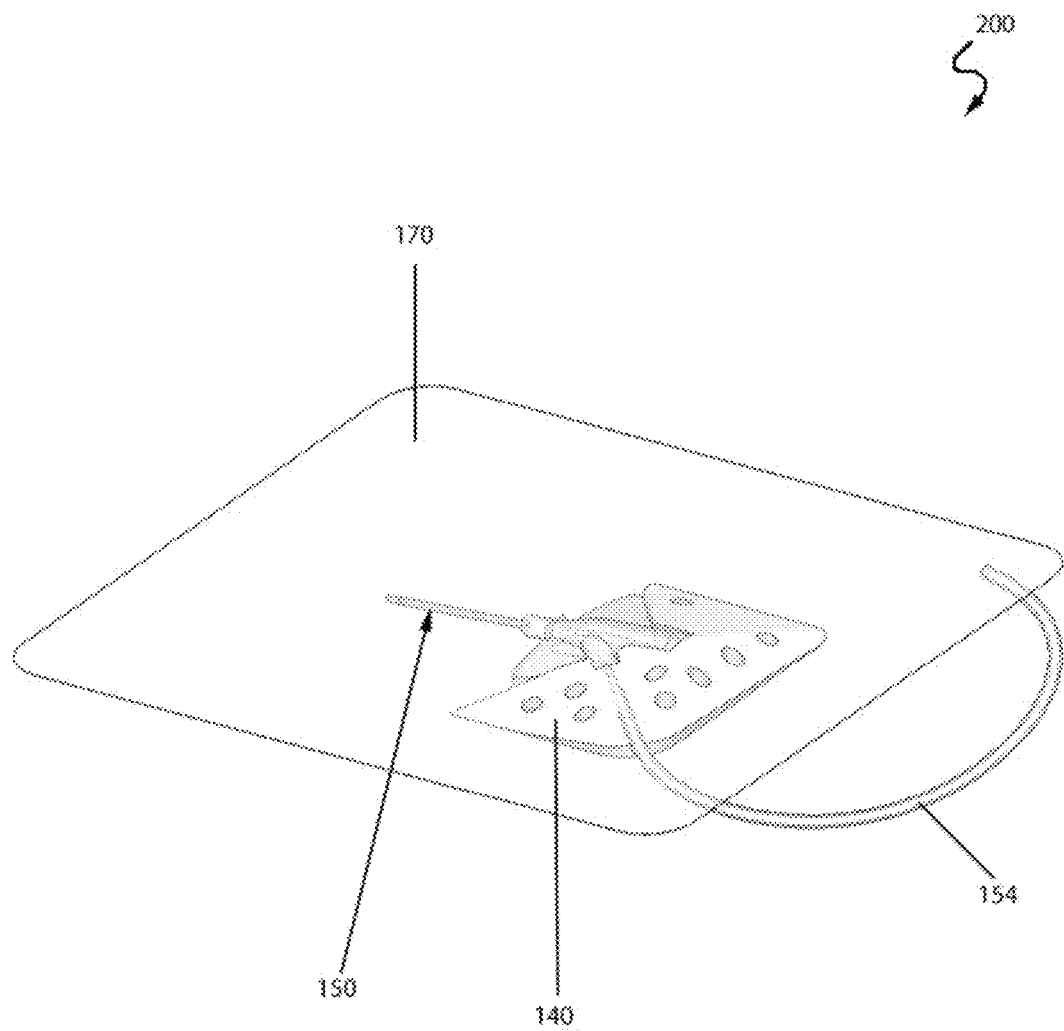
Figure 1L:
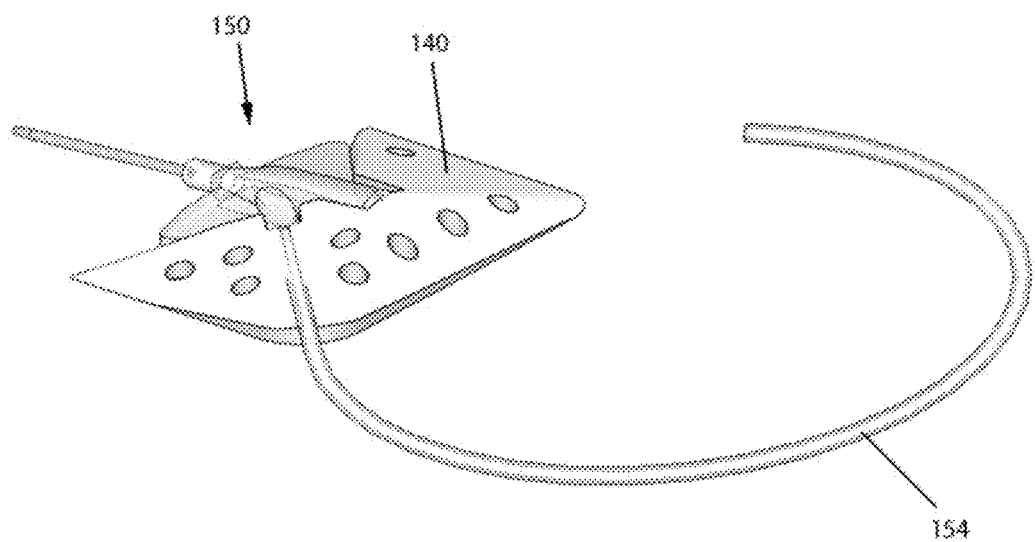
Figure 1M:
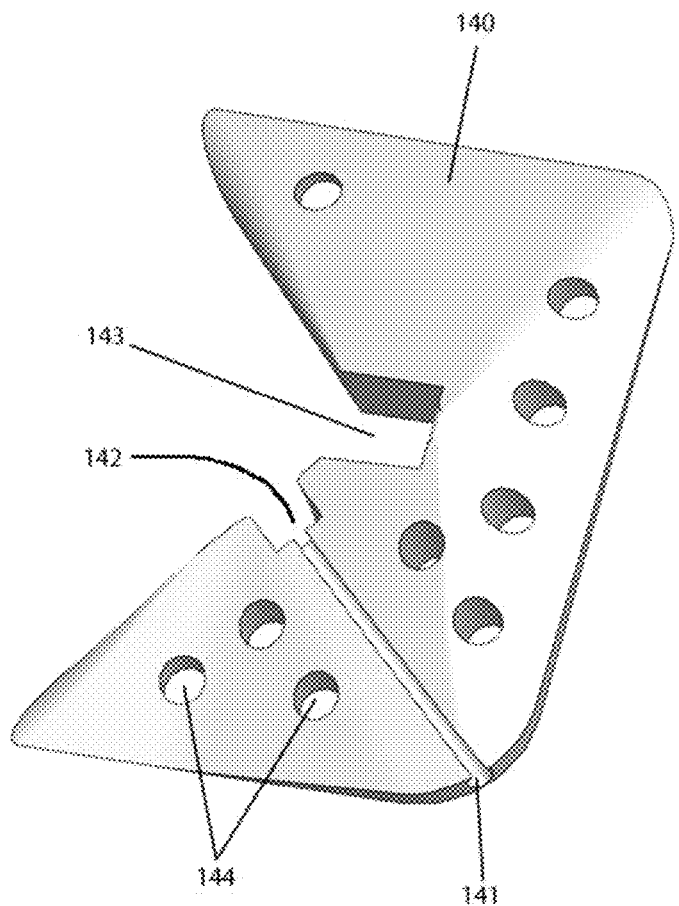

The tube seal and securement member 140 can include one or more tubing channels 141 (shown in FIG. 1M). The tubing channel 141 can be configured to receive and secure at least a portion of the extension tubing 154 of the catheter system 150. The tube seal and securement member 140 can also include one or more holes 144 on one or more sides of the tube seal and securement member 140. The holes 144 can be configured to allow for greater breathability of the dressing 100. The tube seal and securement member 140 can further include one or more slots 142, 143 (shown in FIG. 1I). The slots 142 and 143 of the tube seal and securement member 140 can be configured to receive the side arm 153 and/or the back arm 152 of the catheter system 150.

Figure 1N:
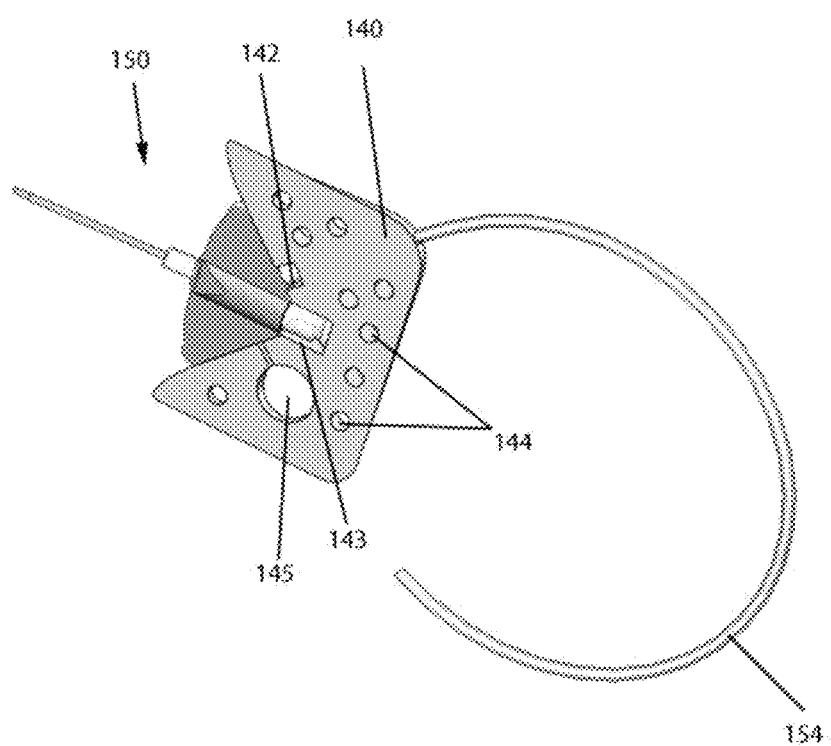

The tube seal and securement member 140 can also include one or more recess regions 125 (shown in FIG. 1N). Each recess 125 can be configured to receive one or more suitable material. For example, each recess 125 can be configured to receive an antiseptic sponge sac or gel 130. The material included in the recess 125 can be any suitable material available in the art. For example, an antiseptic sac or gel 130, such chlorhexidine (CHG) and/or isopropyl alcohol (IPA) can be employed.

The sterile dressing 100 can also include an adhesive, such as a double sided adhesive tape 120 (e.g., plate adhesive). The adhesive 120 can be applied to a bottom side (e.g., the side (P) facing the patient's skin) of tube seal and securement device 140. The adhesive tape 120 can be made from any suitable material available in the art. For example, the adhesive tape 120 can be a non-woven tape. Further, the adhesive tape 120 can generally have any suitable size or shape available in the art. For example, in some embodiments, the adhesive tape 120 can generally have similar and/or same dimensions as the tube seal and securement member 140.

The adhesive tape 120 can have one or more slots 122, 123 that are configured to correspond to the slots 142 and 143 of the tube seal and securement member 140. Further, the adhesive tape 120 can include one or more holes 124 that are configured to substantially line up with the holes 144 of the tube seal and securement member 140. The adhesive tape 120 can be made from any suitable material in the art. For example, the adhesive tape 120 can be made from silicone and/or hydrocolloid.

A peel-back protective paper 110 (i.e., protective sheet) can be utilized to cover the adhesive tape 120 until the dressing 100 is ready to be used. As shown in FIG. 1, the peel-back protective paper 110 can generally have similar and/or same dimensions as the adhesive tape 120. Further, the peel-back protective paper 110 can have one or more slots 112, 113 that are configured to correspond to the slots 122, 123 of the adhesive tape 120.

The dressing 100 can further comprise a film 170. The film 170 can be configured to secure the catheter 150 in place. The film 170 can be sterile film that sterilely secures the catheter 150 in place. The film 170 can comprise an adhesive to sterilely secure catheter 150 in place. Generally, the film 170 can be made from any suitable material available in the relevant art. In some embodiments, the film 170 can be clear to allow for visual monitoring of the catheter system 150 and the insertion site (not shown). Further, in certain embodiments, the film 170 can be breathable. The film 170 can further be coupled to an adhesive tape 160 and include a slit 171. The slit 171 can be used to pass at least a portion of the extension tubing 154 for underneath the film 170 (surface adjacent to the patient's skin) to over the film 170 (the exposed surface of the film 170). The adhesive tape 160 can be configured to secure the extension tubing 154 to the film 170. The adhesive tape 160 can be made from any suitable material known in the art.

FIG. 1B is another example of a sterile dressing for securing a catheter according to some embodiments disclosed herein. In this example, the peel-back protective paper 110 is shown as being attached to the tube seal and securement member 140. As shown, at least a portion of the extension tubing 154 can also attach to the peel-back protective paper 110 to further secure the catheter in place.

FIG. 1C is yet another example of a sterile dressing for securing a catheter according to some embodiments disclosed herein. In this example, the film 170 is shown as covering the catheter system 150 and the remaining parts of the dressing 100. As noted, the film 170 can be transparent to allow visual evaluation of the insertion site. Further, as shown in FIG. 1C, at least a portion of the extension tubing 154 can remain exposed after the film 170 has been placed on the catheter system 150 and the remaining portions of the dressing 100. The adhesive tape 160 can also be used to secure the film 170 to the insertion site.

FIG. 1D is yet another example of a sterile dressing for securing a catheter according to some embodiments disclosed herein. FIG. 1D illustrates the components that are placed under the film 170. As shown in FIG. 1D, the adhesive tape 160 can be used to secure at least a portion of the extension tubing 154 to the film 170 (e.g., on the side of the film 170 that would come in contact with the patient's skin (not shown) or on the exposed side of the film 170).

FIG. 1E is yet another example of a sterile dressing for securing a catheter according to some embodiments disclosed herein. As shown in FIG. 1E, the slots 142 and 143 of the tube seal and securement member 140 can be configured to receive the side arm 153 and/or the back arm 152 of the catheter system 150.

FIGS. 1F-1N illustrate various example sterile dressings according to embodiments disclosed herein. Specifically, FIG. 1F illustrates the peel-back protective paper 110 after attachment to the adhesive tape 120 and the tube seal and securement member 140. As shown in FIG. 1G, the peel-back protective paper 110 can have the same/similar shape and size as the adhesive tape 120 and/or the tube seal and securement member 140. Further, the peel-back protective paper 110 can have one or more slots 112, 113 that are configured to correspond to the slots 122, 123 of the adhesive tape 120.

FIG. 1H illustrates the adhesive tape 120 with respect to the catheter system 150. As shown, the adhesive tape 120 can have one or more slots 122, 123 that are configured to correspond to the slots 142 and 143 of the tube seal and securement member 140. The slots 142 and 143 of the tube seal and securement member 140 can be configured to receive the side arm 153 and/or the back arm 152 of the catheter system 150. Further, the tube seal and securement member 140 can also include one or more recess regions 125 configured to receive a material, such as an antiseptic sponge sac or gel 130.

FIG. 1I illustrates the tube seal and securement member 140 as positioned on the adhesive tape 120 and the peel-back protective paper 110. As shown, the tube seal and securement member 140 can include one or more tubing channel 141 can be configured to receive and secure at least a portion of the extension tubing 154 of the catheter system 150. FIG. 1J illustrates a portion of the extension tubing 154 of the catheter system 150 as disposed and secured within the tubing channel 141. FIG. 1J and FIG. 1K also illustrate the dressing 100 and the catheter system 150 as secured in by the sterile transparent film 170. FIG. 1L also illustrates that at least a portion of the extension tubing 154 of the catheter system 150 can be secured by a tubing channel 141 of the tube seal and securement member 140.

Further, as shown in FIG. 1M, the tube seal and securement member 140 can also include one or more holes 144 on one or more sides of the tube seal and securement member 140. The holes 144 can be configured to allow for greater breathability of the dressing 100. As shown in FIG. 1H, the adhesive tape 120 can include one or more holes 124 that are configured to substantially line up with the holes 144 of the tube seal and securement member 140. Further, as shown in FIGS. 1M-1N, the slots 142 and 143 of the tube seal and securement member 140 can be configured to receive the side arm 153 and/or the back arm 152 of the catheter system 150. FIG. 1N also illustrates that the tube seal and securement member 140 can include one or more recess regions 145 configured to receive a material, such as an antiseptic sponge sac or gel 130. These recess regions 145 can be arranged such that they correspond to and/or line up with one or more recess regions 125 of the adhesive tape 120.

Figure 2A:
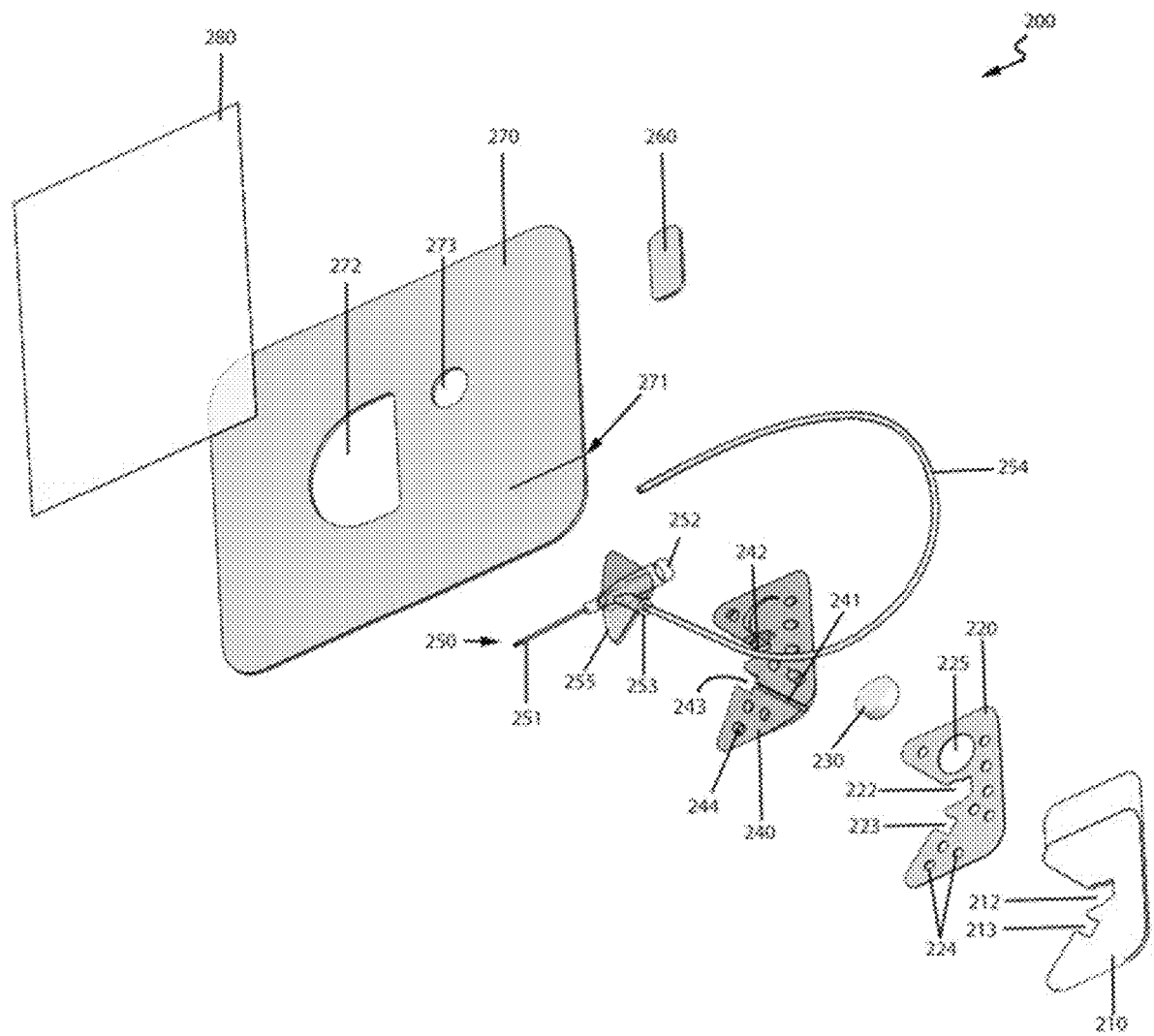
Figure 2B:
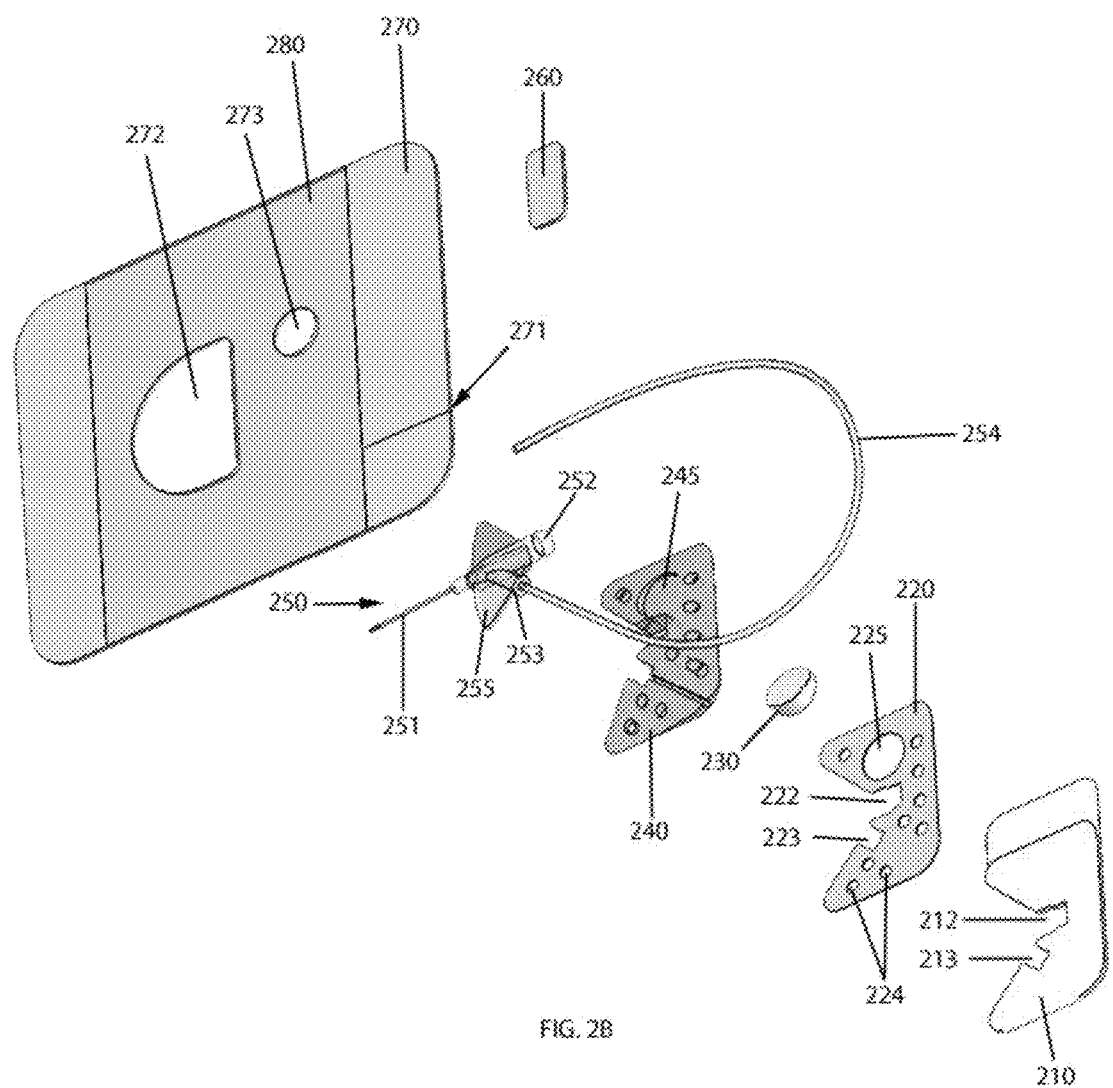
Figure 2C:
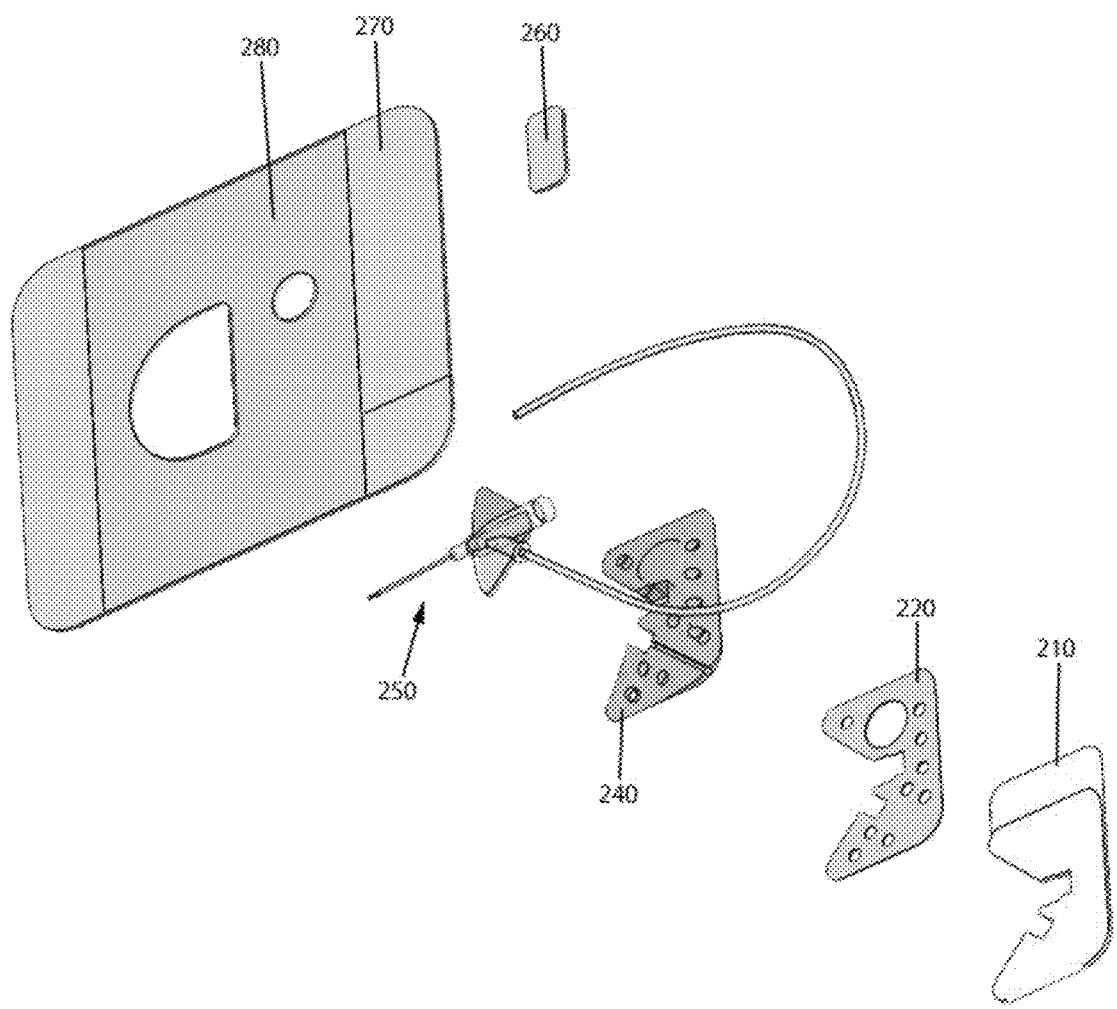
Figure 2D:
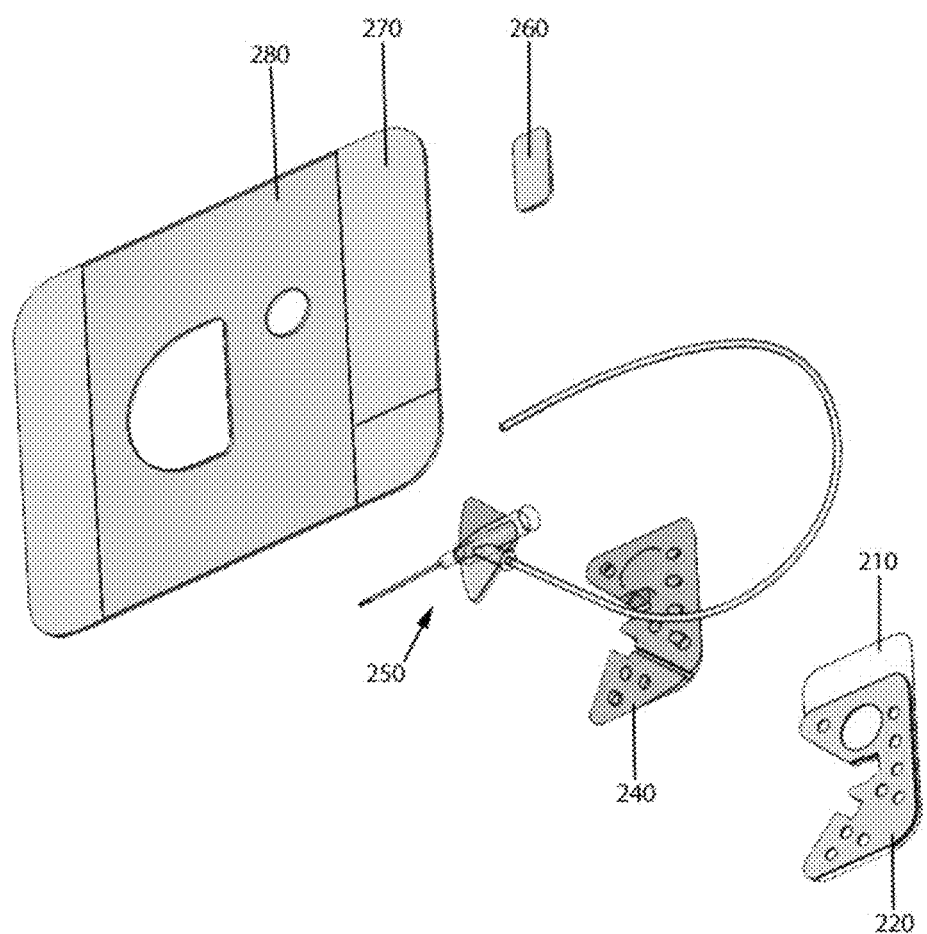
Figure 2E:
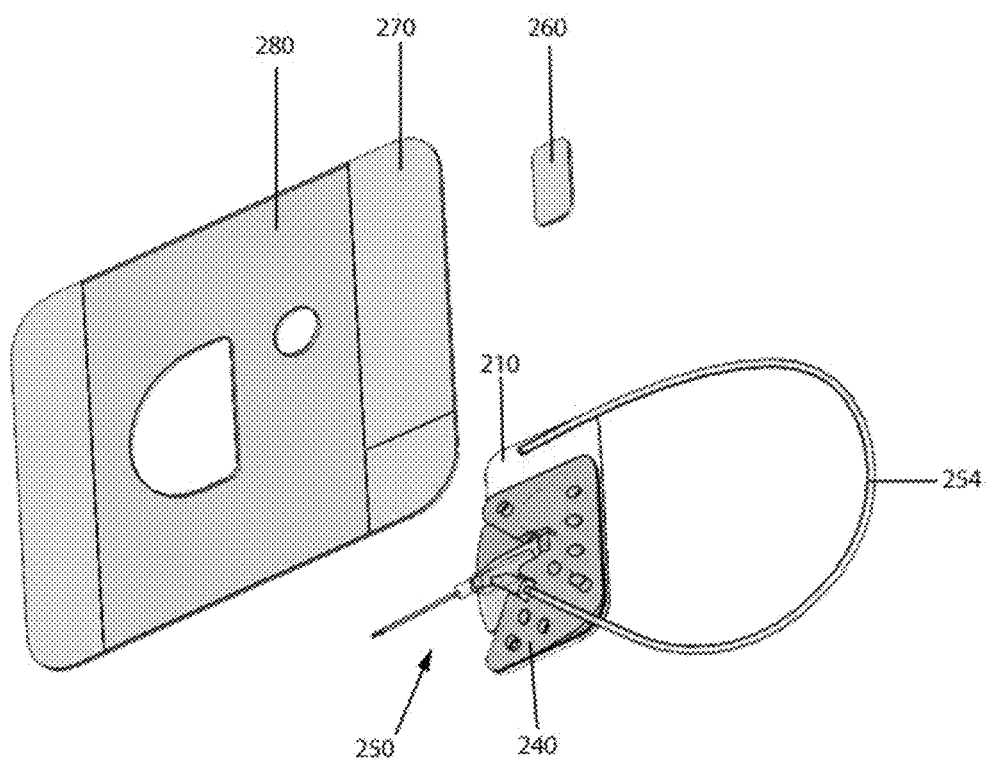
Figure 2F:
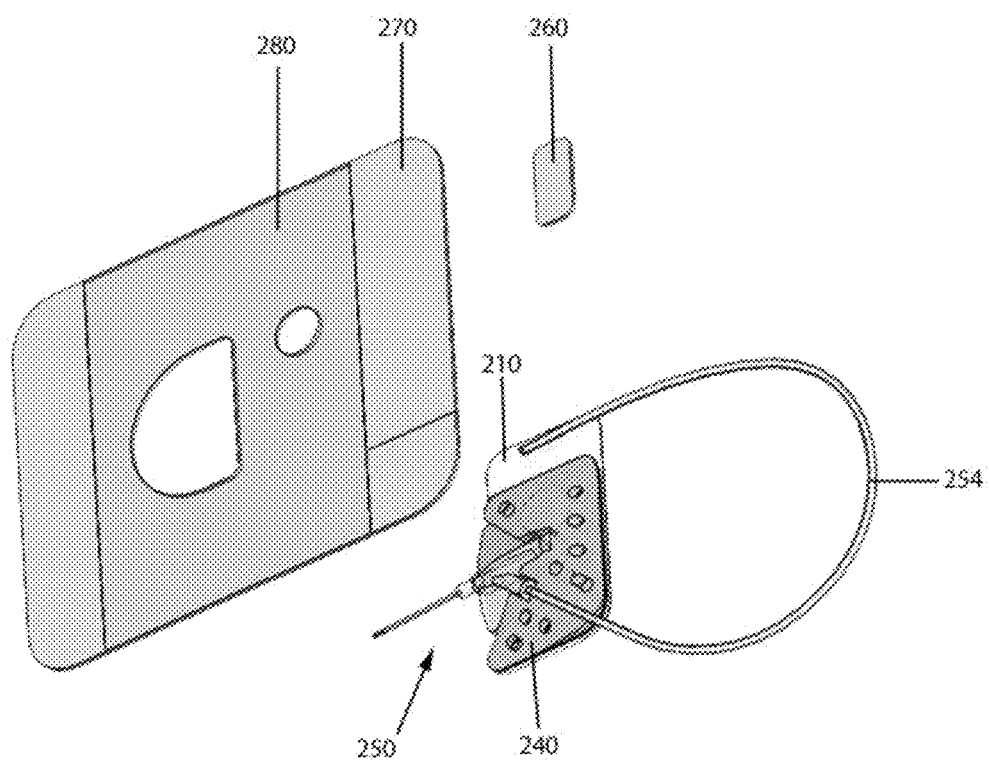
Figure 2G:
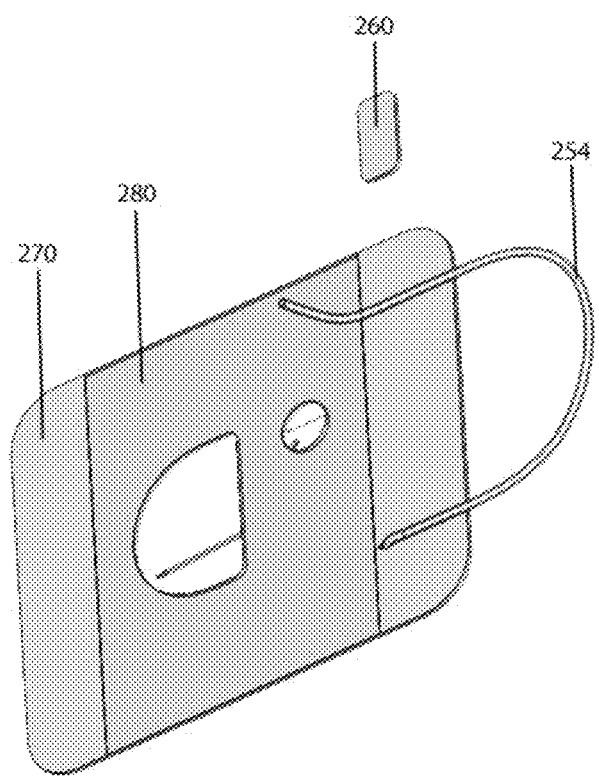
Figure 2H:
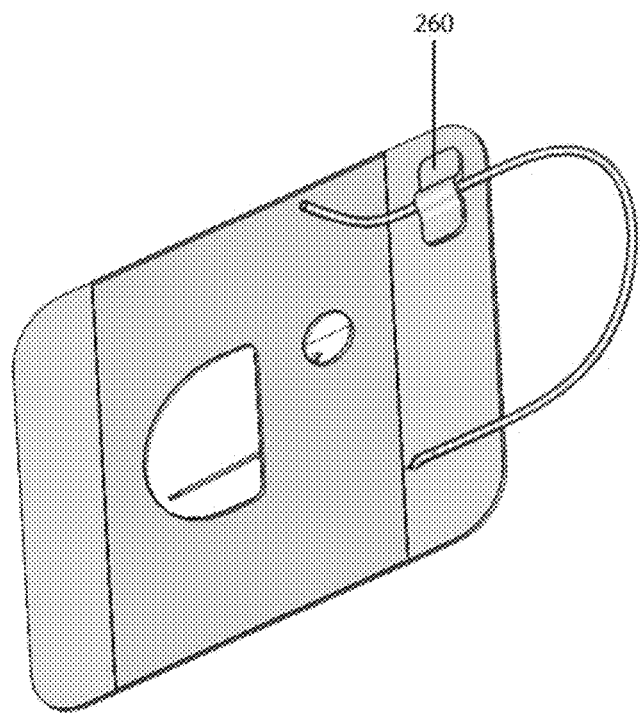
Figure 21:
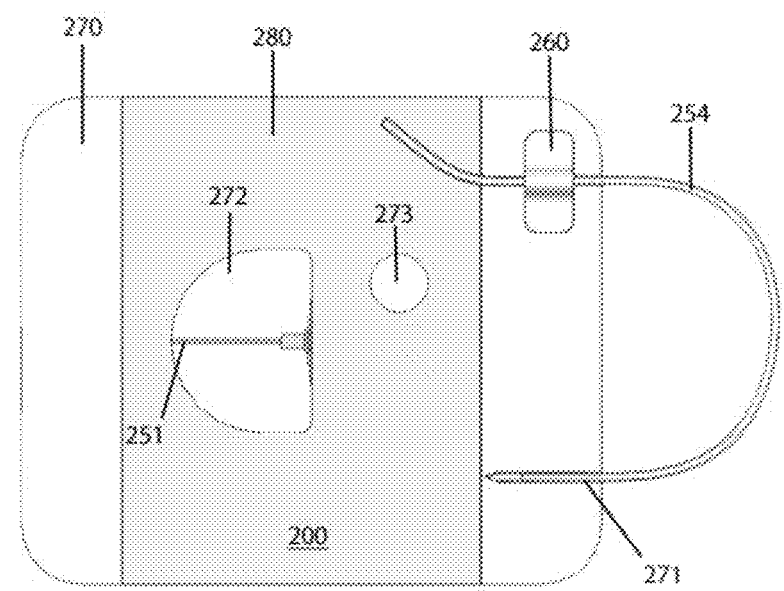

FIGS. 2A-2M illustrate various views of another embodiment of a catheter dressing 200 according to some embodiments described herein. As shown in FIG. 2A-2B, the catheter dressing 200 can include a peel back protective paper 210 (shown in more details in FIG. 2M) configured to cover an adhesive tape 220. The adhesive tape 220 can be made from any suitable material available in the art. For example, the adhesive tape 220 can be a double-sided non-woven adhesive tape, such as a silicone/hydrocolloid tape. The adhesive tape 220 can be attached to a flexible tube seal and securement device 240, and be configured to have substantially the same dimensions as flexible tube seal and securement device 240. The adhesive tape 220 can also include one or more recess 225 regions. The recess regions 225 can be configured to hold any suitable material known in the art. For example, the recess regions 225 can hold items 230 such as an antiseptic sponge, sac or gel (e.g., chlorhexidine, isopropyl alcohol, etc.). Alternatively or additionally, the flexible tube seal and securement device 240 can include one or more recess regions 245. The recess regions 245 can be configured to correspond or line up with the recess regions 225 of the adhesive tape 220. These recessed regions 245 can also be configured to hold any suitable item 230 known in the art, for example an antiseptic sponge, sac or gel (e.g., chlorhexidine, isopropyl alcohol, etc.).

The adhesive tape 220 can include can have one or more slots 222, 223. These slots 222, 223 can be configured to line up with (or have the same or similar dimensions as) one or more corresponding slots 212, 213 on the peel back protective paper 210. The flexible tube seal and securement device 240 can also include one or more slots 242, 243 that can also be arranged to line up with (or have the same or similar dimensions as) corresponding slots 212, 213 of the peel back protective paper 210 and/or corresponding slots 222, 223 of the adhesive tape 220.

The slots 242, 243 of the flexible tube seal and securement device 240 and/or the corresponding slots 212, 213 on the peel back protective paper 210 and/or the slots 222, 223 of the adhesive tape 220 can be arranged to receive one or more fit ports 252 and 253, respectively, of catheter 250. The flexible tube seal and securement device 240 can also include a channel 241 configured to receive at least a portion of an extension tubing 254 from the catheter system 250.

The catheter system 250 can be any suitable catheter system available in the art. For example, the catheter system 250 can be BD Nexiva™ catheter system. The catheter system 250 can include a catheter 251, one or more wings 255, a side arm 253, a back arm 252 and an extension tubing 254.

The dressing 200 can further include an adhesive pad 270. The adhesive pad 270 can include one or more cut outs (e.g., windows) 272 and 273 and a slit 271. The dressing 200 can also include a thin film 280. The thin film 280 can be positioned on top of the pad 270 such that it covers windows 272 and 273 of the pad. The thin film 280 can be transparent.

The peel back paper 210 can be configured such that it can be removable to expose the adhesive tape 220 on the securement device 240. A separate adhesive tape 260 can also be used to secure at least a piece of extension tubing (e.g., IV tubing) from the catheter 250 to the pad 270 or the film 280.

Figure 2J:
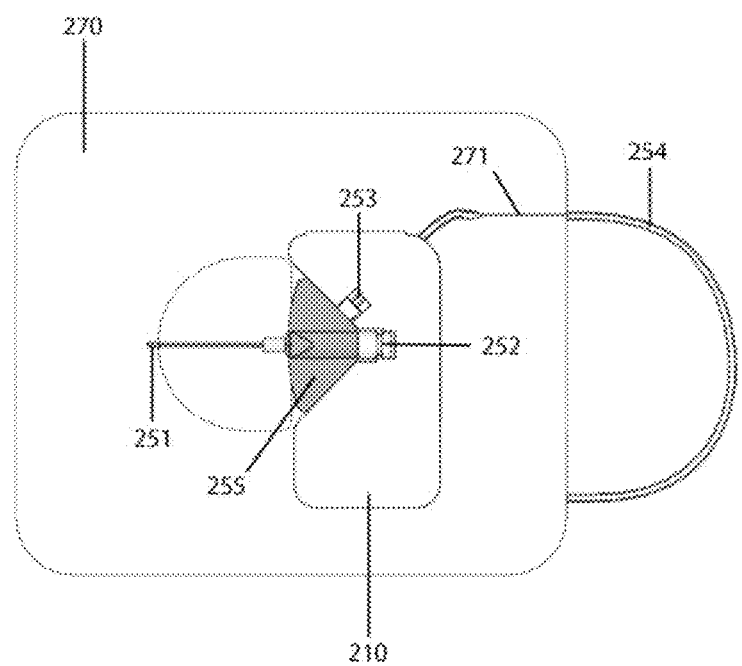

In the examples shown in FIGS. 2I and 2J, interior (bottom portion adjacent to the patient's body) and exterior sides (top portion) of the dressing 200 are illustrated. As shown, the slit 271 can be used to pass at least a portion of the extension tubing 254 from the interior side of the adhesive pad (FIG. 2I) 270 to the exterior side of the adhesive pad 270 (FIG. 2J).

Figure 2K:
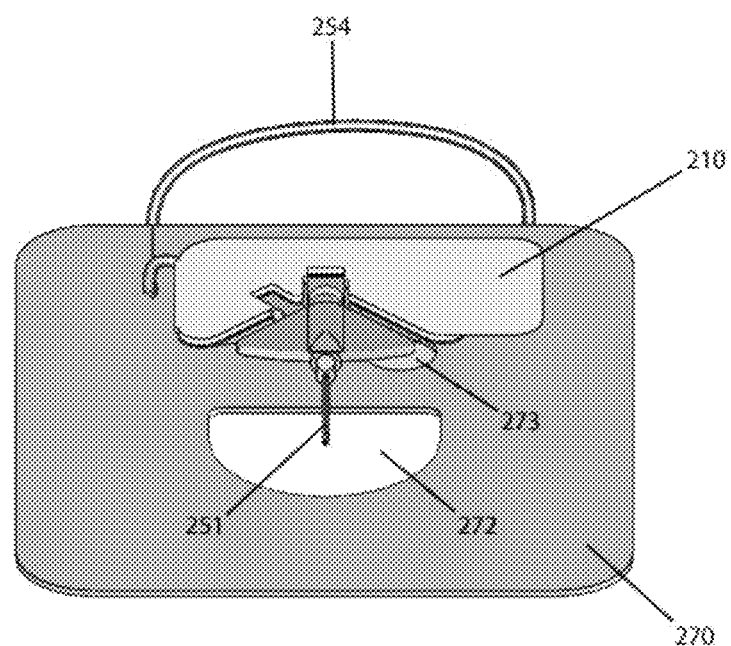
Figure 2L:
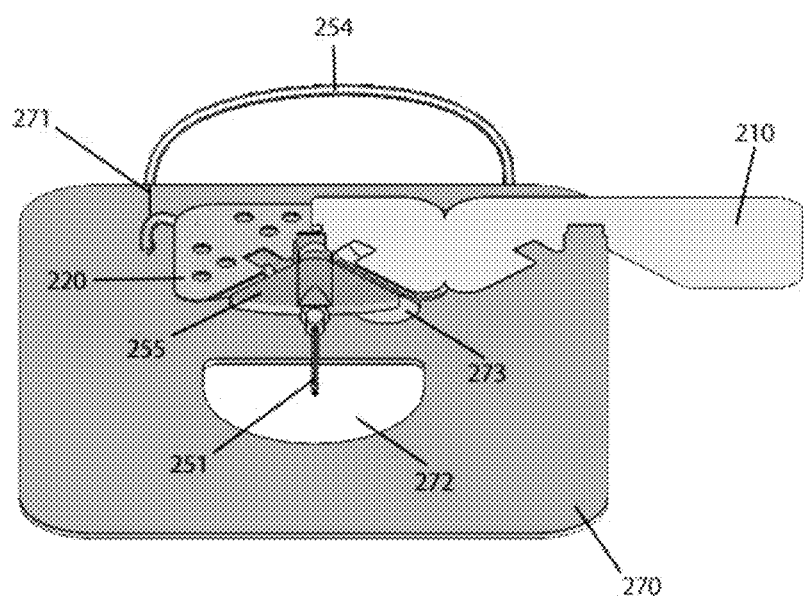
Figure 2M:
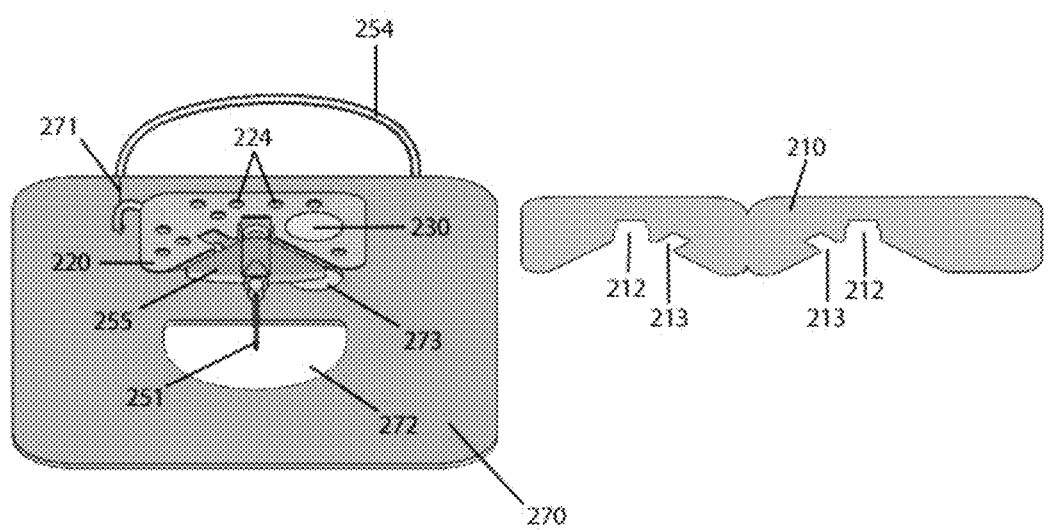

FIG. 2I and FIG. 2K illustrate the adhesive pad 270 from a top view (FIG. 2I) and bottom view (FIG. 2K). The adhesive pad 270 can be an integrated mating body that has been fused to the adhesive dressing plate. As shown in FIG. 2I (the top perspective view), the window covering 272 of the dressing 200 can be an external circumferential sealing flange 272 that is mounted to the top surface of the dressing 200 and configured such that the extension tubing of the catheter 251 is visible through the top surface of the flange 272. Similarly, as shown in FIG. 2K, the extension tubing 251 can be disposed under the window covering (e.g., flange) 272 such that it is visible on the exterior side of the adhesive pad 270.

Figure 2N:
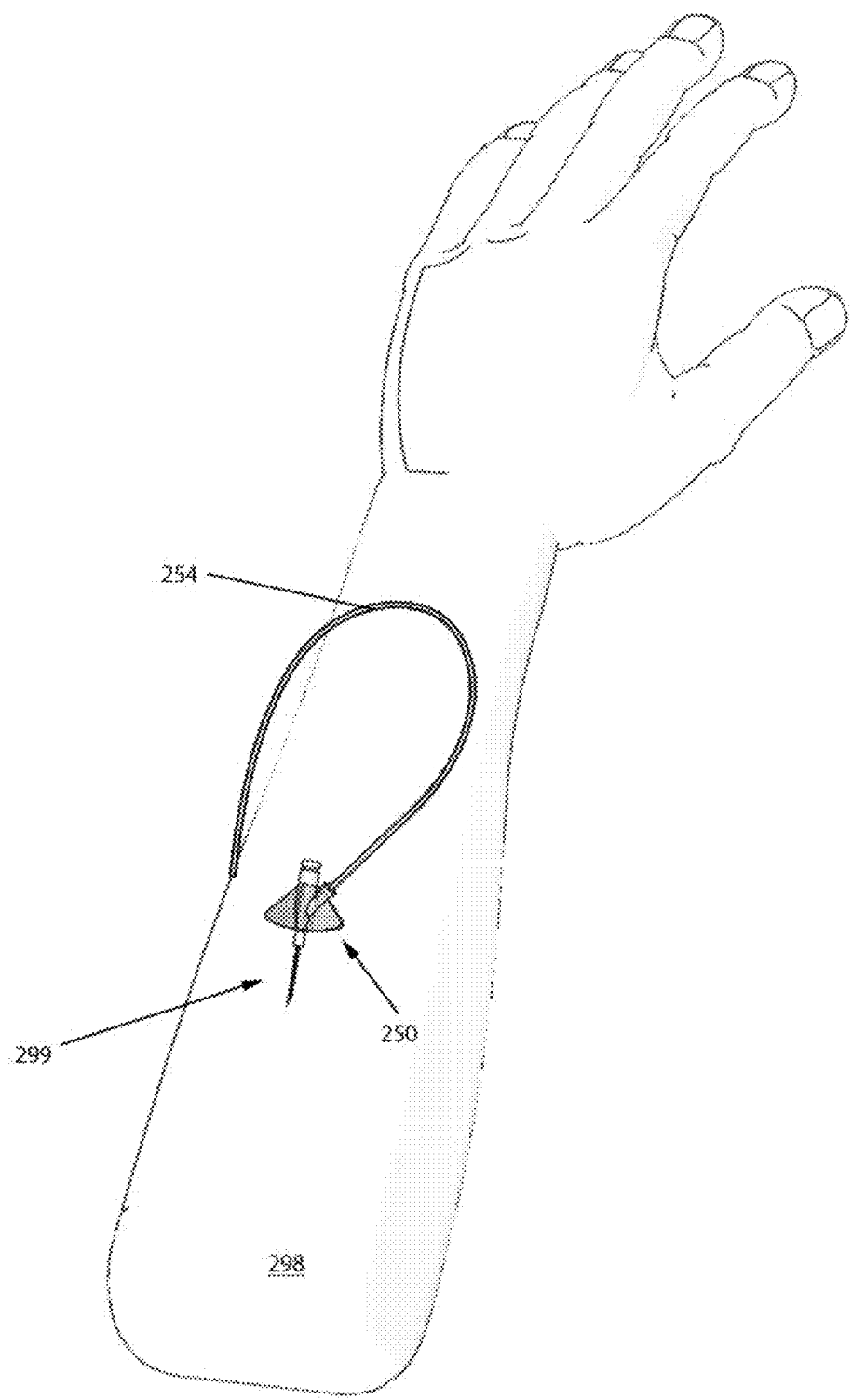
Figure 20:
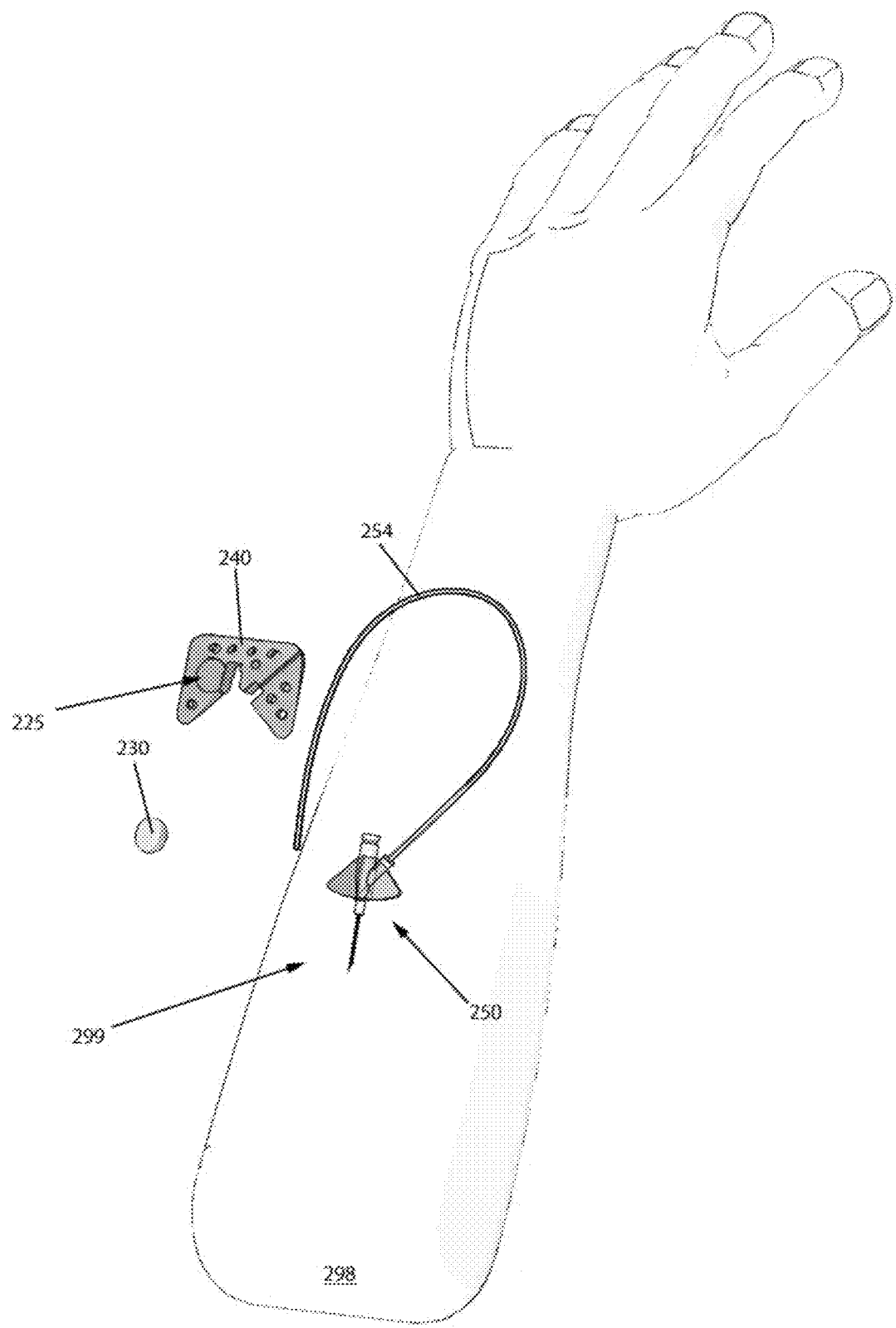

FIGS. 2N-2AA illustrate the procedures for placing the device 200 on an inserted catheter. As shown in FIG. 2N, the catheter 250 can be first inserted in an injection site 299 on a portion of a patient's body 298. One skilled in the art should appreciate that, while methods and devices described herein are generally described in connection with catheters implantable in humans, the disclosed methods and devices can also be used in any instance in which a seal is desired around an elongate device implanted into or otherwise extending from a plant, an animal, and/or any non-living machine, structure, or system.

Figure 2P:
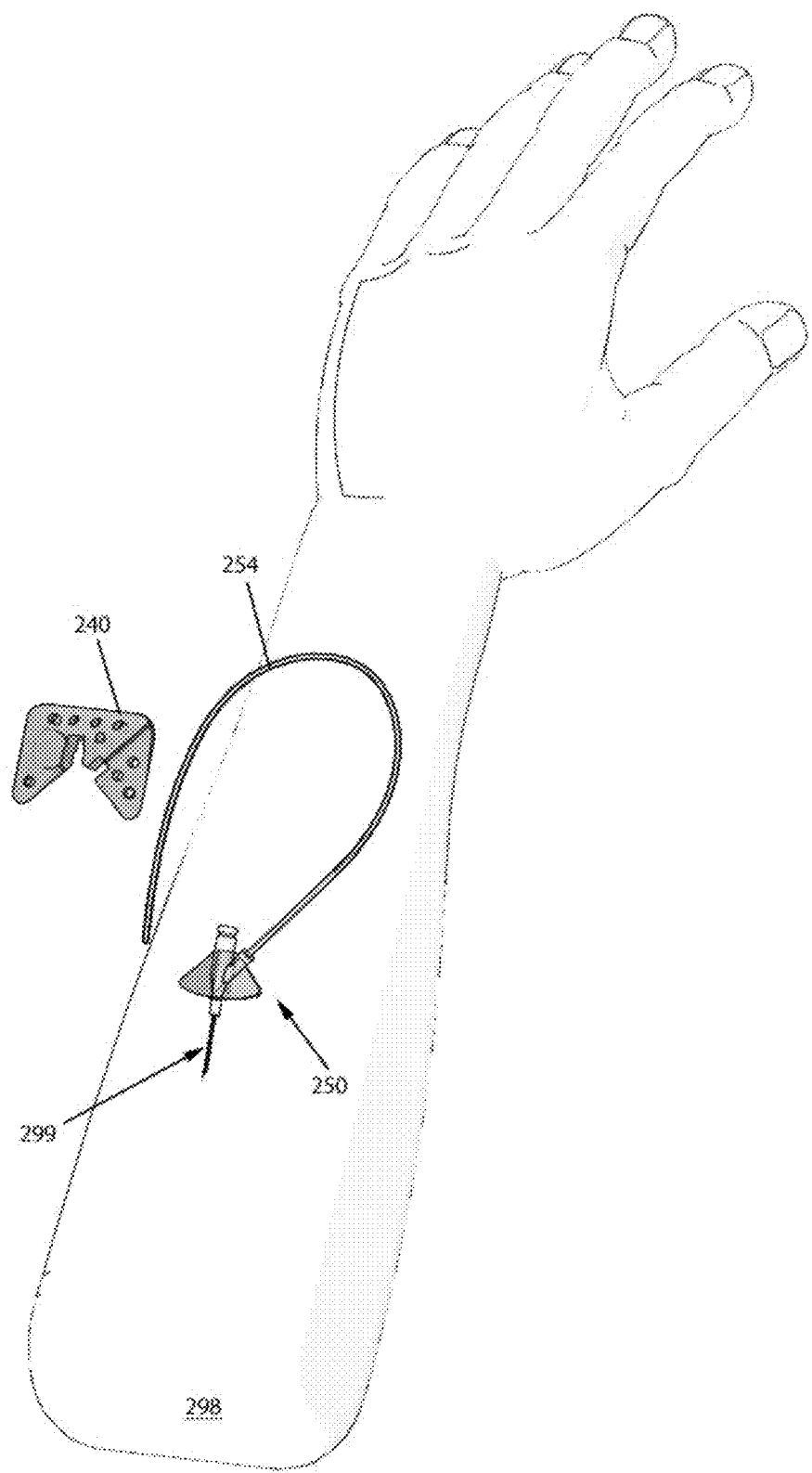

As shown in FIGS. 2O and 2P, once the catheter 250 is inserted into the injection site 299, a flexible tube seal and securement device 240 can be positioned over the catheter 250 to secure the catheter 250 in place. As shown in FIG. 2O, the catheter can include one or more recess regions 225 for holding suitable items, such as example an antiseptic sponge, sac or gel (e.g., chlorhexidine, isopropyl alcohol, etc.). As noted previously, the flexible tube seal and securement device 240 can also include a channel 241 configured to receive at least a portion of an extension tubing 254 from the catheter system 250. Once applied to the injection site 299, the catheter system 250 can be secured to the flexible tube seal and securement device 240 by inserting at least a portion of an extension tubing 254 into the channel 241.

Figure 2Q:
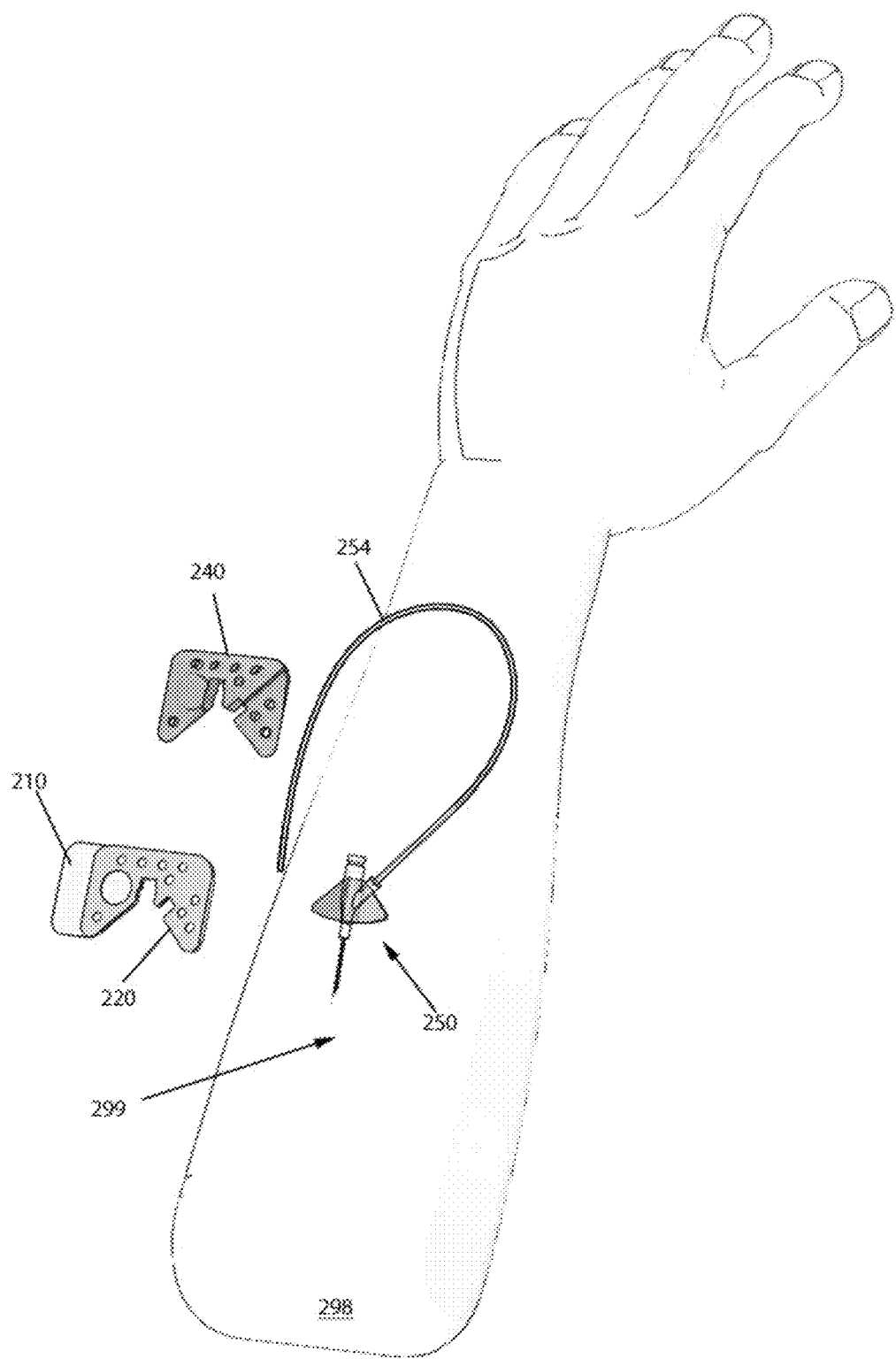
Figure 2R:
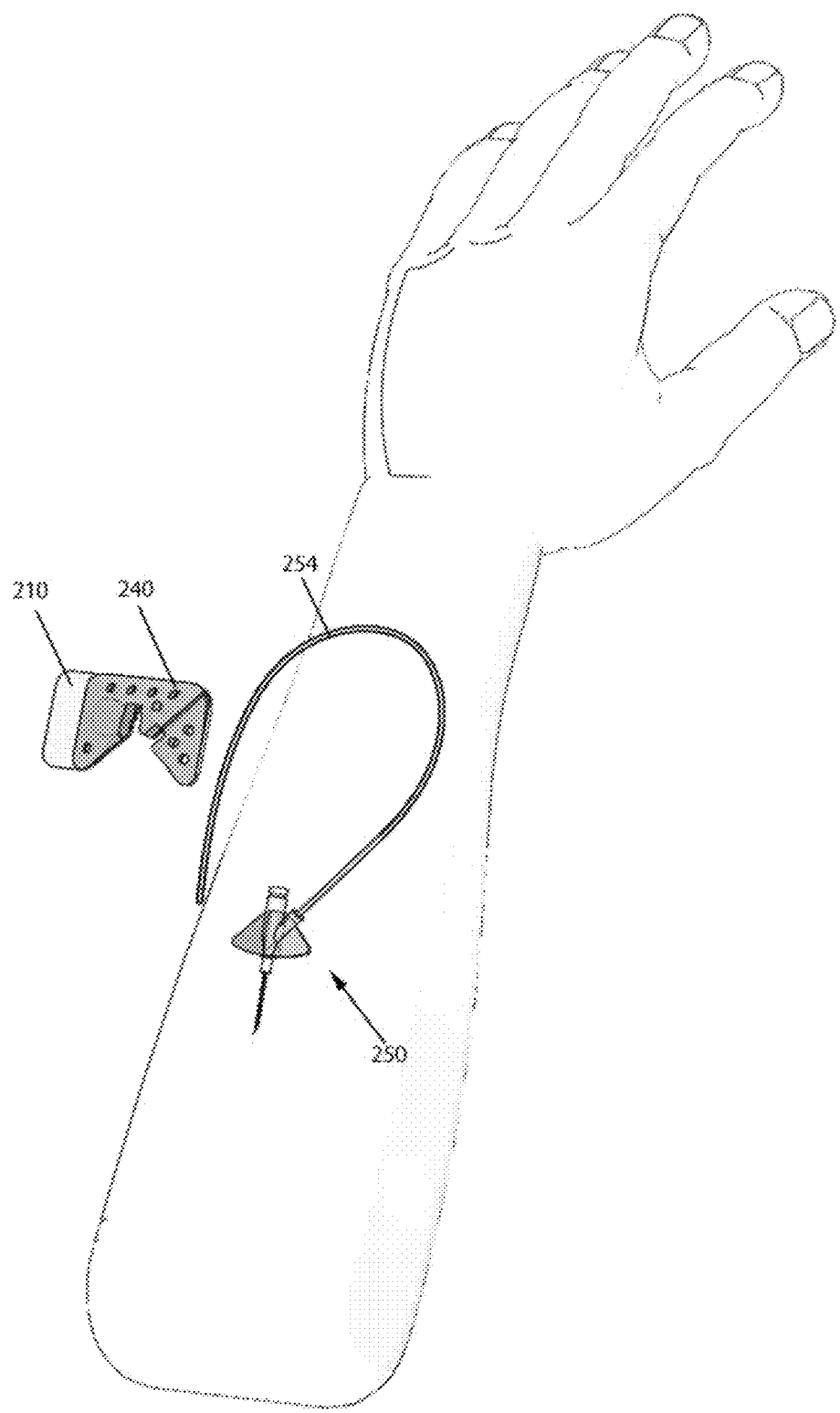
Figure 2S:
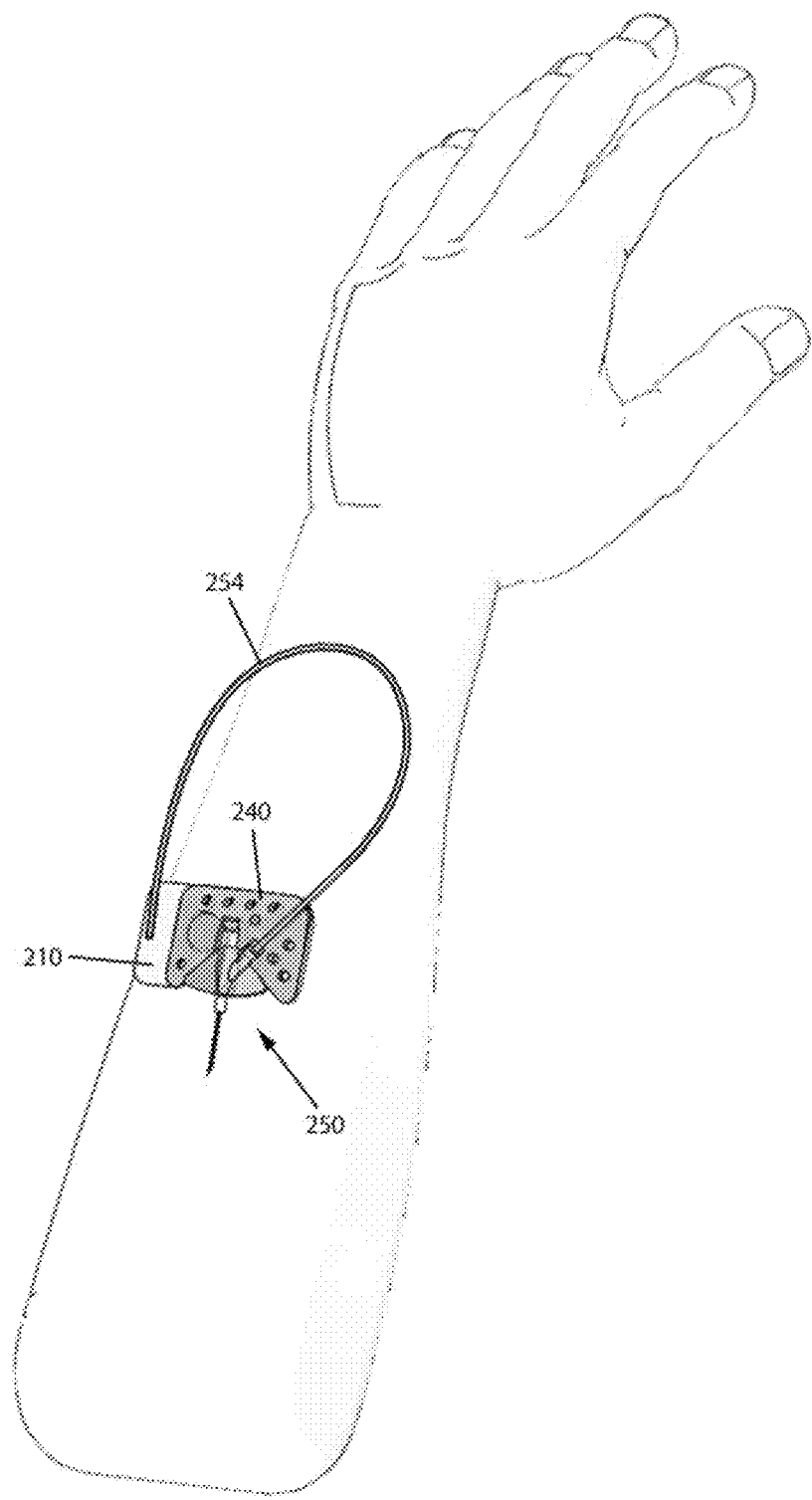
Figure 2T:
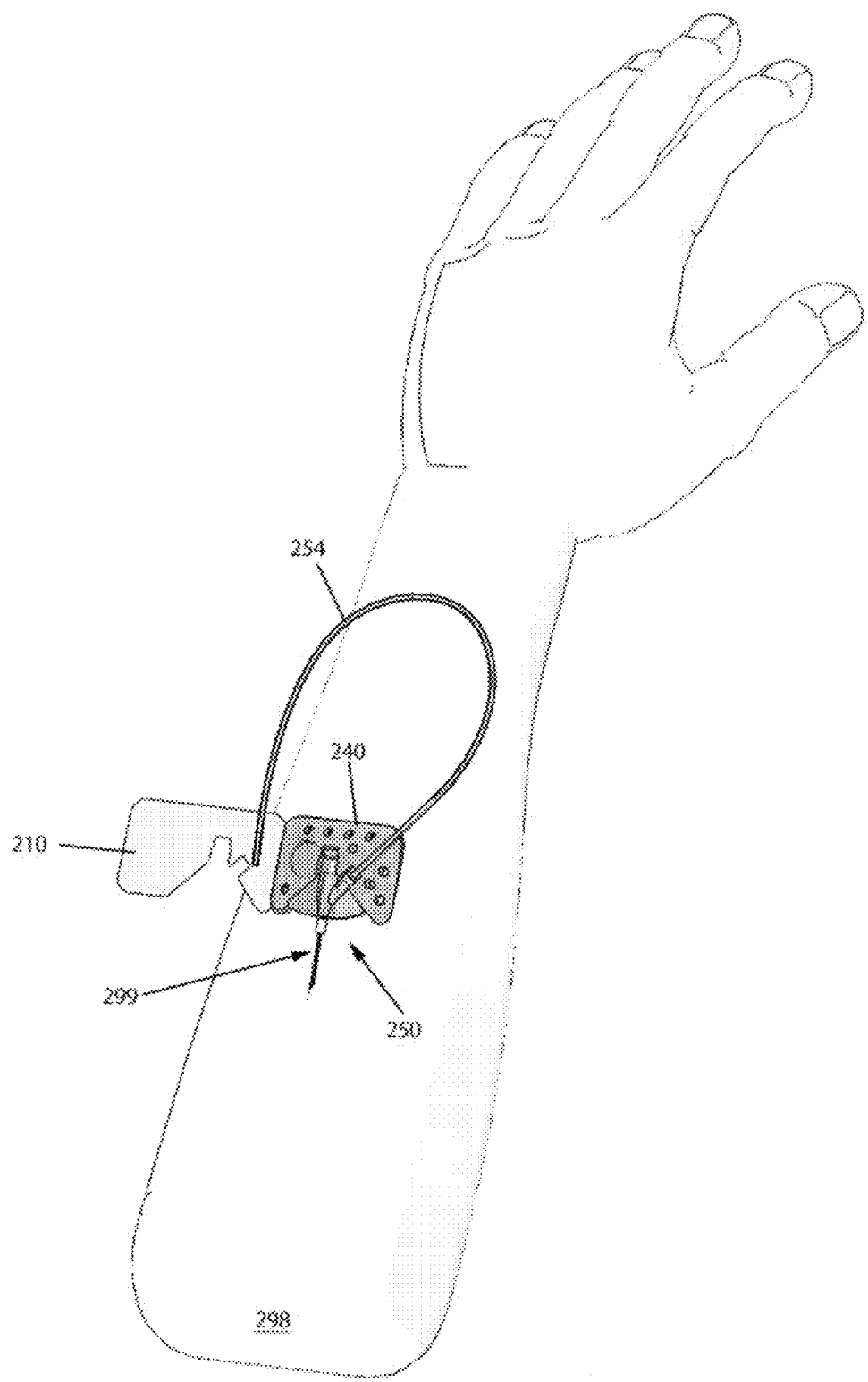
Figure 2U:
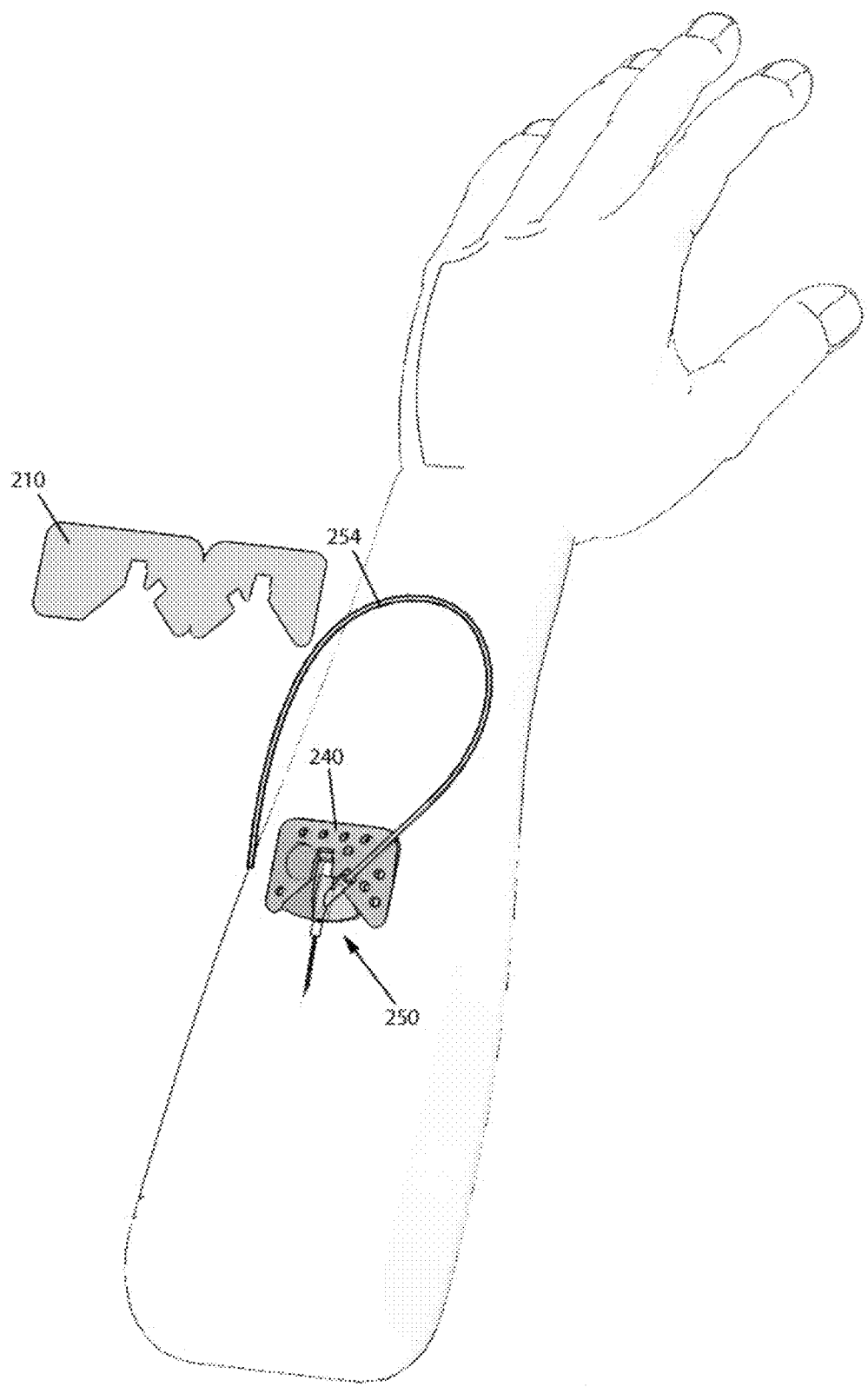
Figure 2V:
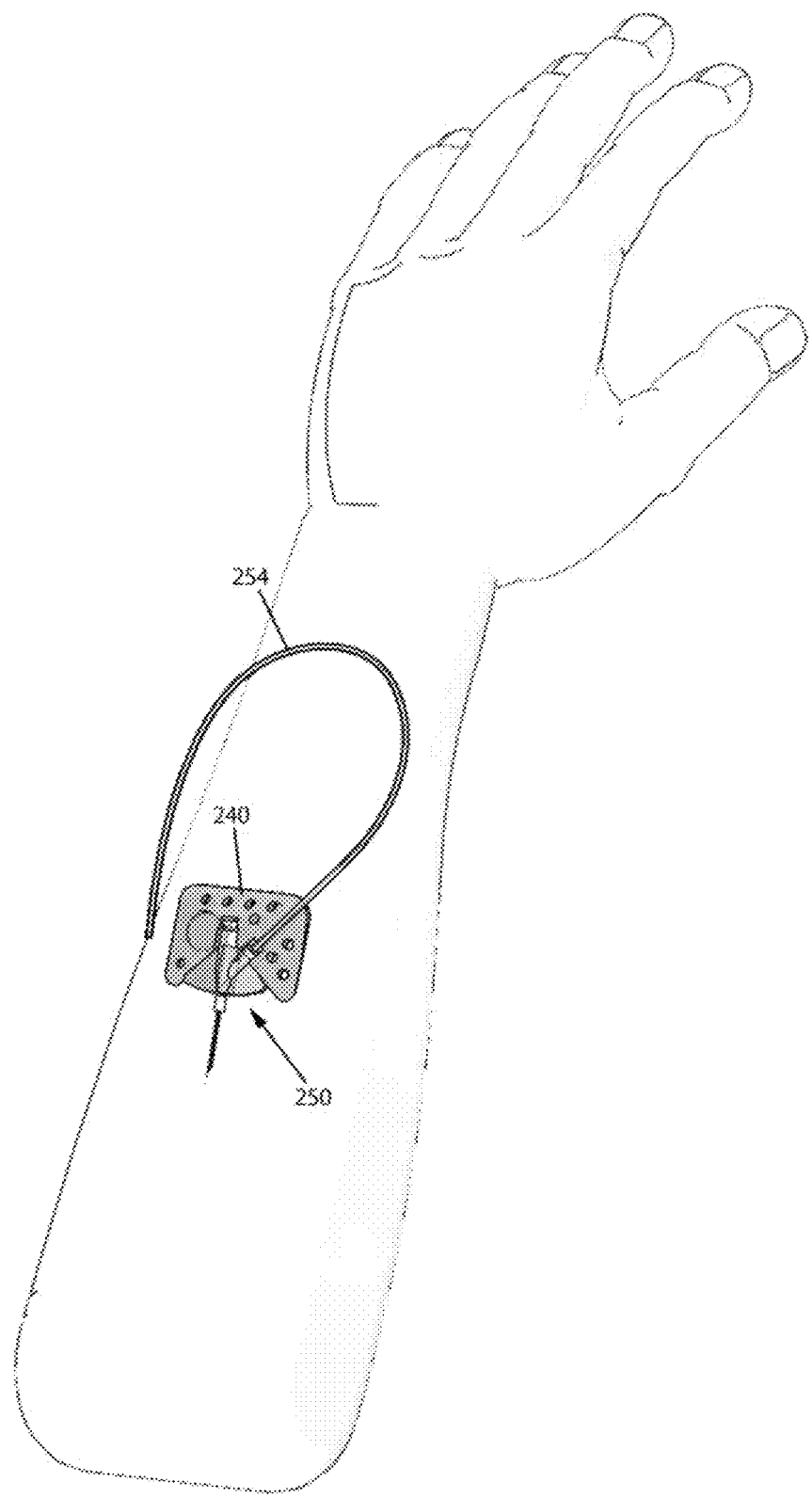
Figure 2W:
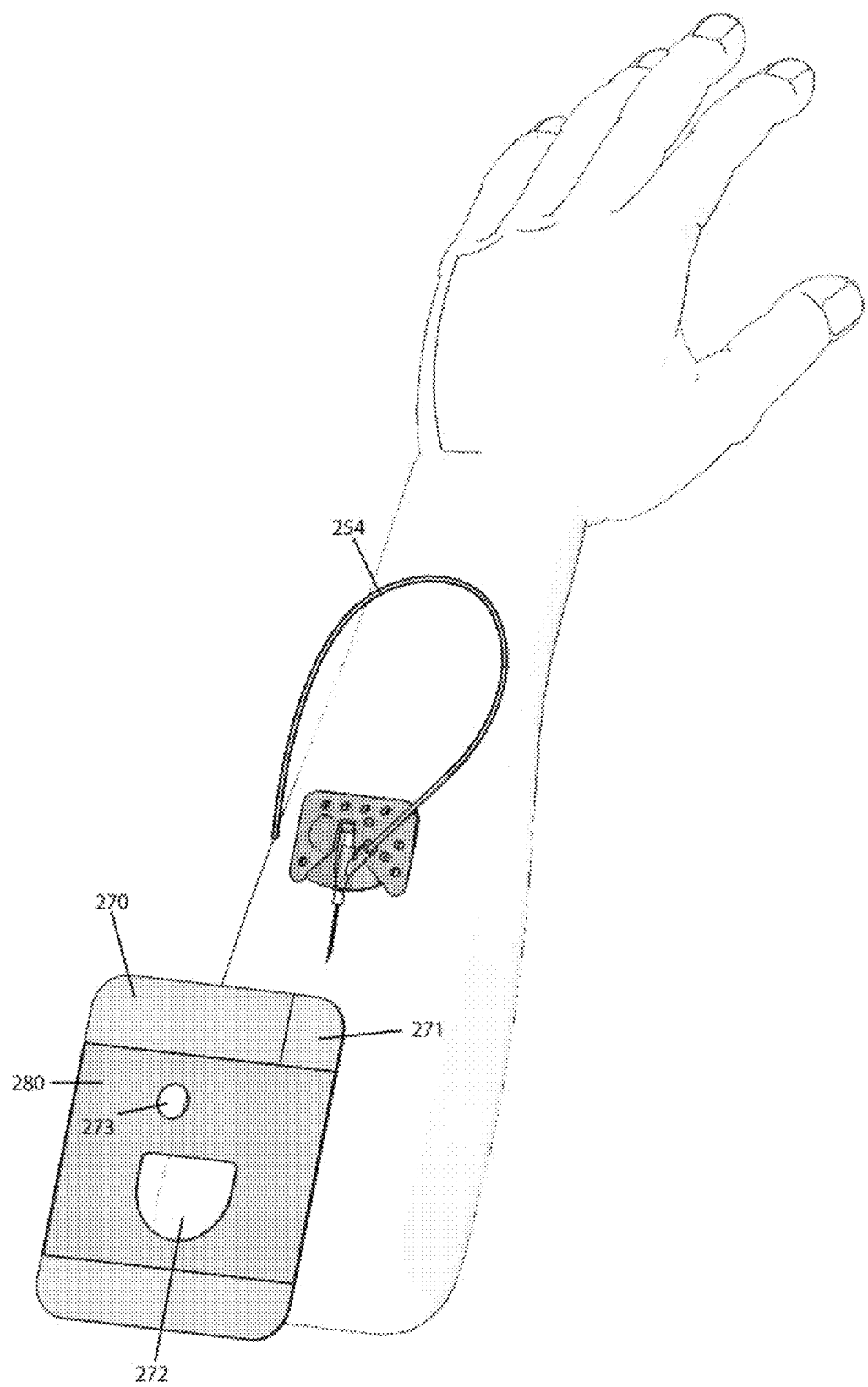
Figure 2X:
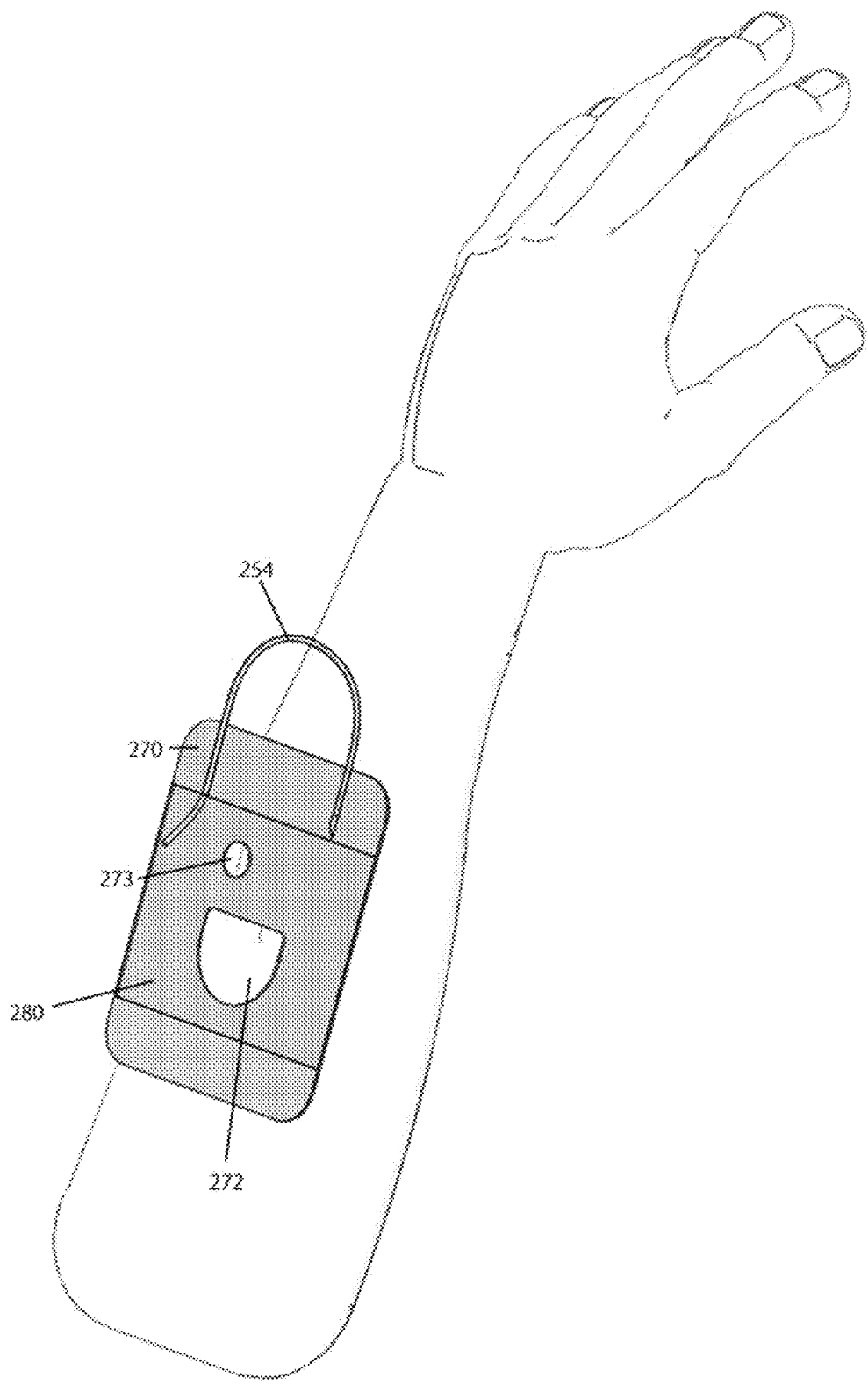
Figure 2Y:
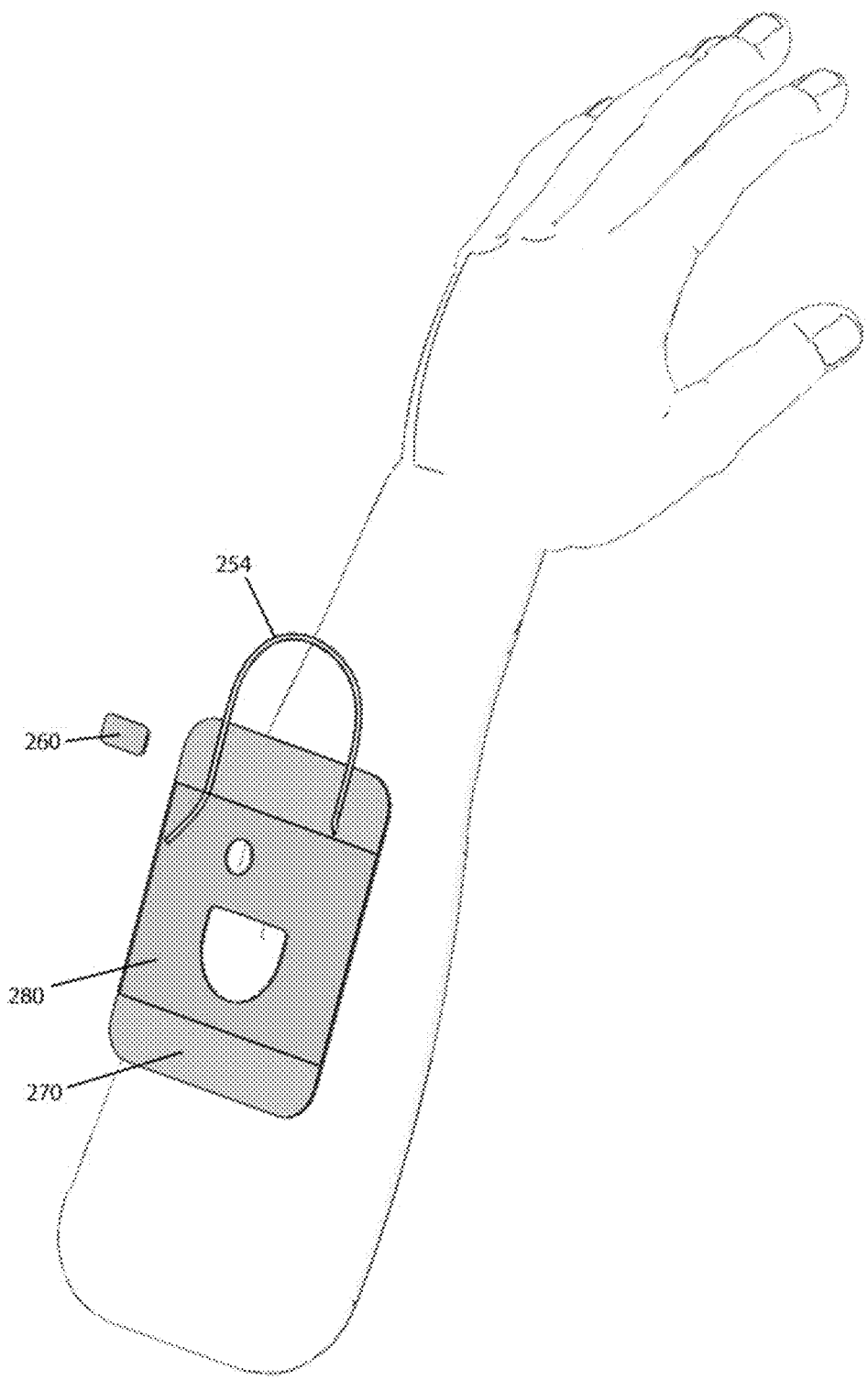
Figure 2Z:
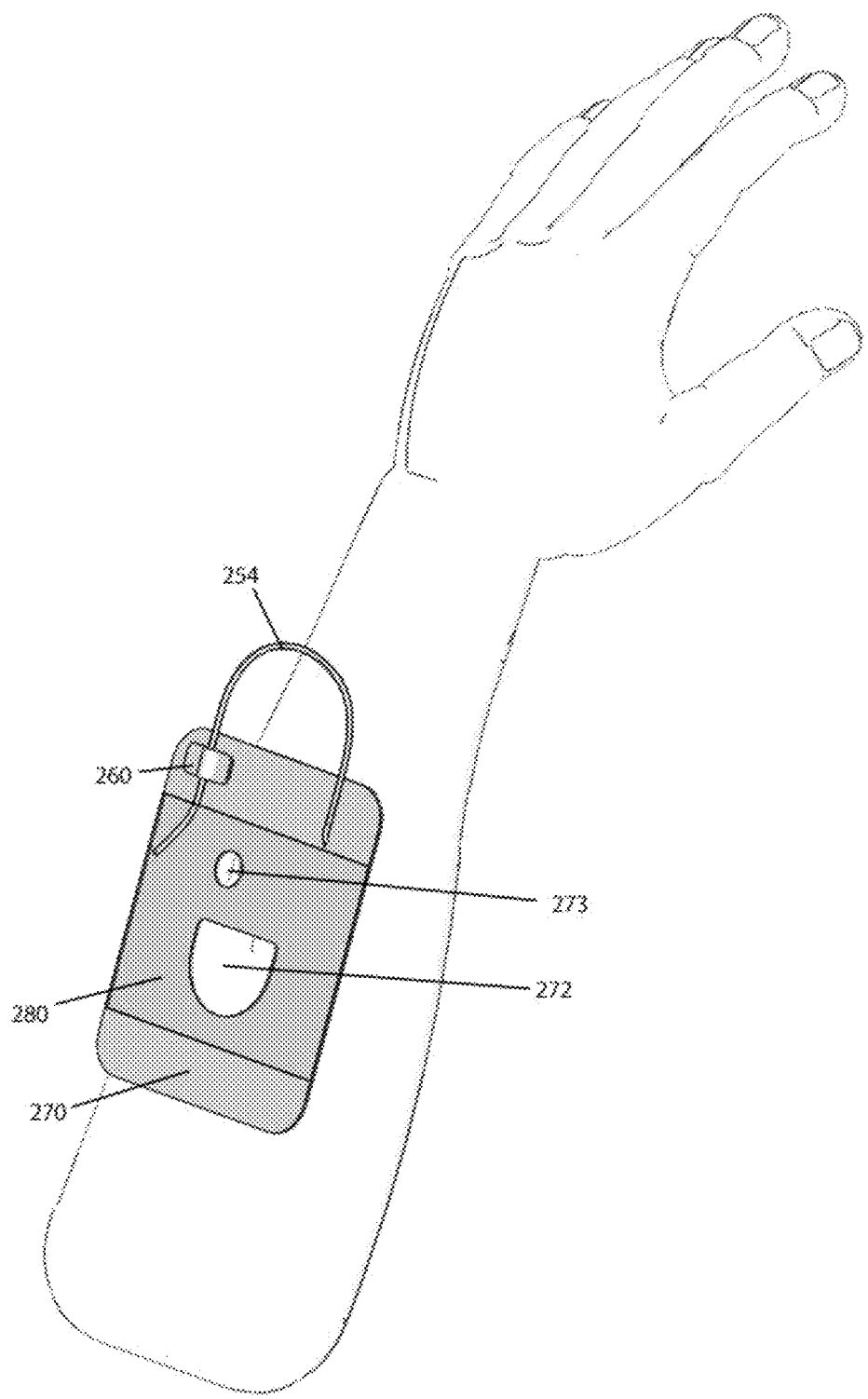
Figure 2A:
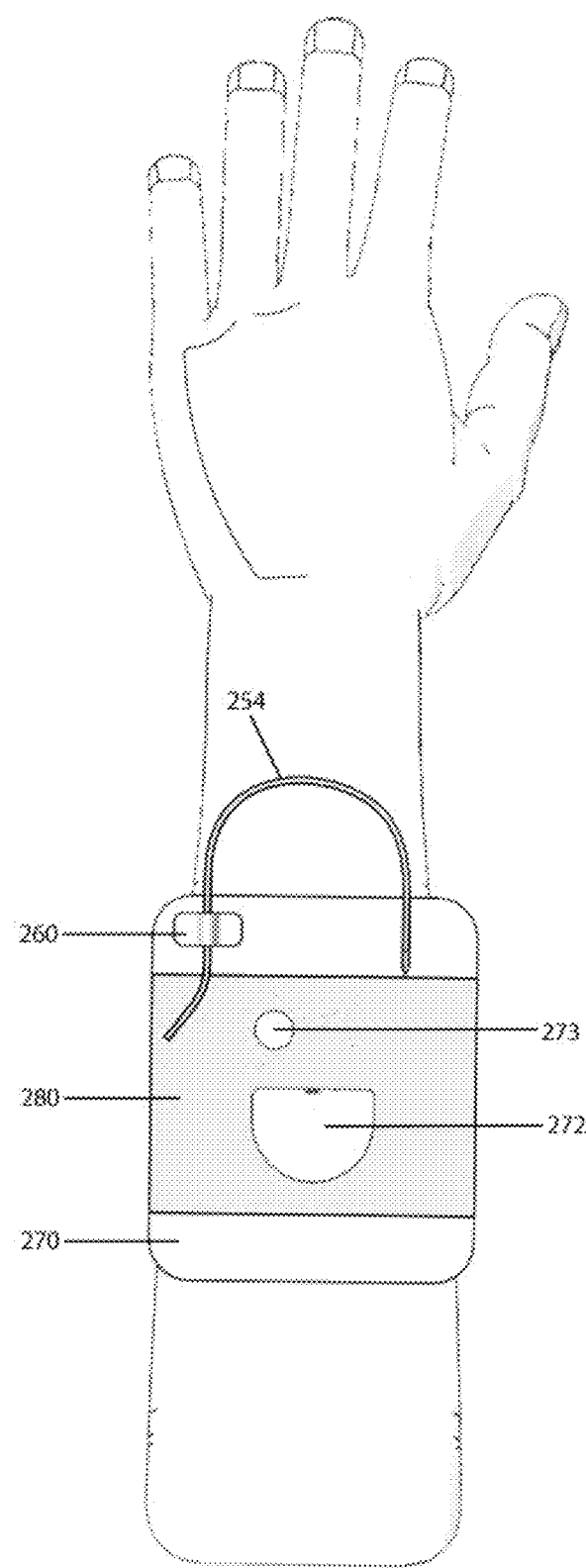

As shown in FIGS. 2Q and 2R, an adhesive tape 220 can then be applied over the flexible tube seal and securement device 240. The adhesive tape 220 can include a peel back protective paper 210 that is first removed in order to expose the adhesive tape 220. The adhesive tape 220 can be attached to a flexible tube seal and securement device 240 and used to secure the flexible tube seal and securement device 240 in place. FIGS. 2S and 2T illustrate that the adhesive tape 220 can be first placed on the flexible tube seal and securement device 240 without removing the peel back protective paper 210 (FIG. 2S). The peel back protective paper 210 can subsequently be removed (FIG. 2T) to expose the adhesive for use in securing the flexible tube seal and securement device 240 to the insertion site 299 and/or the patient's body 298. The adhesive tape 220 can be used to secure the flexible tube seal and securement device 240 by attaching the flexible tube seal and securement device 240 on one or more sides/corners of the device 240 to the surrounding body 298. Once the peel back protective paper 210 is removed (FIG. 2U), an adhesive pad 270 can be applied to secure the flexible tube seal and securement device 240 in place. As noted, the thin film 280 can be positioned on top of the pad 270 such that it covers windows 272 and 273 of the pad 270. As shown in FIG. 2Y, at least a portion of the extension tubing 254 can be passed through to the exterior part of the pad 270 through a slit 271 (e.g., FIG. 2I). As shown in FIG. 2Z (the top perspective view), the window covering 272 can be configured such that the extension tubing of the catheter 251 is visible through the top surface of the flange 272. As shown in FIG. 2AA, another adhesive tape 260 can be used to secure at least a piece of the extension tubing 257 of the catheter 250 to the pad 270 or the film 280.

Figure 3A:
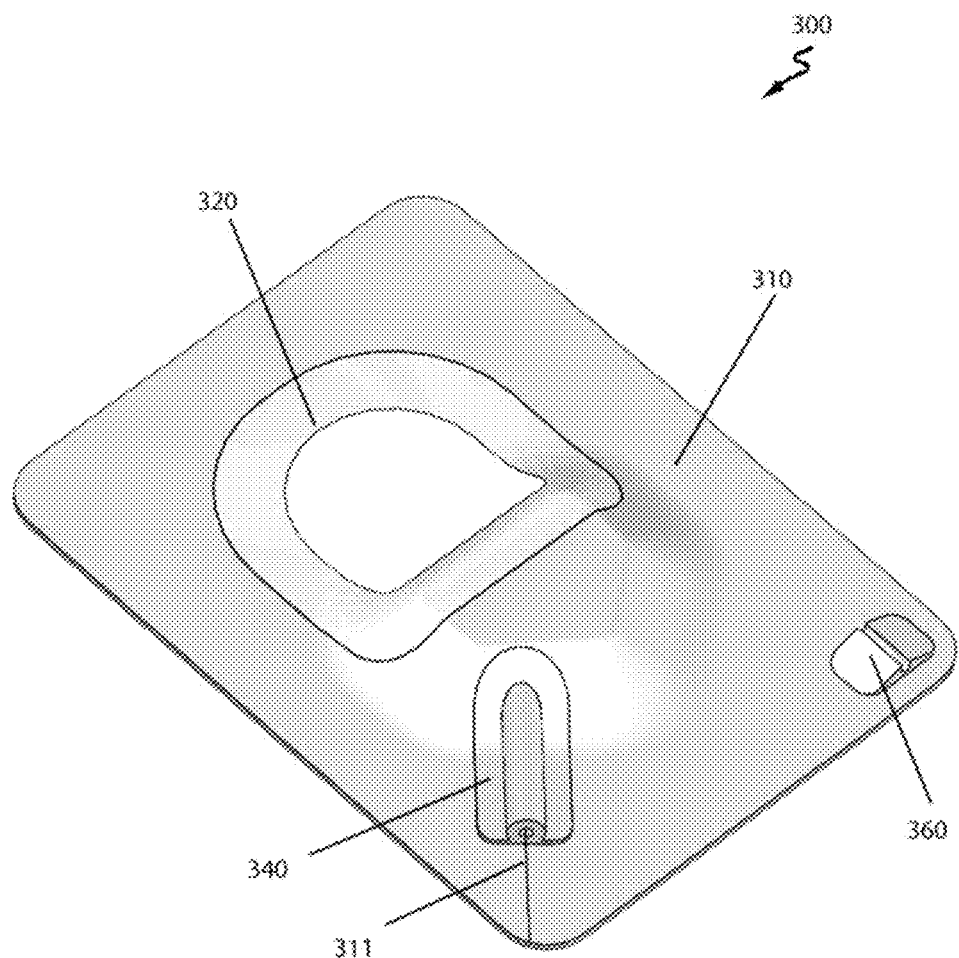
FIGS. 3A-3R illustrate various example sterile dressings according to some embodiments disclosed herein.
Figure 3B:
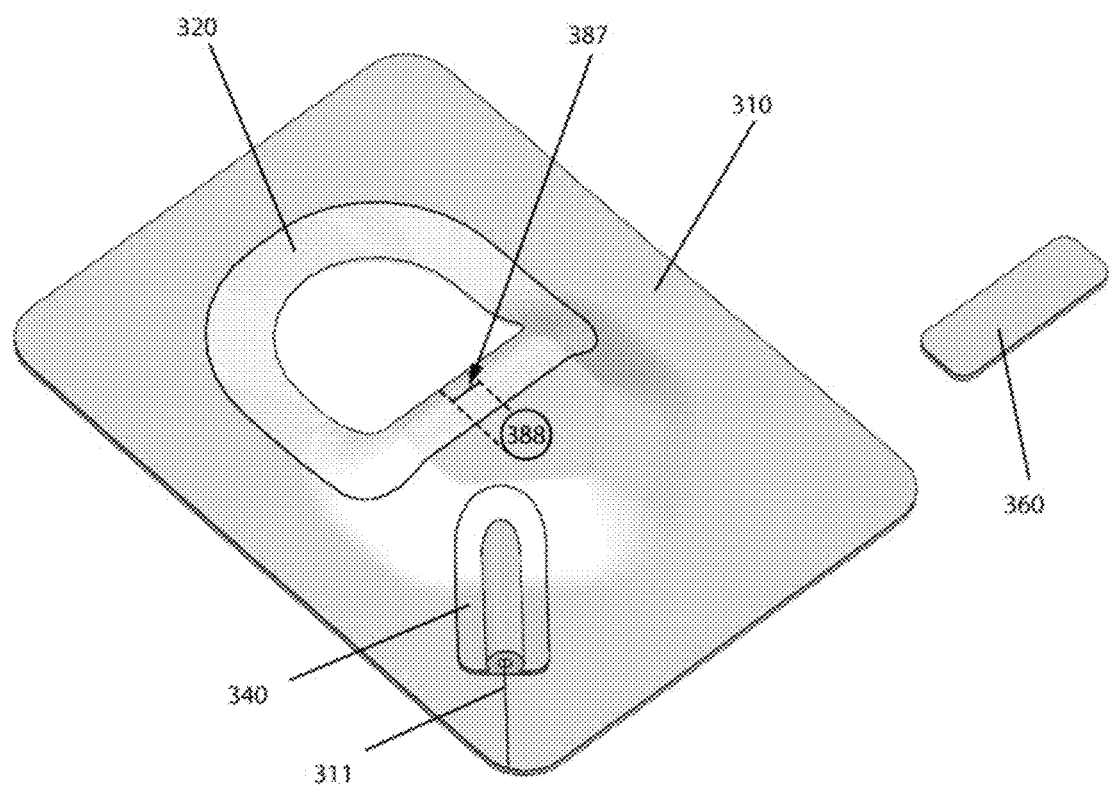
Figure 3C:
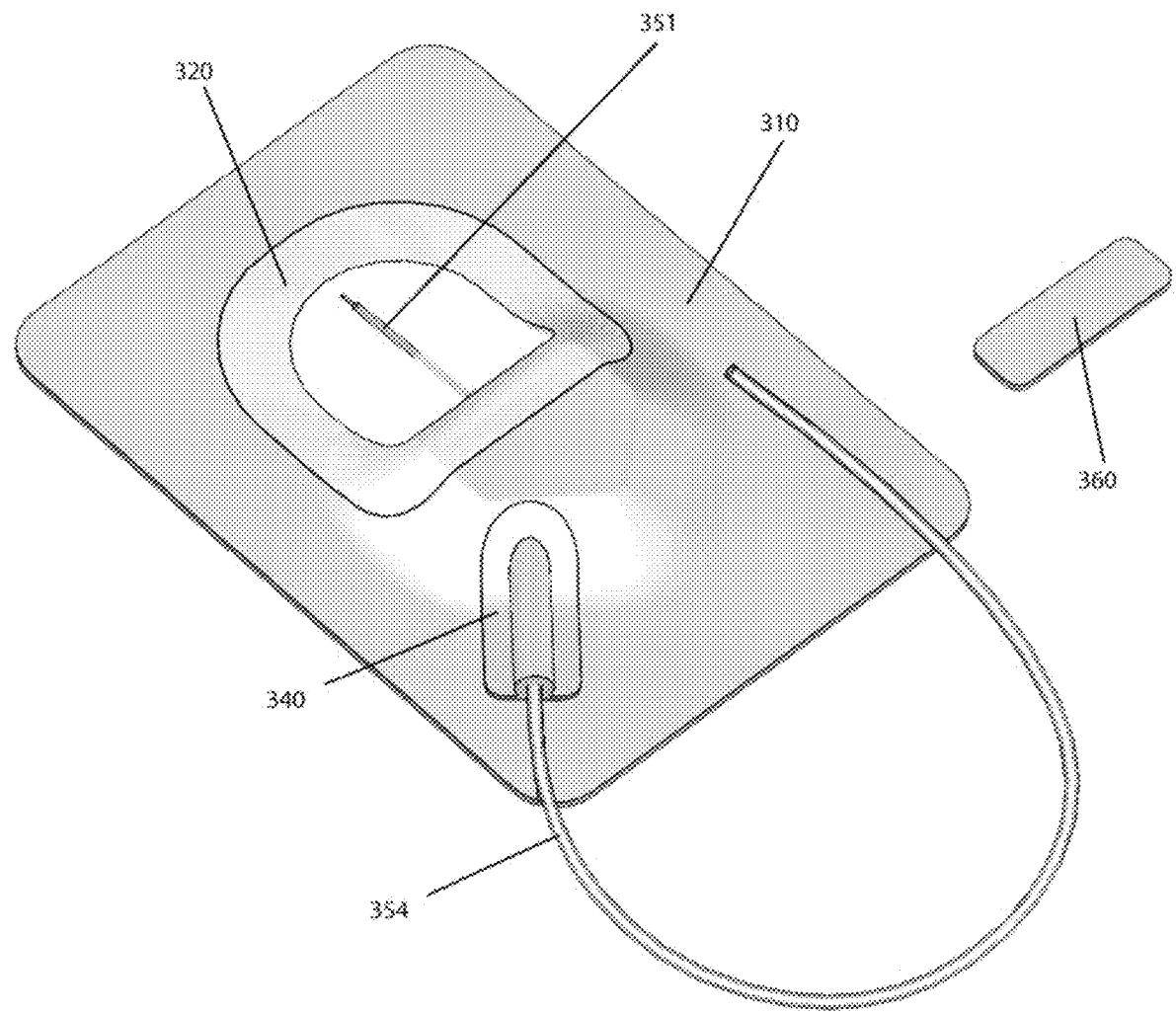
Figure 3D:
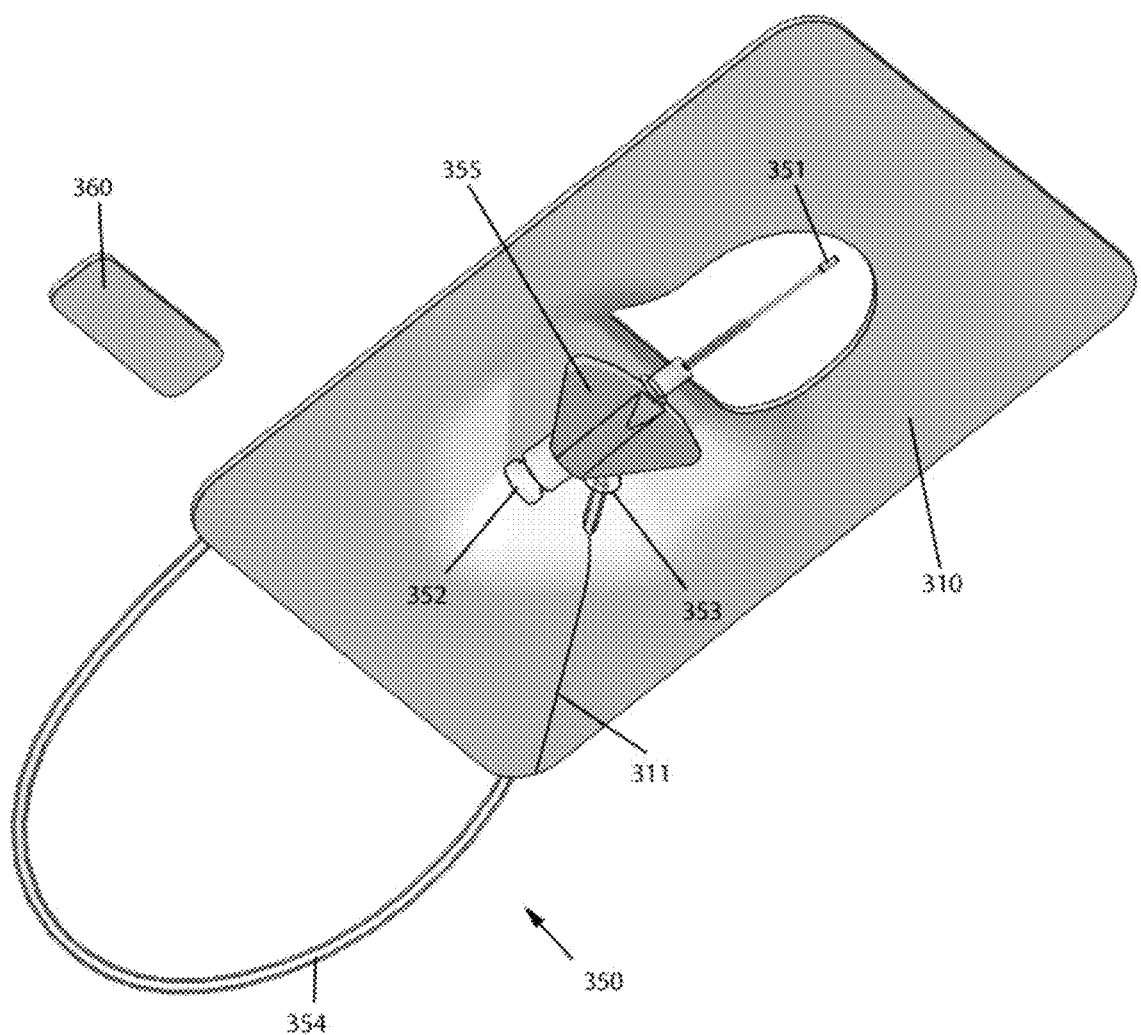
Figure 3E:
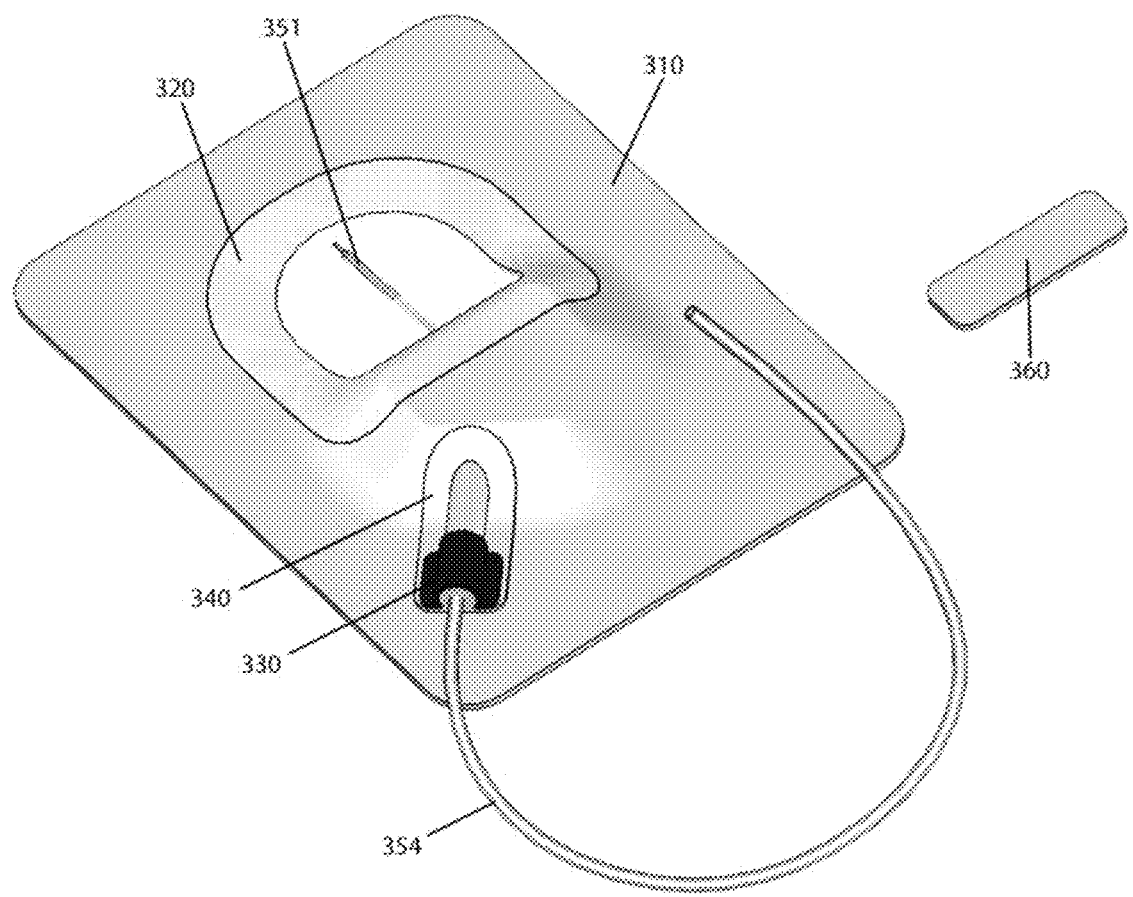
Figure 3F:
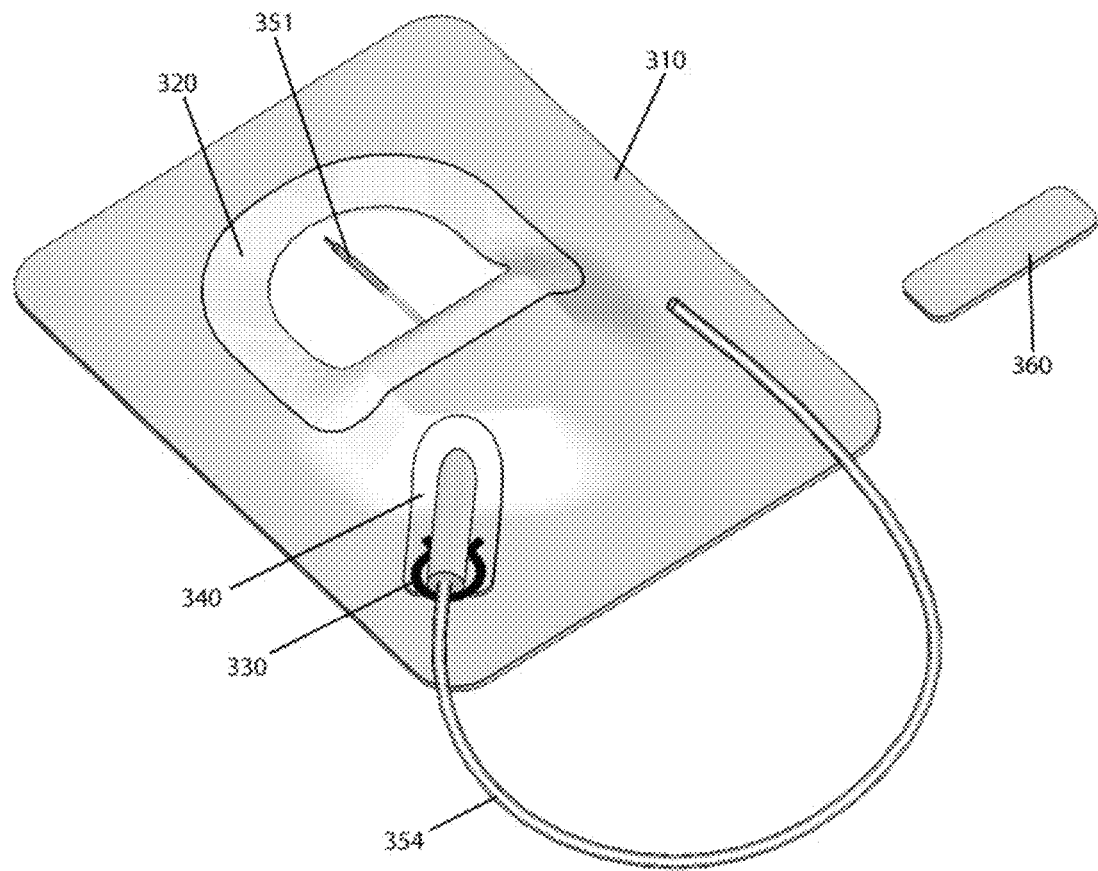
Figure 3G:
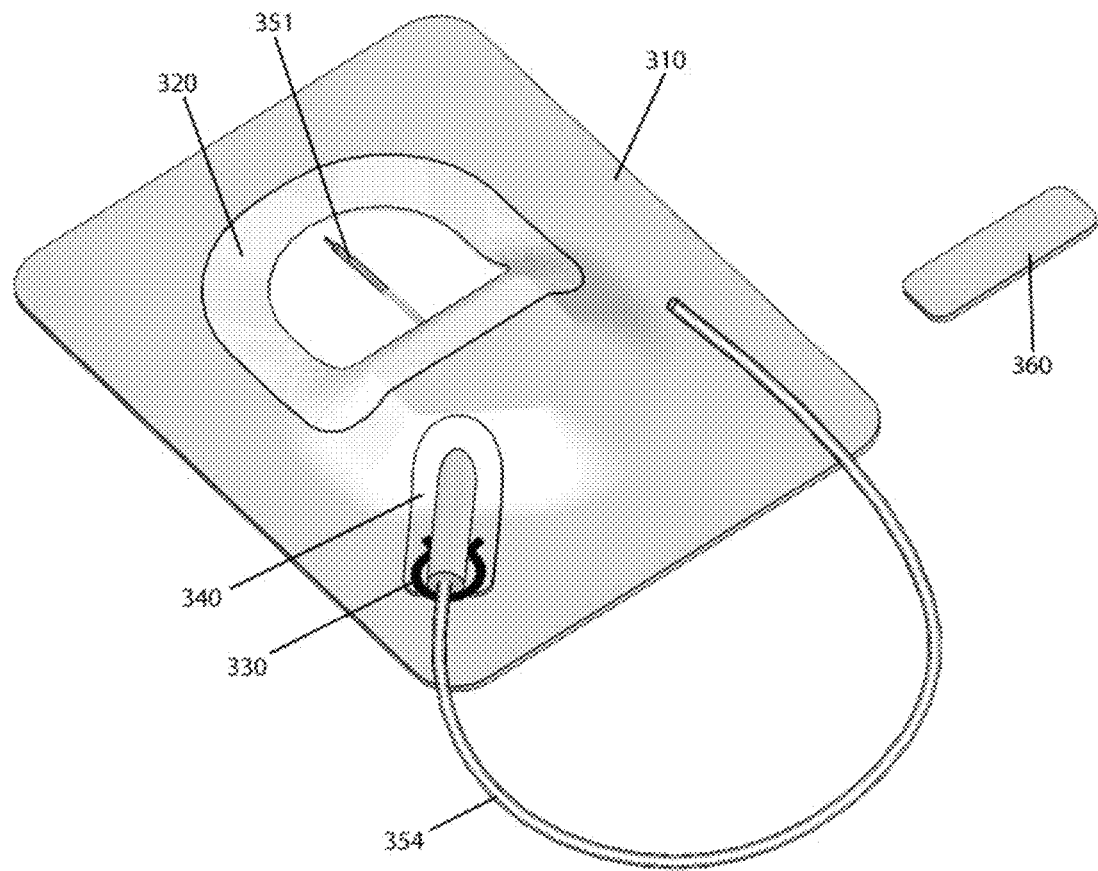
Figure 3H:
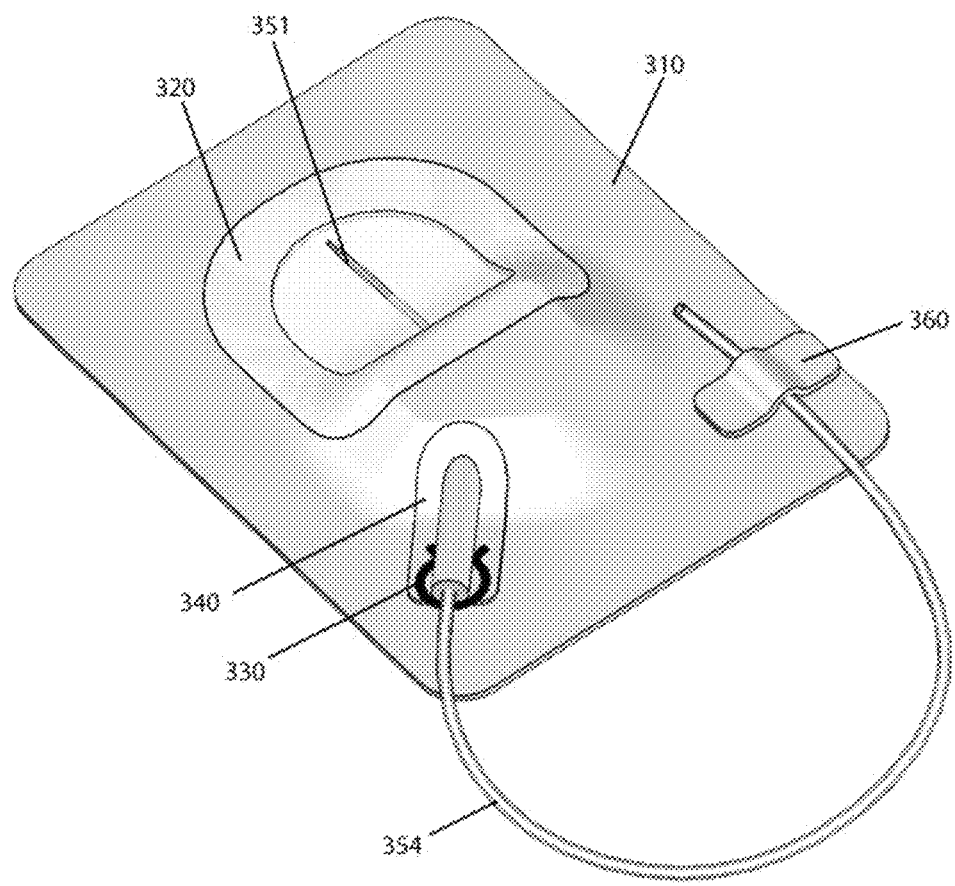
Figure 31:
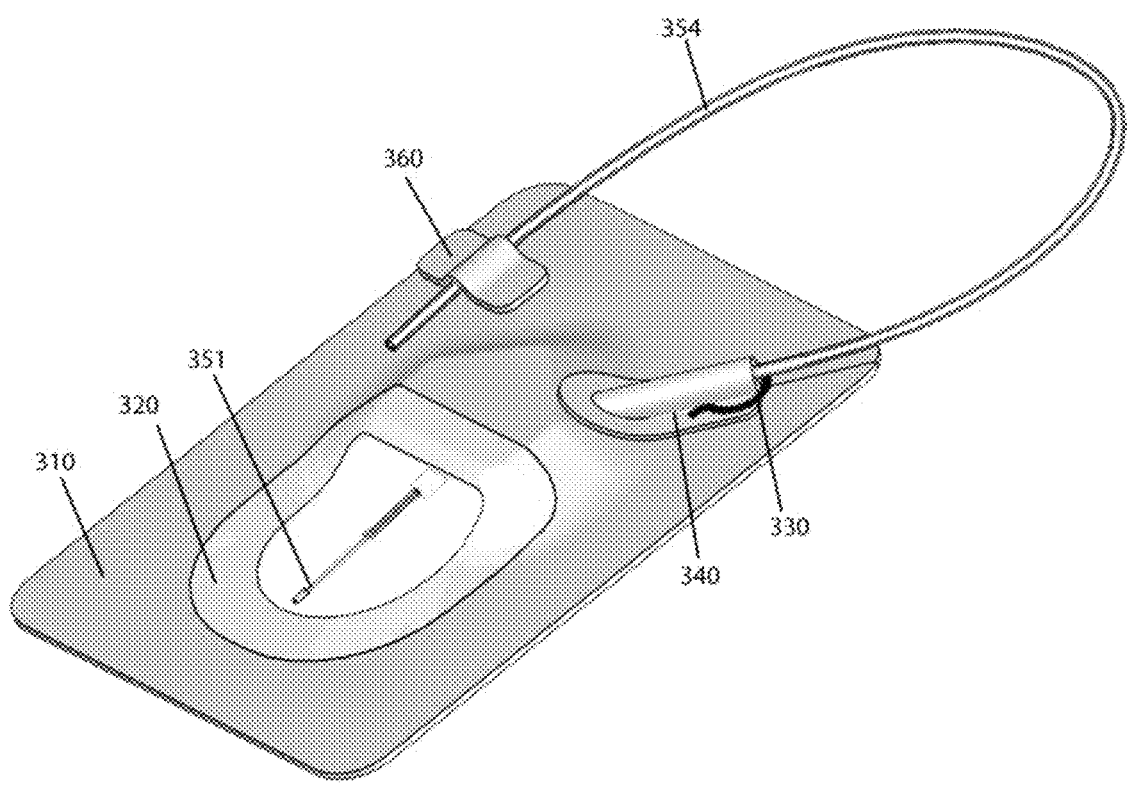
Figure 3J:
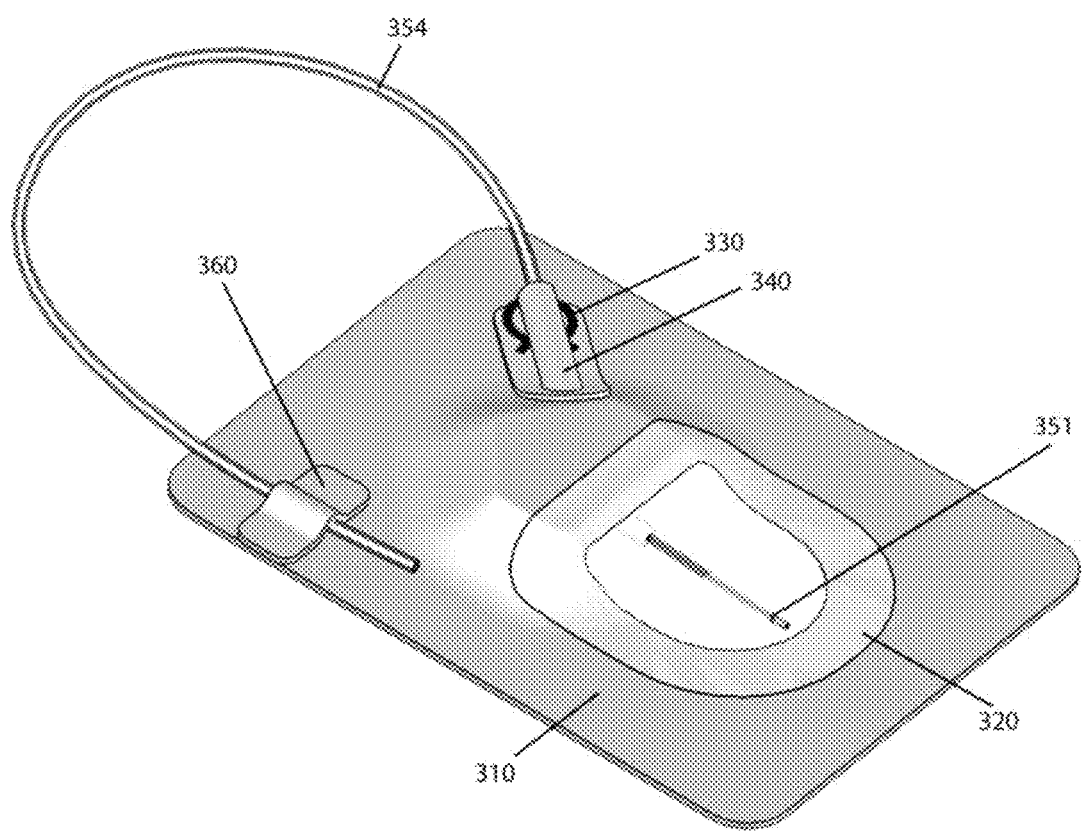
Figure 3K:
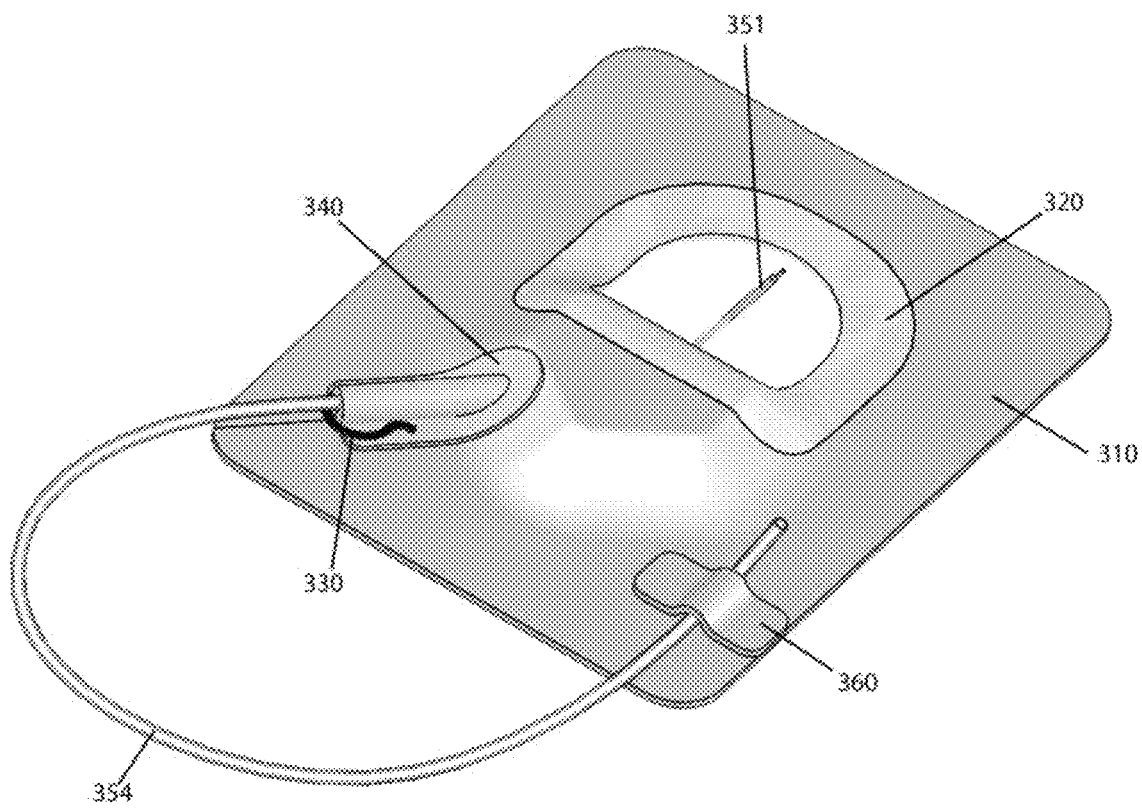
Figure 3L:
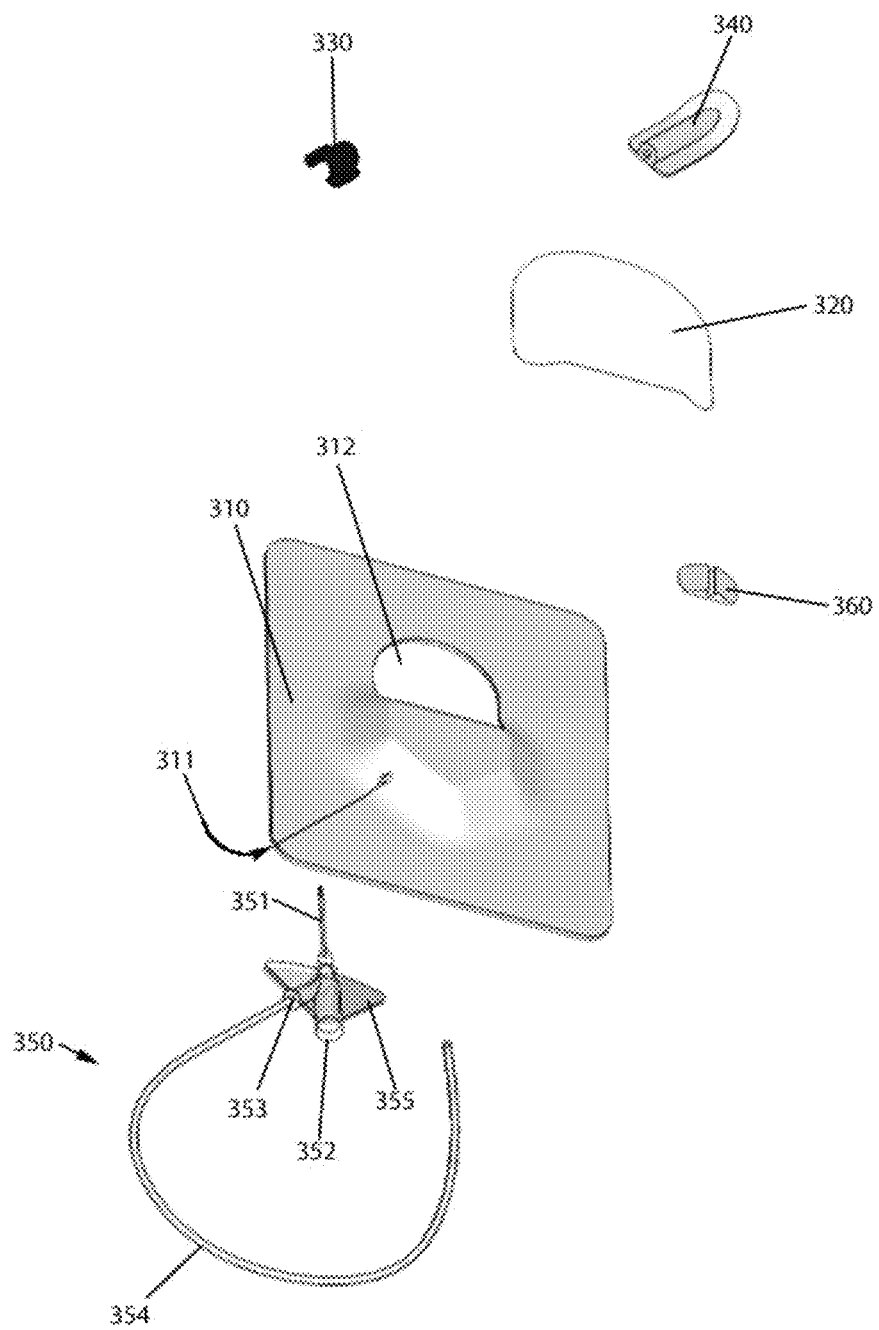
Figure 3M:
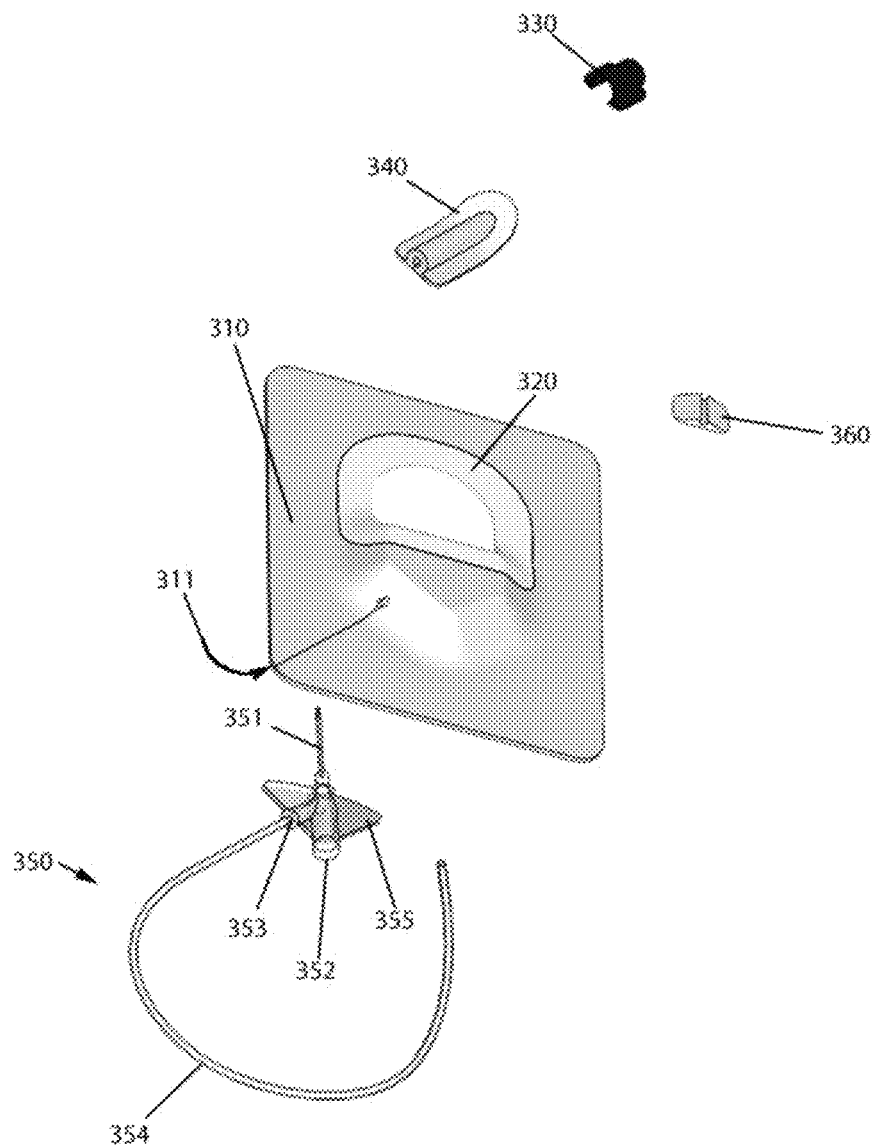
Figure 3N:
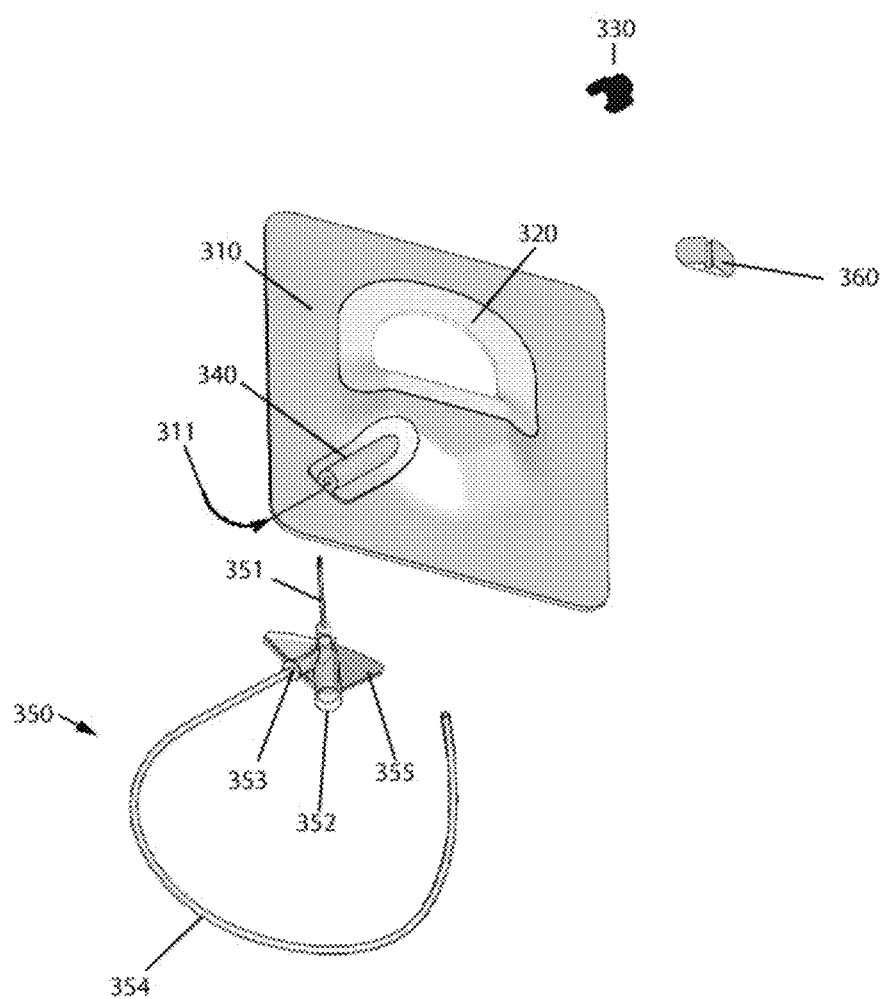
Figure 30:
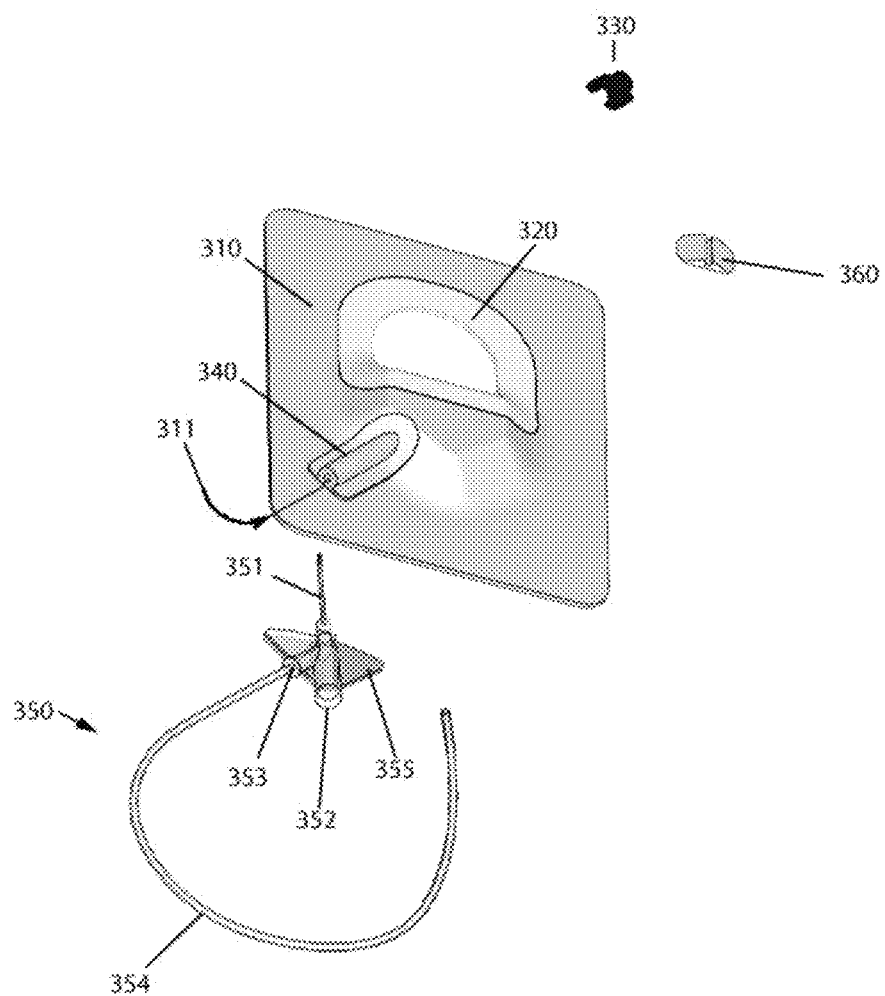
Figure 3P:
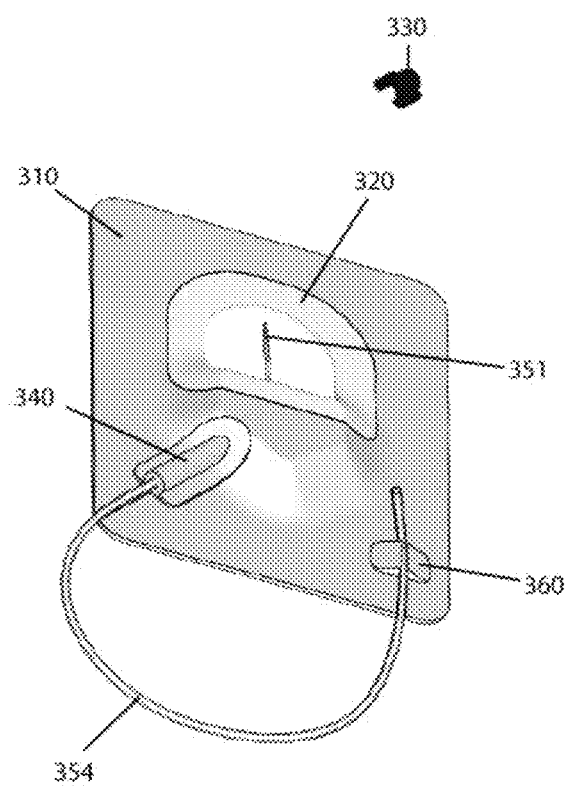
Figure 3Q:
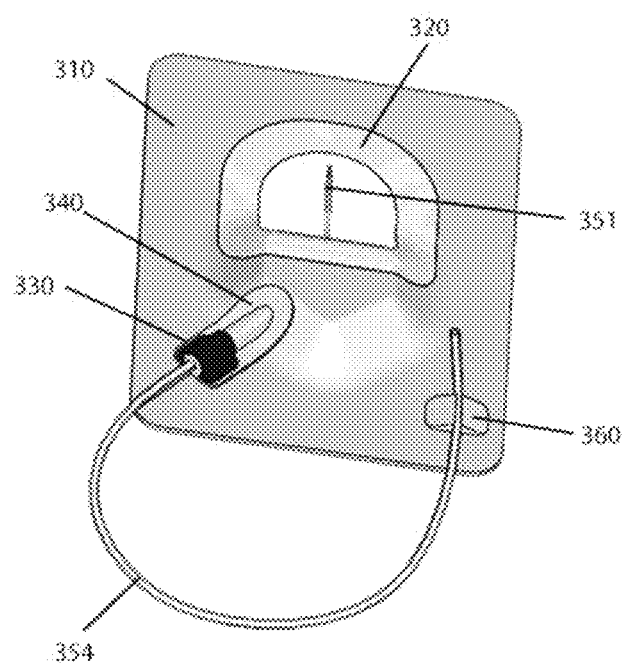
Figure 3R:
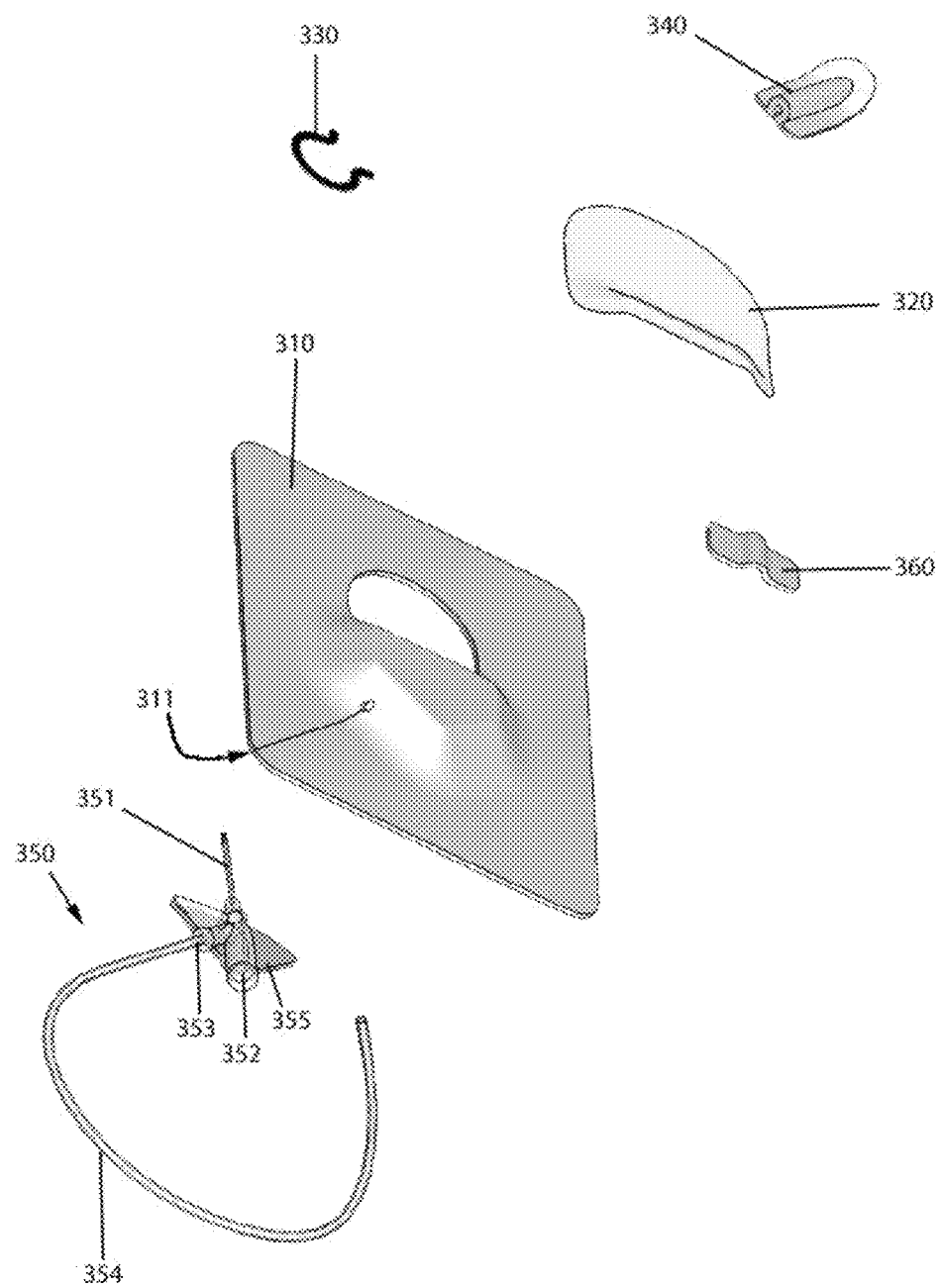

FIGS. 3A-3R illustrate various example sterile dressings 300 according to embodiments disclosed herein. As shown in FIG. 3A, the dressing 300 can generally include a hydrocolloid adhesive 310 that can secure and seal around a catheter 350 (shown in FIG. 3D). The hydrocolloid adhesive 310 can be used to absorb moisture from the patient's skin (not shown) and provide long-term adhesion. For example, adhesive to the skin can last at least 3 days, at least 4 days, at least 5 days, at least 7 days, at least 10 days, or at least 14 days. The adhesive 310 can have a window 312 (shown in FIG. 3L) and a slit 311. A clear, breathable, thin film 320 can be placed on top of adhesive 310 covering the window 312. The adhesive 310 can be configured to conform to and secure the catheter system 350. The catheter system 350 can be any suitable catheter system known in the art, for example a BD Nexiva™ catheter system. A tubing seal 340 can be mounted or attached to the adhesive 310. The tubing seal 340 can be attached using any suitable techniques known in the art. For example, the tubing seal 340 can be permanently affixed to the adhesive 310. The tubing seal 340 can be flexible and/or rigid. In some embodiments, the tubing seal 340 can be made from rubber (e.g., silicone rubber), PVC, polyurethane, or another equivalent. A sealing clip 330 (shown in FIG. 3R) or a cap 330 (shown in FIG. 3P) can further secure the tubing 354 within the tubing seal 340. An adhesive tape 360 (shown in FIG. 3B) or an extension tubing side-arm 360 (FIG. 3A) can further secure the extension tubing 354 on the adhesive 310.

FIG. 3A illustrates a top perspective of view of single-piece (one-piece) sterile sealing and securing dressing 300. As shown in FIG. 3B, the dressing 300 can include a reservoir 388 for holding one or more items. For example, the reservoir can be an antimicrobial agent reservoir agent that holds an antimicrobial agent, such as a chlorhexidine gluconate (CHG) or other antimicrobial agent. The contents of the reservoir 388 can be released into a sterile chamber 387 by any suitable technique known in the art, e.g., by applying finger pressure. The antimicrobial agent, upon release, can reach the sterile chamber 387 though a channel that connects the reservoir 388 to the chamber.

The dressing 300 can also include an alternative ancillary anchor for the extension tubing side-arm to minimize disruptive forces placed at the extension tubing exit point from the sealing flange. In FIG. 3C, which illustrates a top perspective view of the dressing, a catheter 350 is shown in place below the mated and mounted sterile sealing and securing dressing 300. FIG. 3D, which illustrates a below/beneath perspective view of the dressing, illustrates a catheter 350 in place beneath the sterile sealing and securing dressing 300. The extension tubing 354 side arm 353 can exit the dressing 310 (from below) and run along the outside of the dressing after passing through the sealing flange 340. The dressing material 310 can be molded/shaped to form fit to the underlying catheter to optimize stabilization and securement and to minimize dead-space. In this embodiment, the adhesive plate 310 adheres to at least part of the catheter hub and/or stabilization wings 355.

FIG. 3F is a top perspective view of a sealing support clip 330 of that can exert clamping force from above. FIG. 3G is a top perspective showing a sealing support clip 330 of a design that can exert clamping force from beneath the extension tubing exit point. FIG. 3H is another top perspective showing a segment of adhesive 360 that can be used to stabilize the extension tubing 360 side arm at a remote point from the sealing flange exit point. In this example, the adhesive stabilization strip 360 is shown attached to the main adhesive plate. Alternatively or additionally, this stabilizing adhesive strip can be attached to the skin at a site separate from the main adhesive plate 310 to ensure that disruptive forces cannot affect the integrity of the adhesive plate 310.

FIG. 3I is an alternative top perspective view that illustrates the alternative sealing support clip 330 embodiment in addition to the ancillary stabilizing strip 360. FIGS. 3J-3K are other top perspective example views of the dressing 300.

FIG. 3L illustrates some of the components that can be incorporated into the one-piece integrated sterile sealing and securing dressing 300. Also shown is a catheter 350 (e.g., BD Nexiva™ peripheral IV), with which the sterile sealing and securing dressing 300 can be configured to specifically mate.

FIG. 3M also illustrates some of the separate components of the one-piece integrated sterile sealing and securing dressing 300. As shown in FIG. 3M, the clear (e.g., transparent) film window 320 can be attached to the main adhesive plate 310.

FIG. 3N also illustrates some the separate components of the one-piece integrated sterile sealing and securing dressing 300, with extension tubing 354 external circumferential sealing flange attached to the main adhesive plate. FIG. 3O illustrates an example of a complete one-piece integrated sterile sealing and securing dressing 300, in which the extension ancillary extension tubing support clip 360 can be attached to the main adhesive dressing plate 310. As illustrated in FIG. 3P, the completed dressing 300 can be fully mated to an inserted catheter 350 (e.g., BD Nexiva™ catheter). Further, as illustrated in FIG. 3Q, the mated catheter 350 and dressing complex 300 can be held in place or secured using external circumferential sealing flange support clip 330. FIG. 3R illustrates some of the separate components of a sterile sealing and securing dressing 300. As shown in FIG. 3R, the dressing can include a lateral/below-the tubing external sealing flange support clip 330 and an extension tubing adhesive supplemental stabilization strip 360.

Figure 4A:
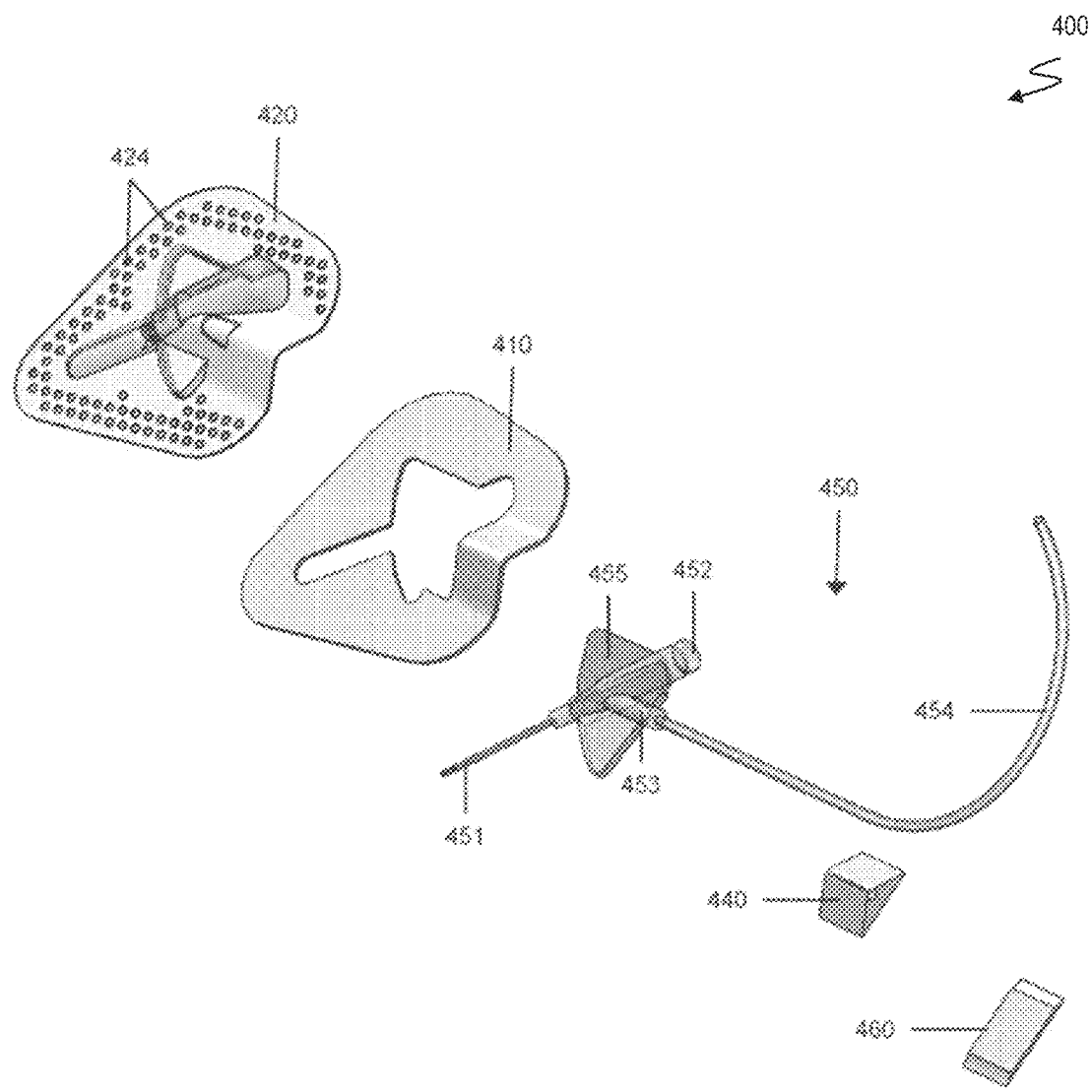
FIGS. 4A-4Q illustrate various views of an embodiment of a sterile sealing and securing dressing according to some embodiments disclosed herein.
Figure 4B:
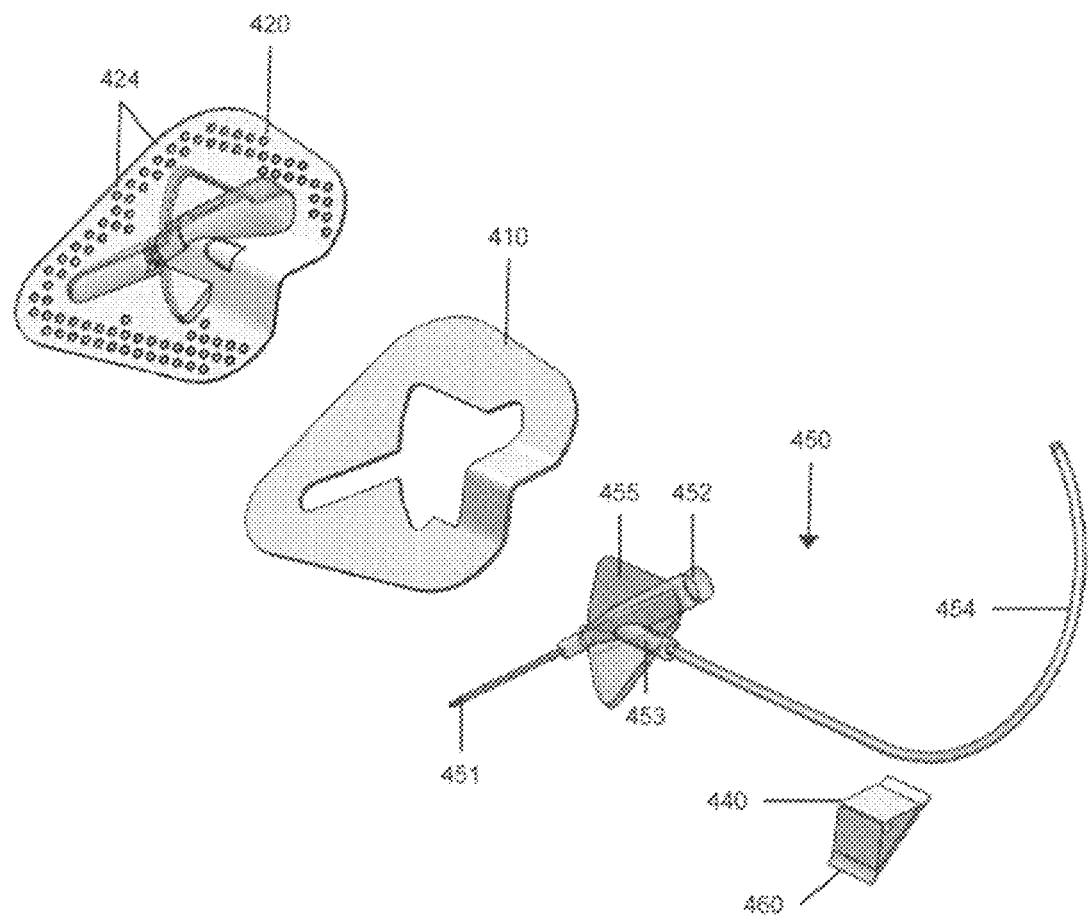
Figure 4C:
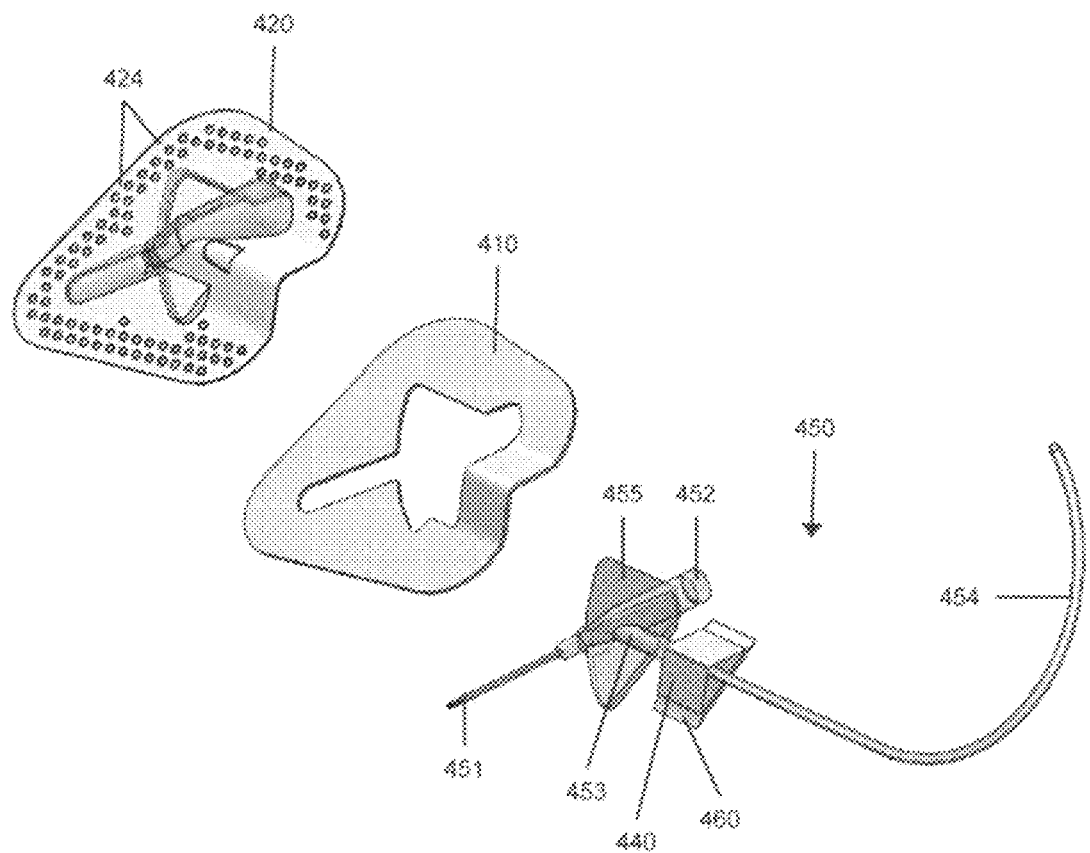
Figure 4D:
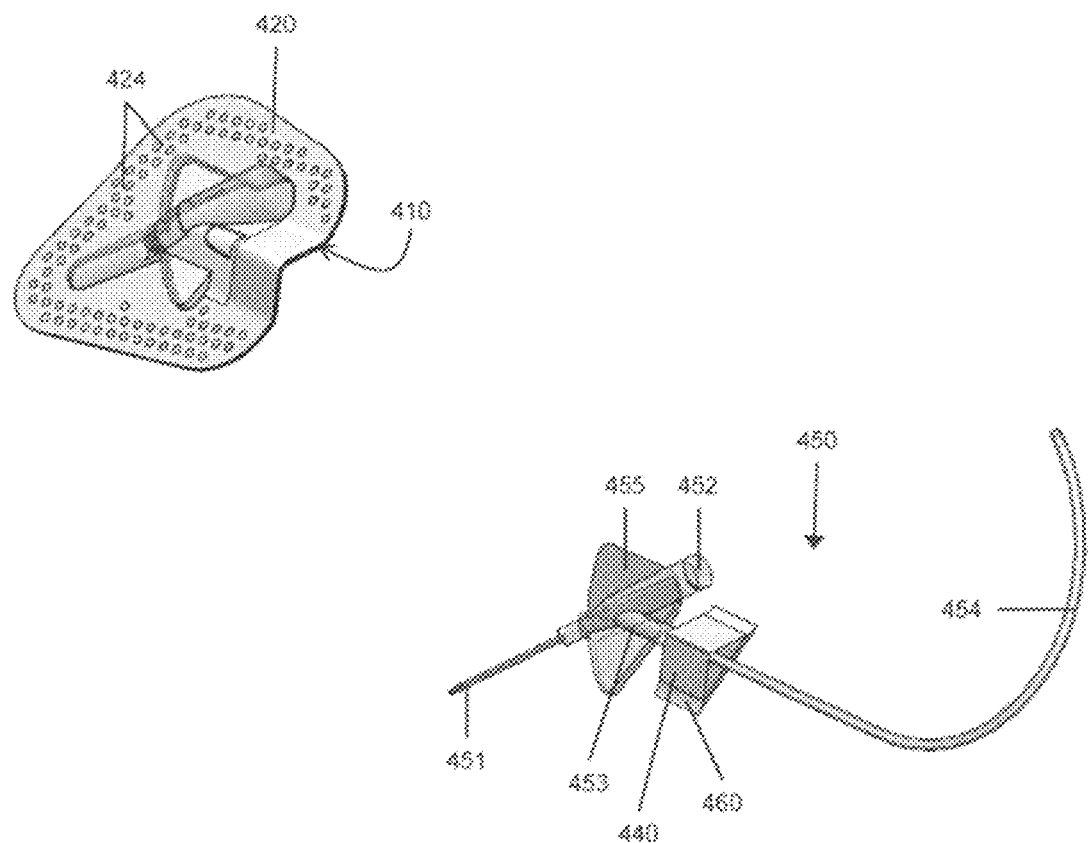
Figure 4E:
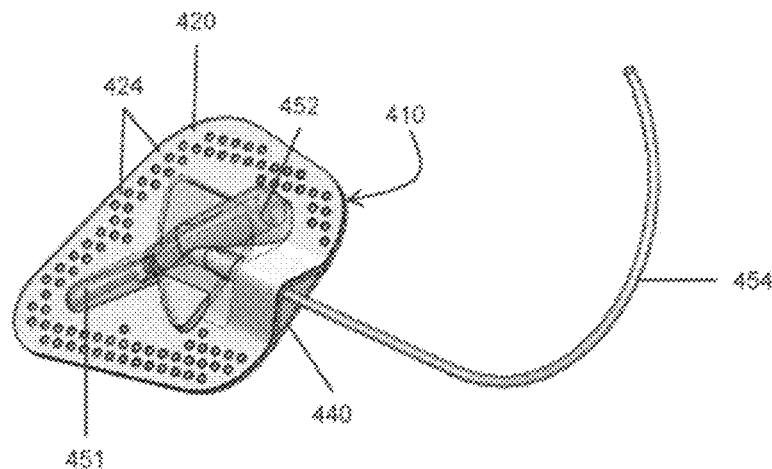
Figure 4F:
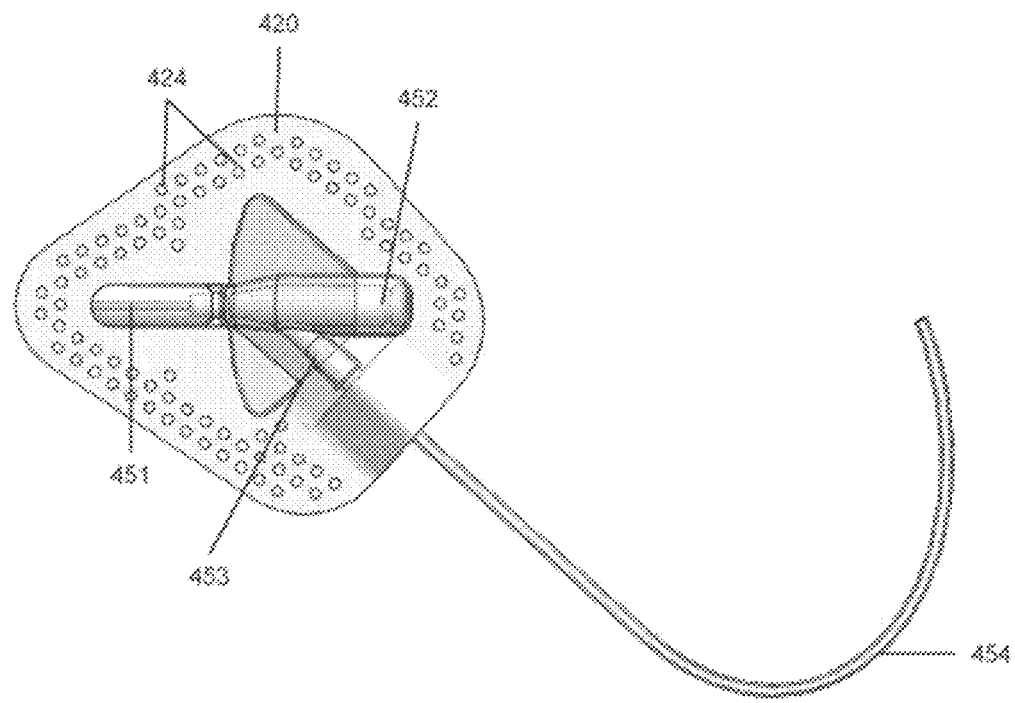
Figure 4G:
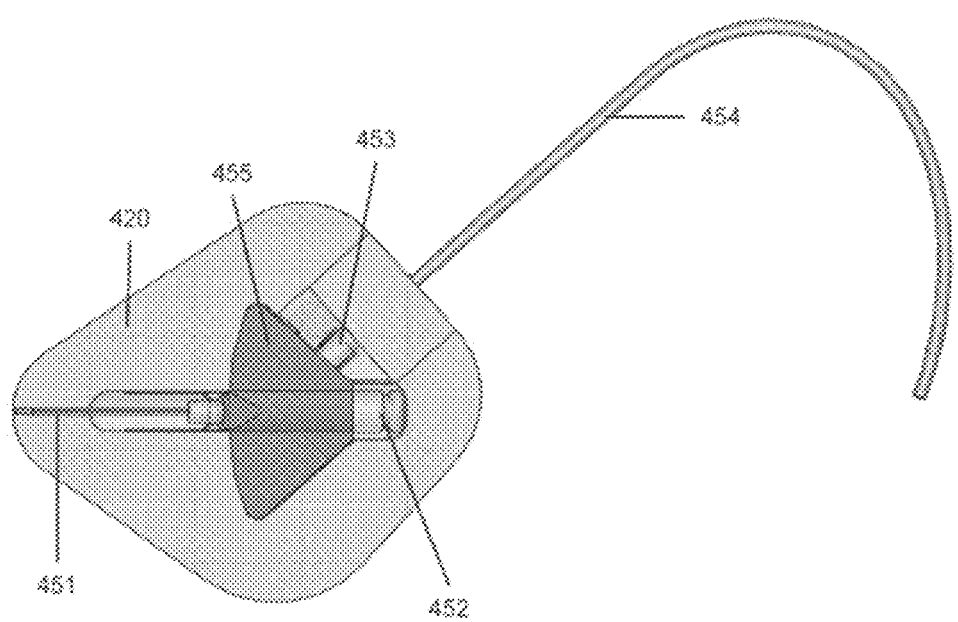
Figure 4H:
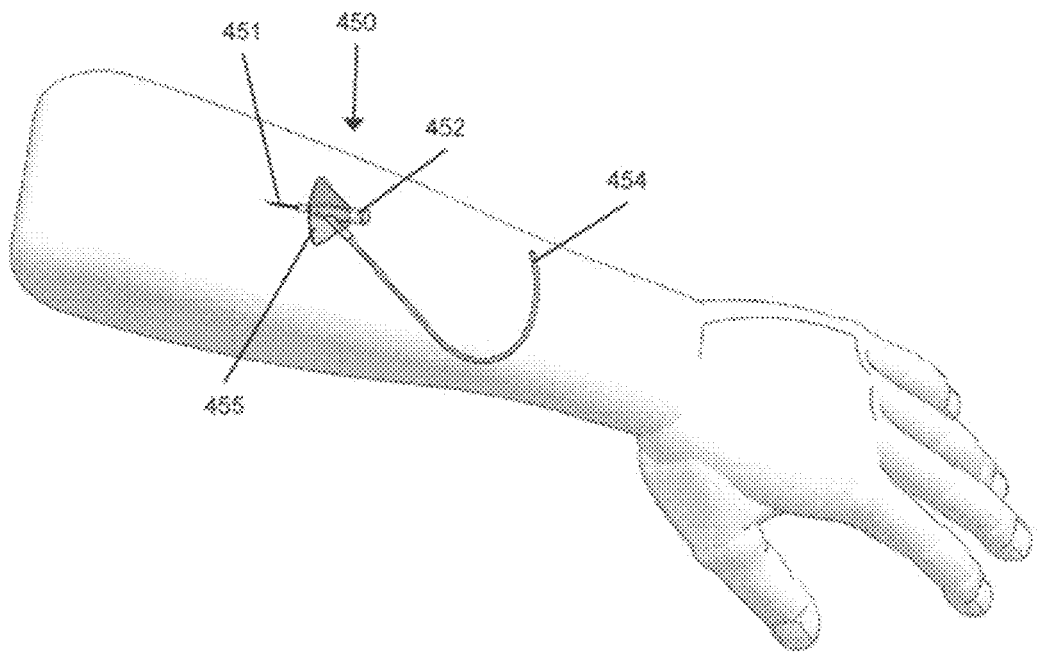
Figure 41:
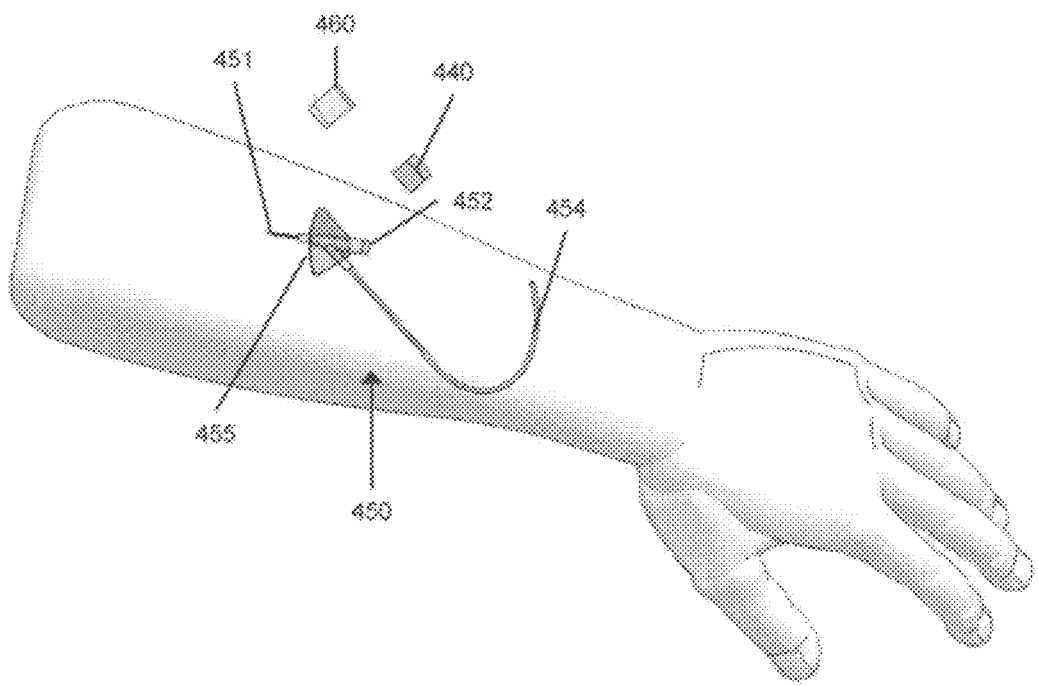
Figure 4J:
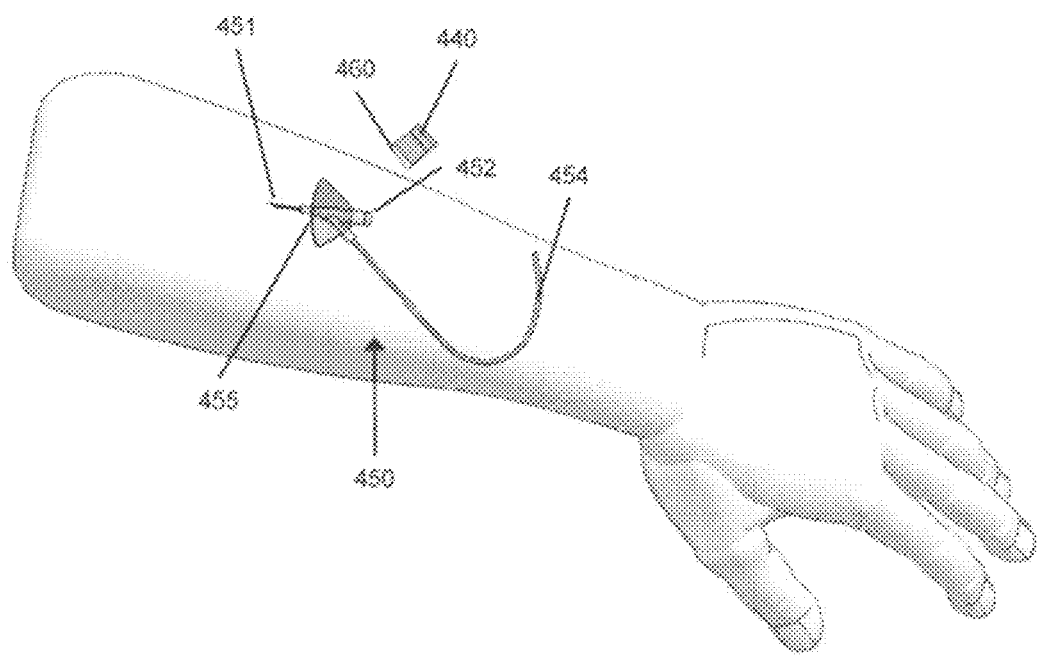
Figure 4K:
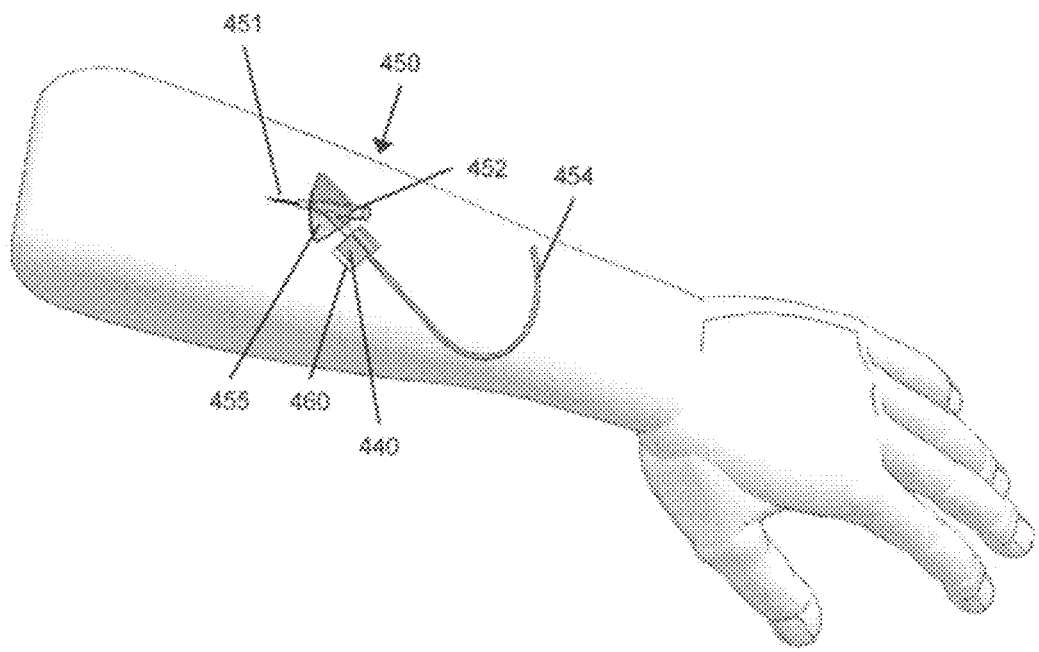
Figure 4L:
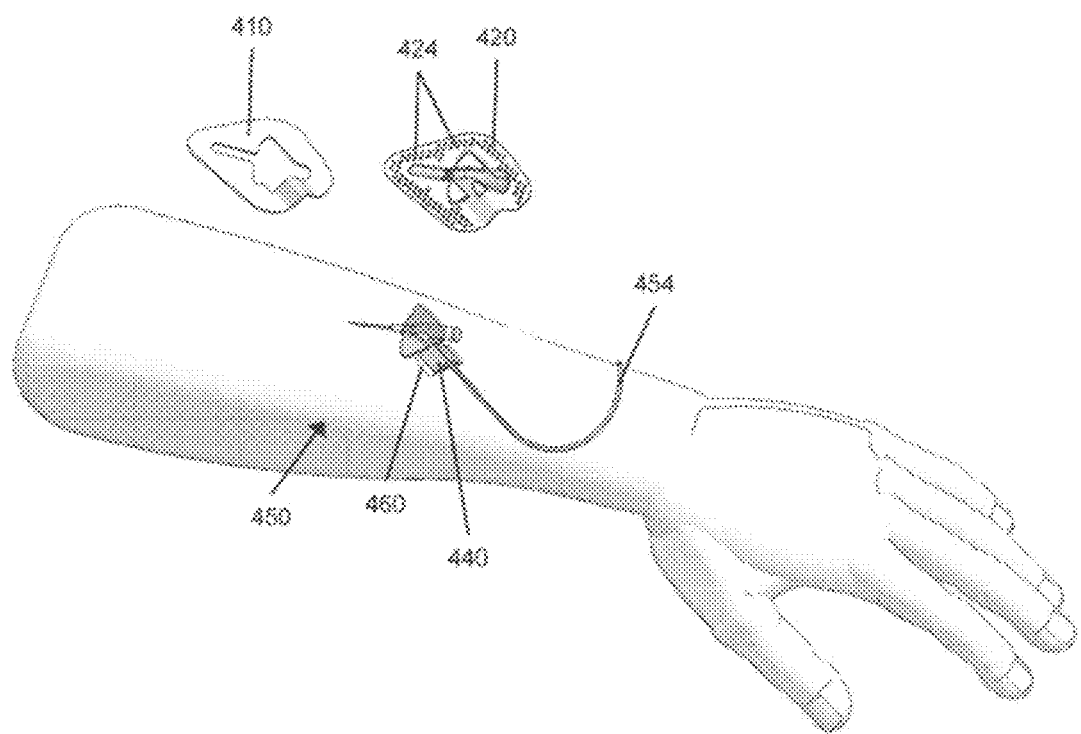
Figure 4M:
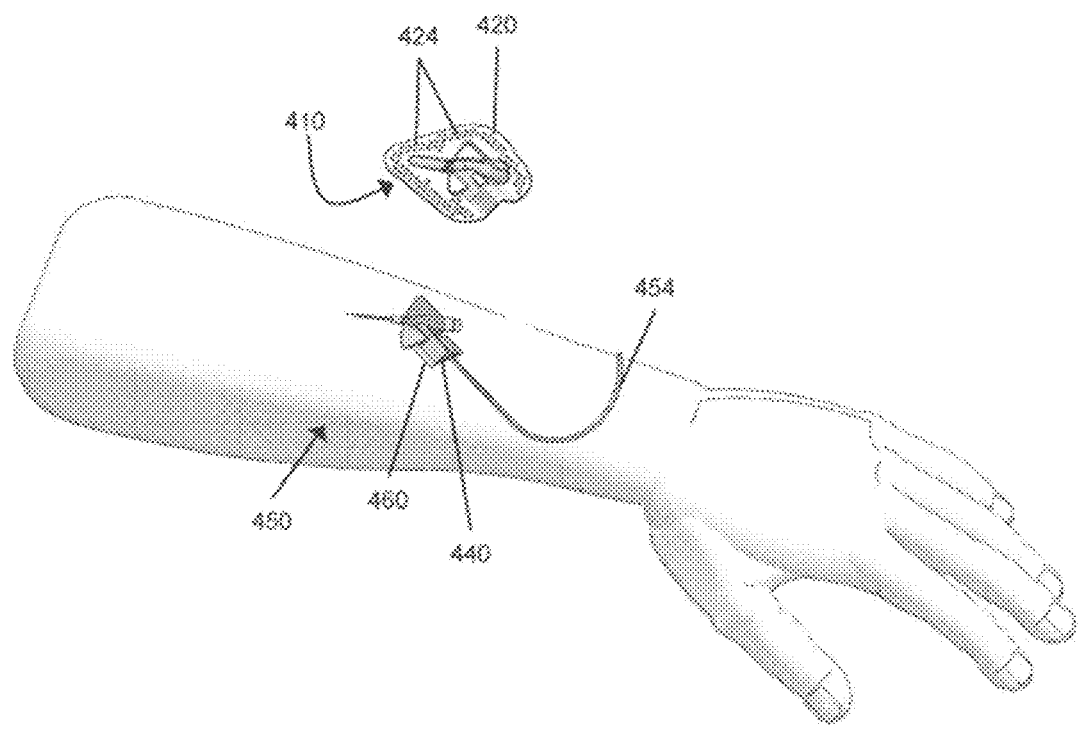
Figure 4N:
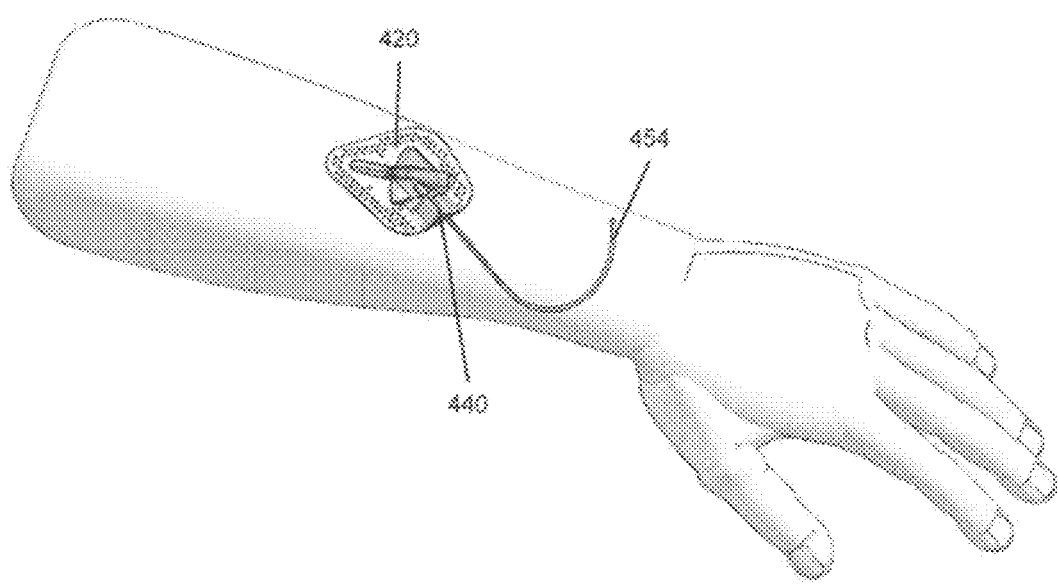
Figure 4O:
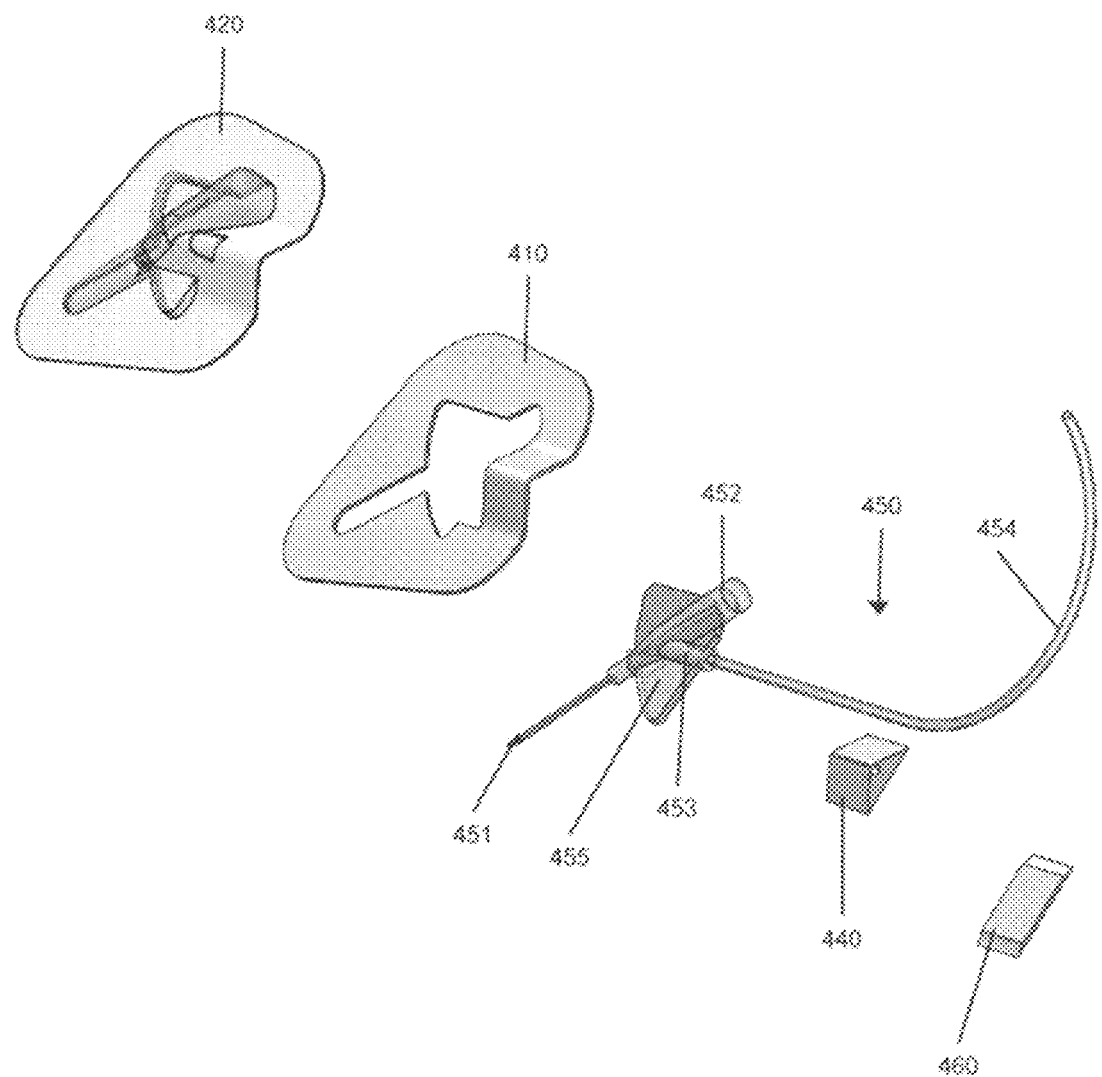
Figure 4P:
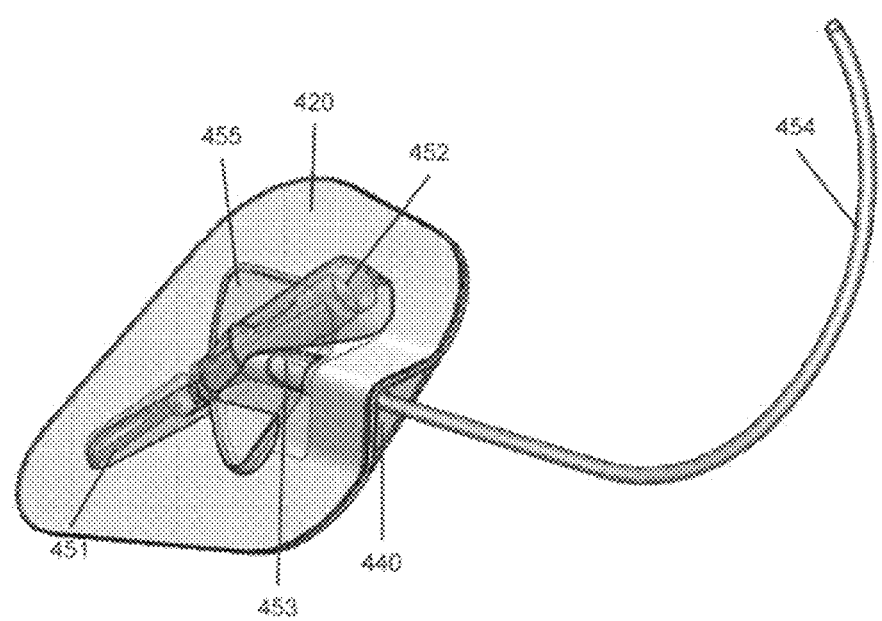
Figure 4Q:
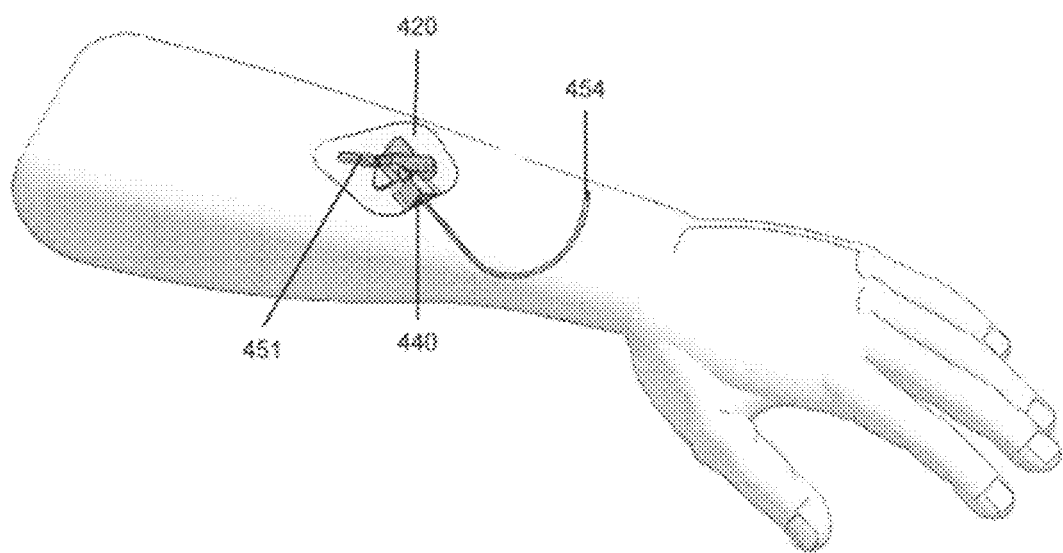
Figure 5A:
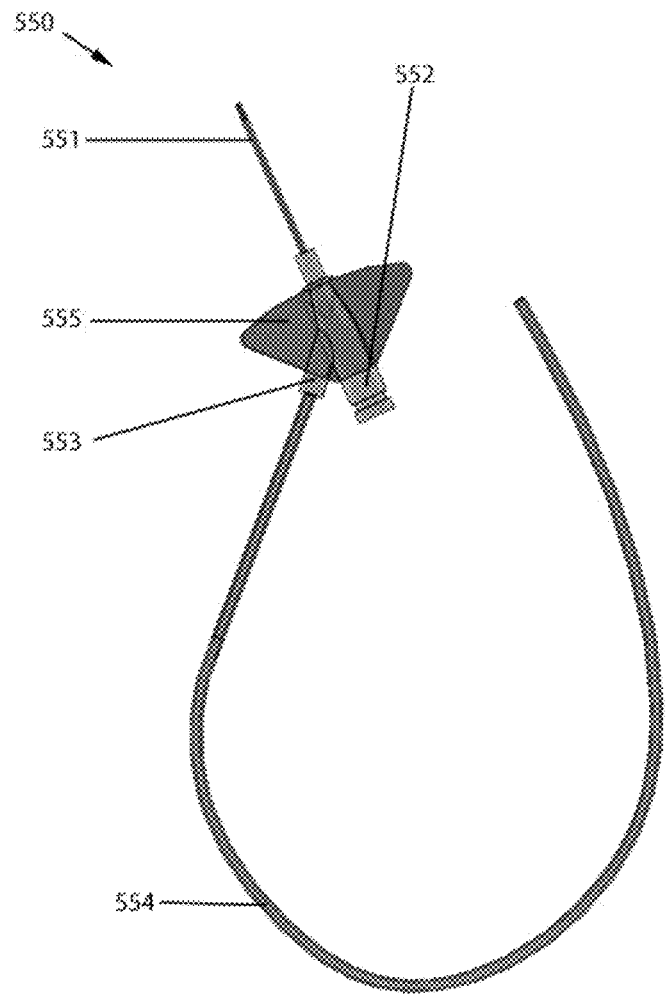
FIGS. 5A-5E illustrate various views of another embodiment of a sterile sealing and securing dressing according to some embodiments disclosed herein.
Figure 5B:
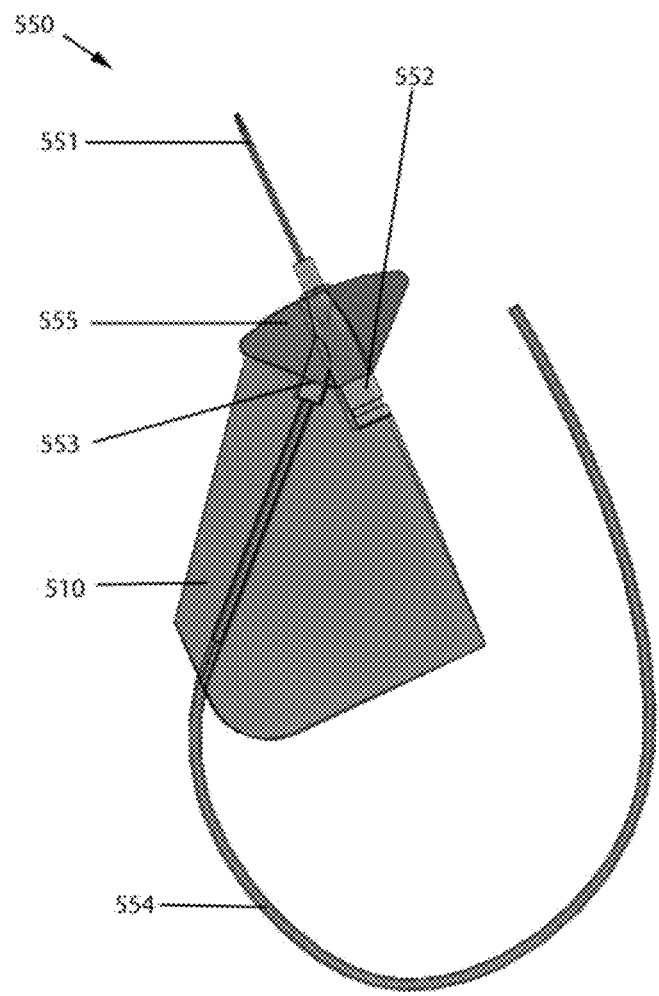
Figure 5C:
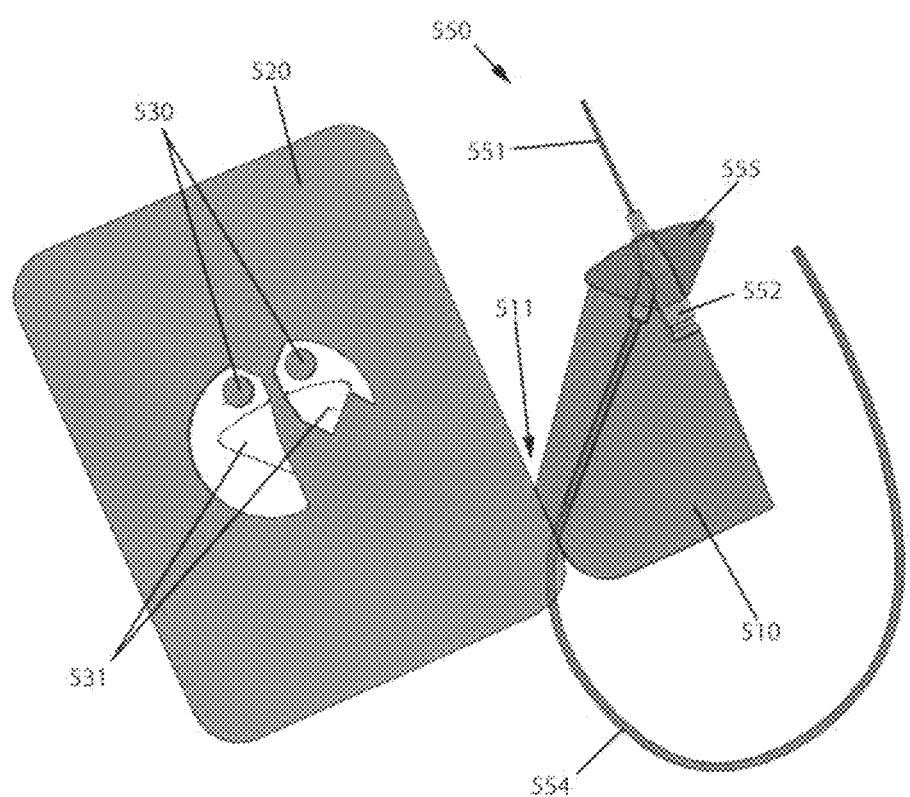
Figure 5D:
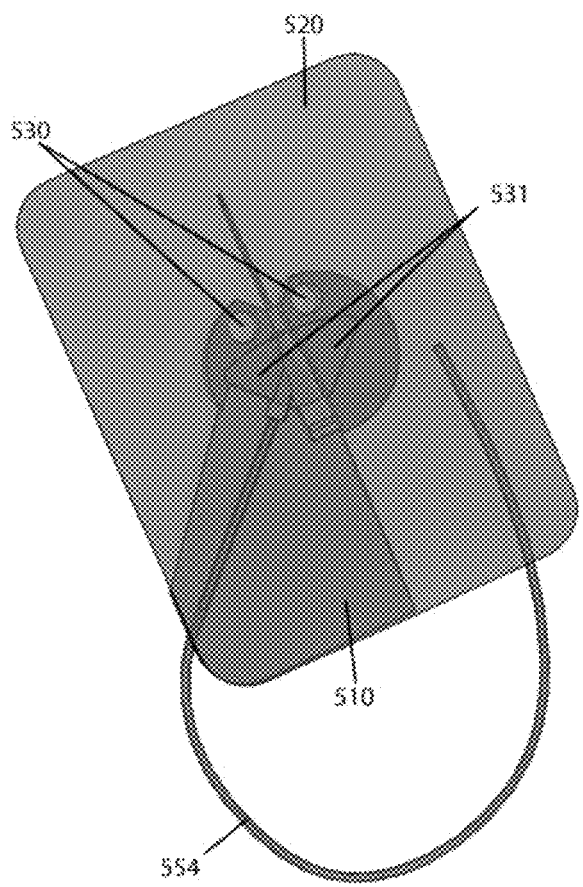
Figure 5E:
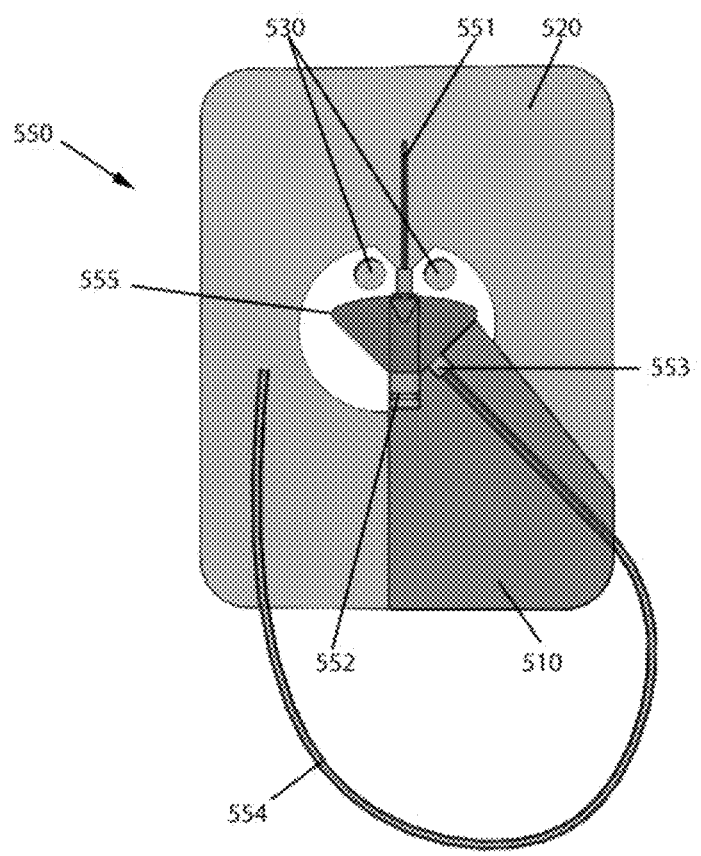
Figure 6A:
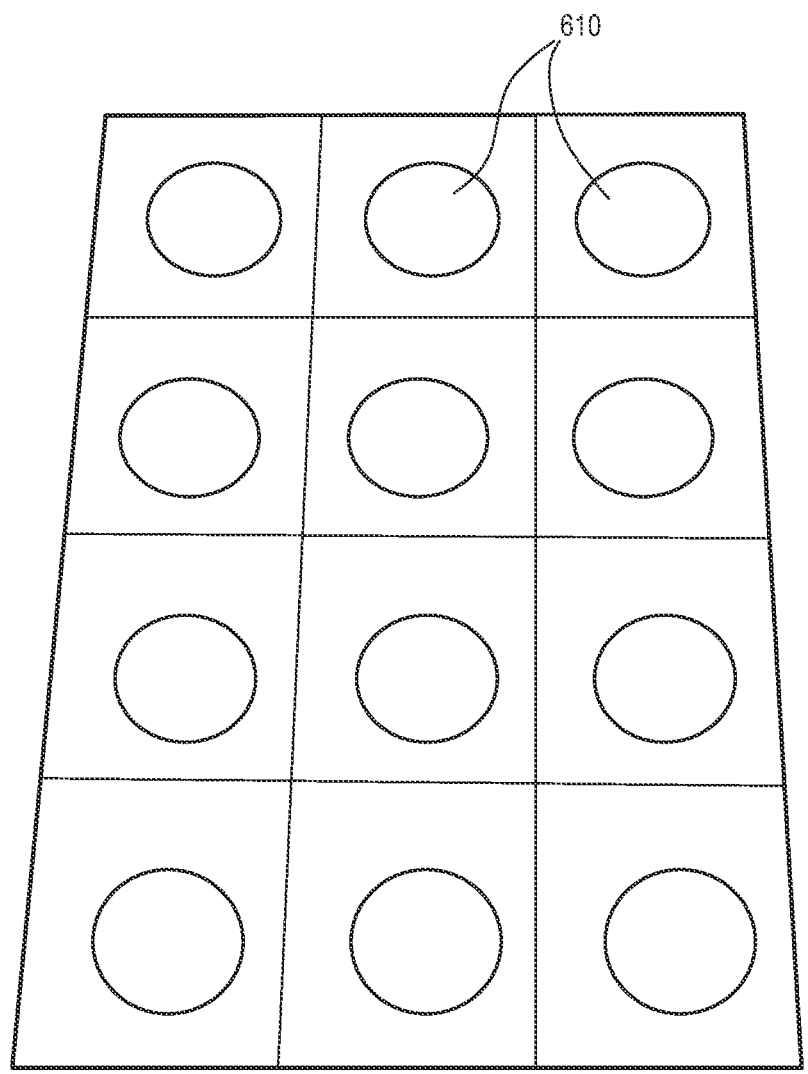
FIGS. 6A-6E illustrate a sheet for use in securing a catheter for attachment using a dressing according to some embodiments disclosed herein.
Figure 6B:
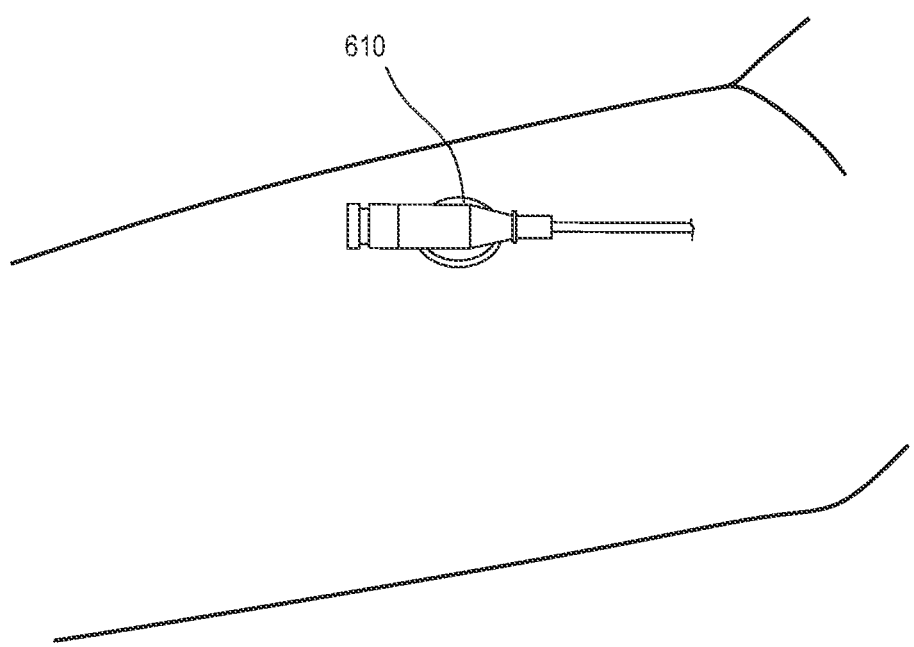
Figure 6C:
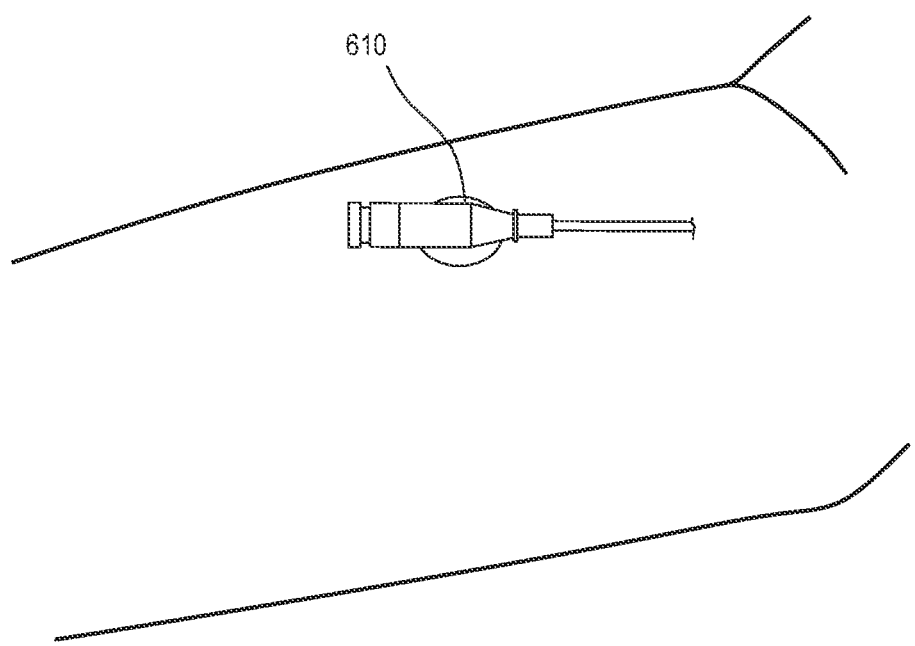
Figure 6D:
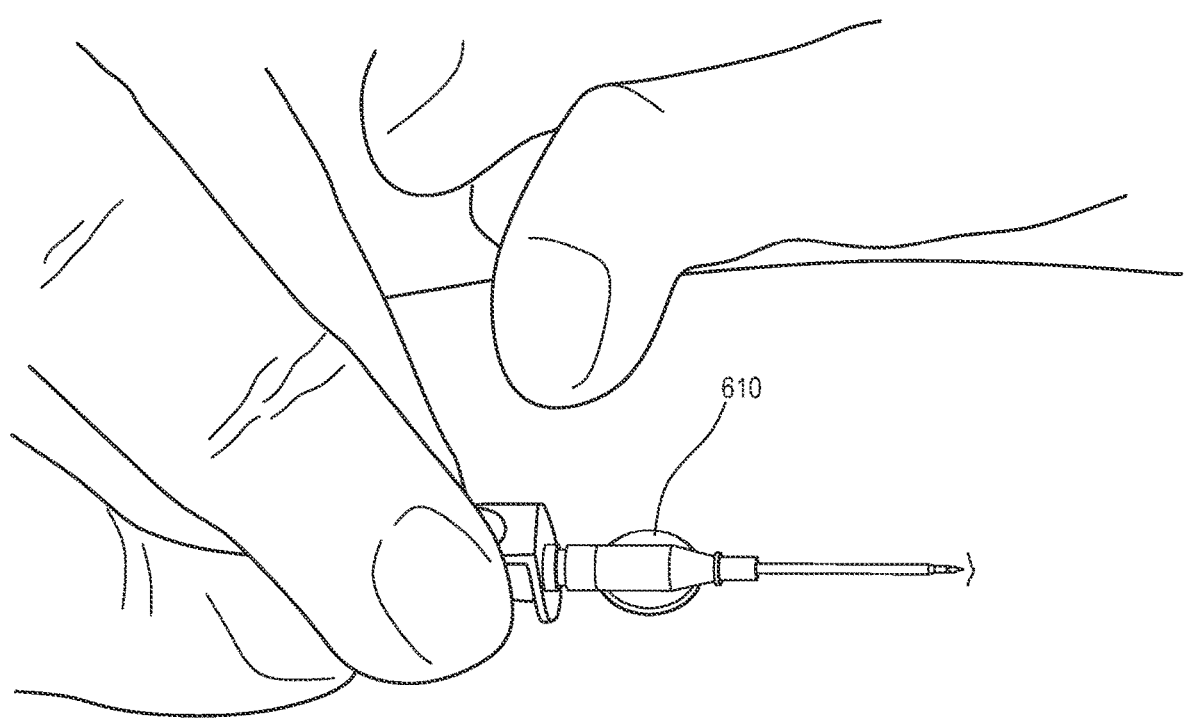
Figure 6E:
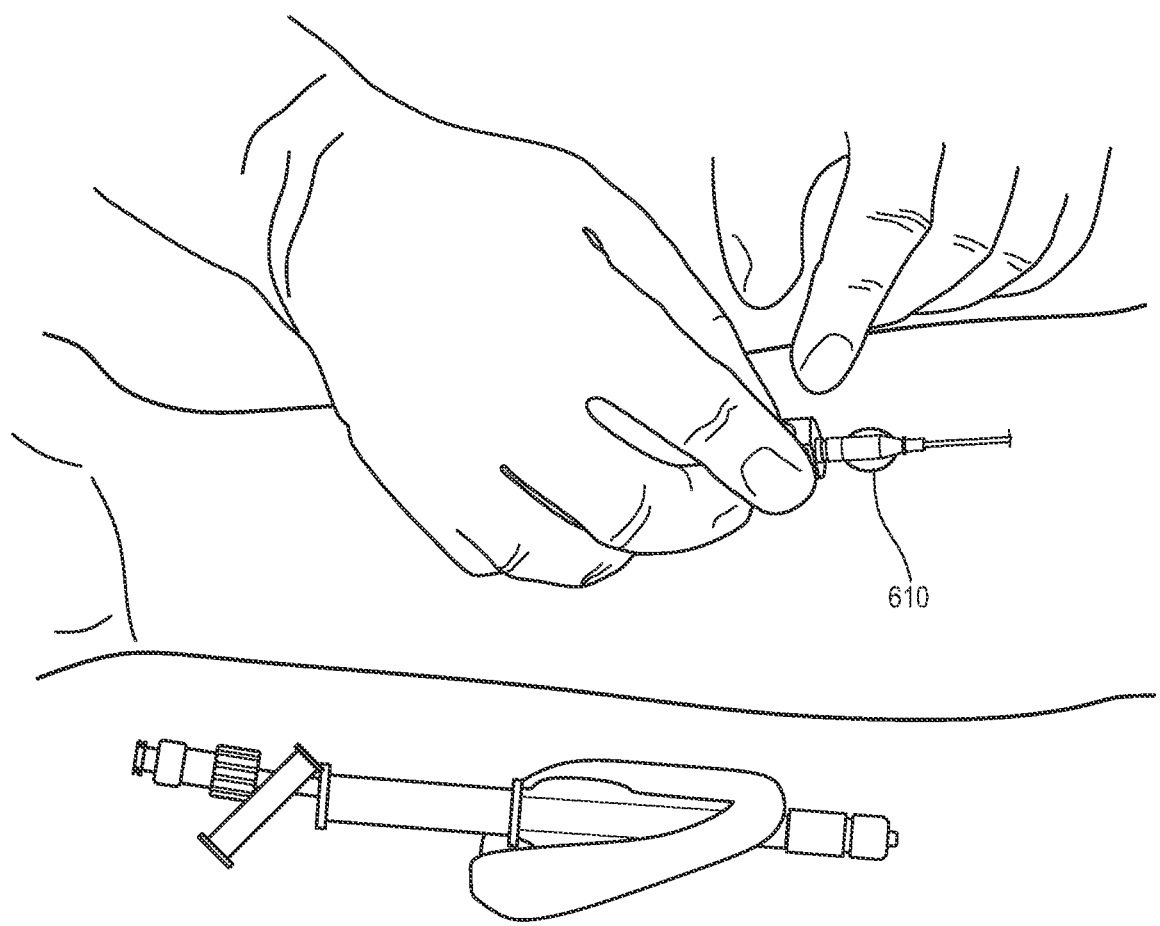

FIGS. 4A-4Q illustrate various views of another embodiment of a sterile sealing and securing dressing 400. The dressing 400 is configured to receive a catheter system 450. The dressing 400 can include a flexible adhesive dressing cover 420. The cover 420 can cover, secure, and/or seal the catheter 450. One or more holes 424 can be formed in the cover 420 to improve breathability.

Further, a double-sided adhesive tape 410 can be used to adhere to both the bottom of cover 420 and to a patient's skin. The tube seal 440 can be made from a flexible rubber or other polymer (e.g., silicone rubber, PVC, polyurethane, etc.) and can be configured to receive a portion of the extension tubing 454 from the catheter system 450. A double-sided adhesive tape 460 can secure the tube seal 440 to the patient's skin. The tube seal 440 can be configured to be received within a portion of the cover 420 and adhesive 410.

FIGS. 5A-5E illustrate various views of another embodiment of a sterile sealing and securing dressing 500. A catheter system 550 (e.g., a BD Nexiva™ catheter system) can be mated to a flexible tube seal and securement device 510. The device 510 can have an adhesive layer that is used to attach the device 510 to a patient's skin. The securement device 510 can be connected to a thin, clear breathable film 520. The securement features 531 can be attached to the film 510 using any suitable techniques known in the art. Further, the securement features 531 can be made from any suitable material available in the art. For example, the securement features 531 can be made from foam, rubber, or any rigid materials and are attached to the film 520. One or more antiseptic wells 530 can receive and hold antiseptic foams, gels, or sacs (not shown, e.g., CHG, IPA). The sacs can be punctured to release an antiseptic agent.

FIGS. 6A-6E illustrate a sheet, such as a sticky dot sheet 610, that can be configured to securely hold a catheter (e.g., a catheter 151, 251, 351, 451) in place, while the dressing is being attached and/or when extra securement of the catheter is required. The sticky dots or circles 610 can be placed under the catheter hub. A sticky dot 610 can include an antiseptic agent and/or a protective backing that can be pulled off before or after placement. The backing can be made from any suitable material available in the art. For example, the backing can be plastic, wax paper, or any non-sticky substrate that can be used to prevent and/or protect the adhesive from sticking until it is ready for use and attachment. The backing can be long and narrow. Further, the backing can be folded over to aid placement and peeling off from a distance.

Figure 7A:
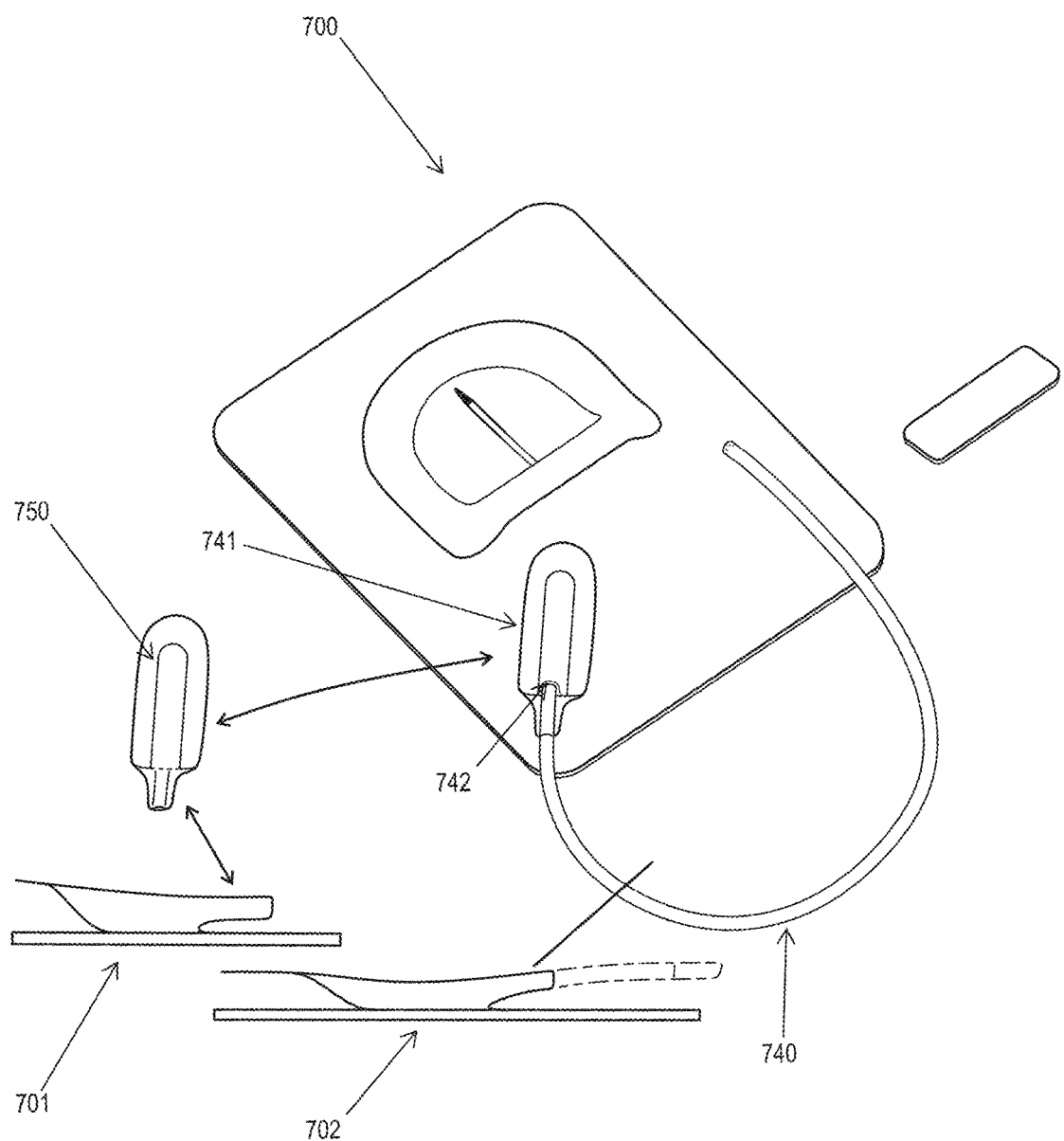
FIGS. 7A-7E illustrate examples of sterile dressings according to some embodiments disclosed herein.

FIG. 7A illustrates an example sterile dressings 700 according to some embodiments disclosed herein. As illustrated in FIG. 7A, a sealing flange 741 of an extension tubing 740 can have a flexible extension 750 that protrudes from the sealing flange 741 to provide additional coverage of an extension tubing (of a catheter) that can run through the flange 741. This can provide additional grip and more opportunity to maintain a vigorous seal in the face of disruptive forces placed on the extension tubing 740 during clinical use. This flexible extension 750 can have a posterior slit 742 (for example, similar to the main portion of the flange) through which the tubing 740 can be pushed to enter and then dwell in the central channel of the flange 741. Also shown are two side views of the flange extension 750 relative to the remainder of the dressing, as well as relative to the portion of the extension tubing 740 that is contained within the flange 750.

Figure 7B:
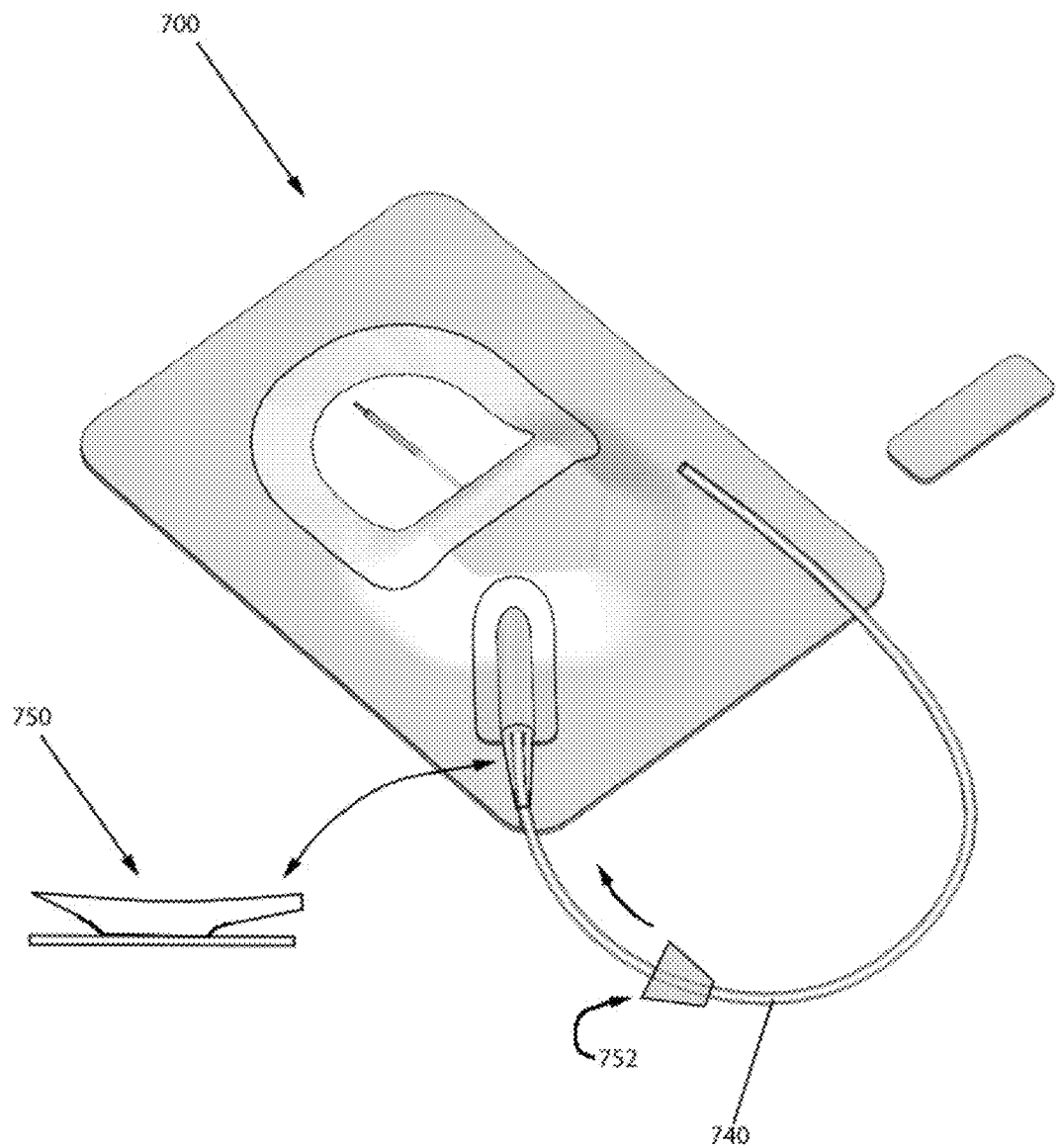

FIG. 7B illustrates a top view of the dressing 700 shown in FIG. 7A. As shown, in addition to the sealing flange extension 750, a collar 752 can be placed around the extension tubing 740. The collar 752 can be configured such that it is slid down around the flange extension 750 to lock the flange into a 360 degrees circumferential sealing position around the extension tubing, after the extension tubing is engaged into the sealing flange central channel This sliding collar 752 can have features that allow for the collar 752 to attach to and/or mate with the main body of the sealing flange 740 and/or dressing 700 to maintain the collar's position relative to the flange (by, for example, bayonet, snap fit, gasket-groove, adhesion, etc.). The collar 752 can be form fitted to the contours of the flange 740 to lock the flange 740 in the fully sealing state.

Figure 7C:
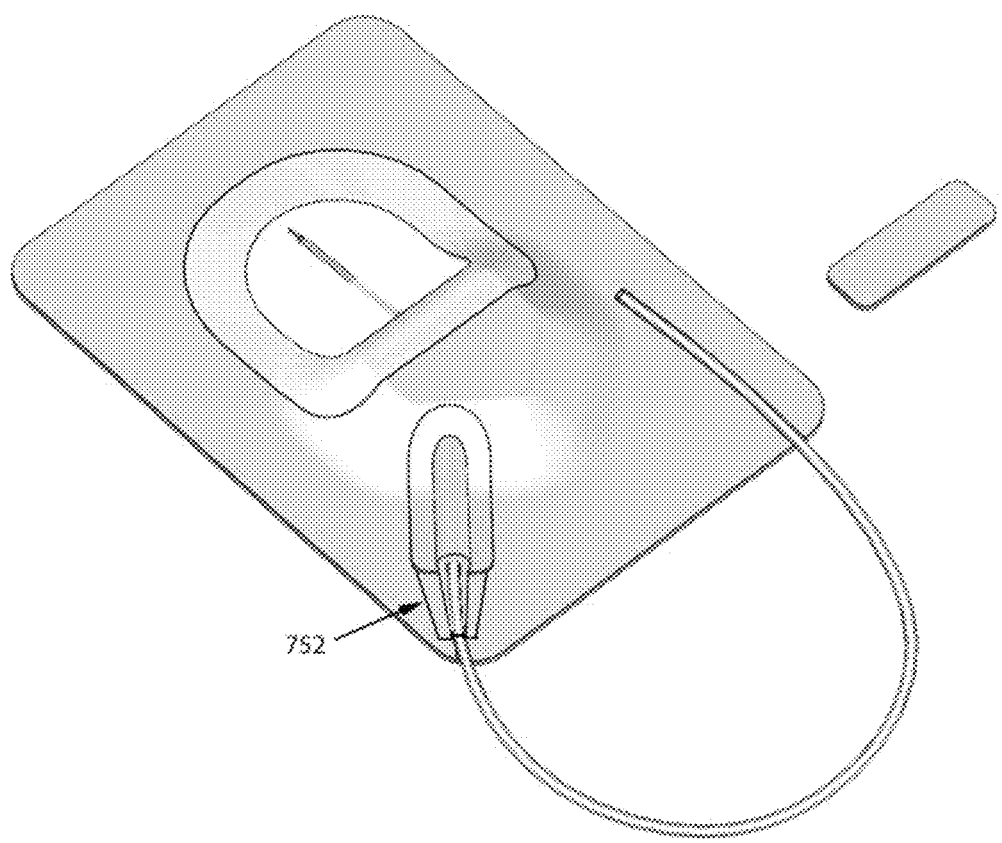

FIG. 7C is another top perspective view of the dressing that illustrates the sliding collar 752 in place, such that the collar 752 supports the sealing flange and its extension into a fully sealed and secured arrangement.

Figure 7D:
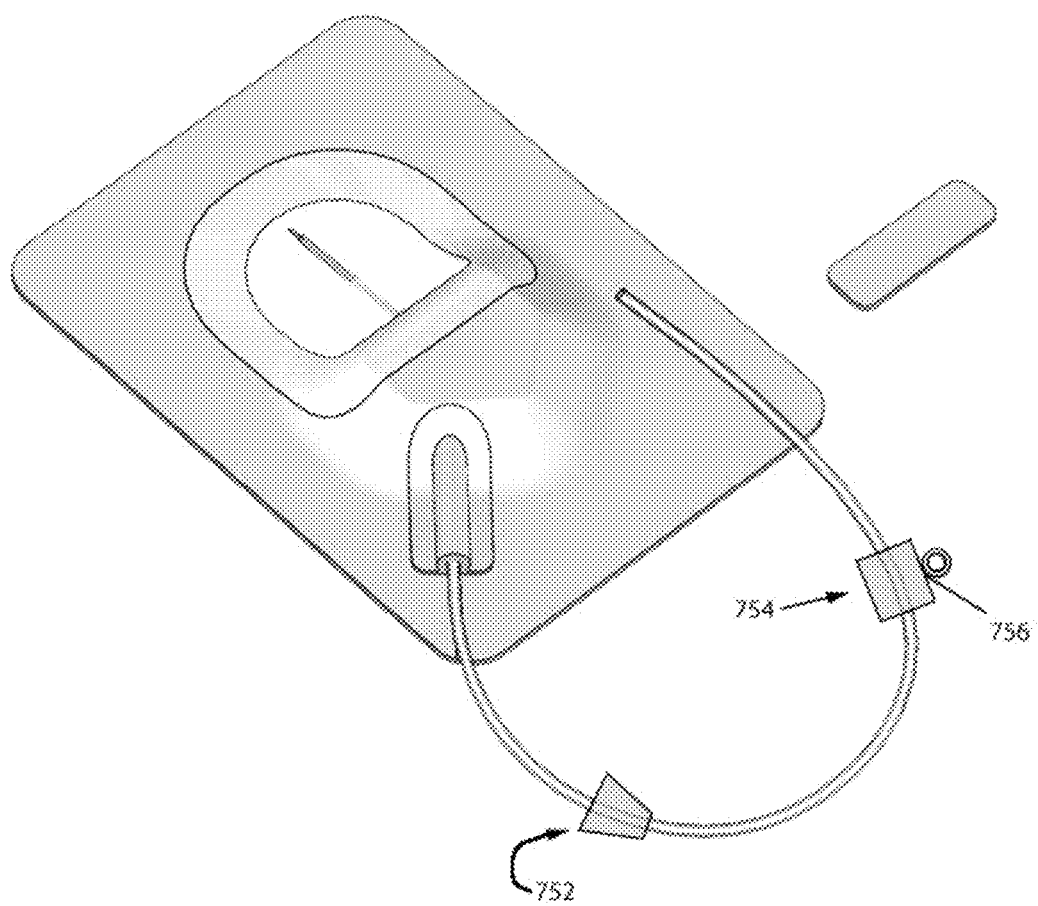

FIG. 7D is yet another top perspective view of the dressing 700 that illustrates the sliding collar 752 around the extension tubing. Also shown, a second sliding collar 754 with a means 756 for attaching this collar 754 to the patient's body can be used at a point separate from the main sterile sealing and securing adhesive dressing, so that forces exerted on the catheter extension tubing during clinical use are primarily transferred to this extension tubing anchor point, and not to the sealing flange of the dressing. The attachment mechanism 756 of the sliding collar 754 can be any suitable attachment means, such as a ring, a clip, or other attachment means by which it connects and/or attaches to the anchor point.

Figure 7E:
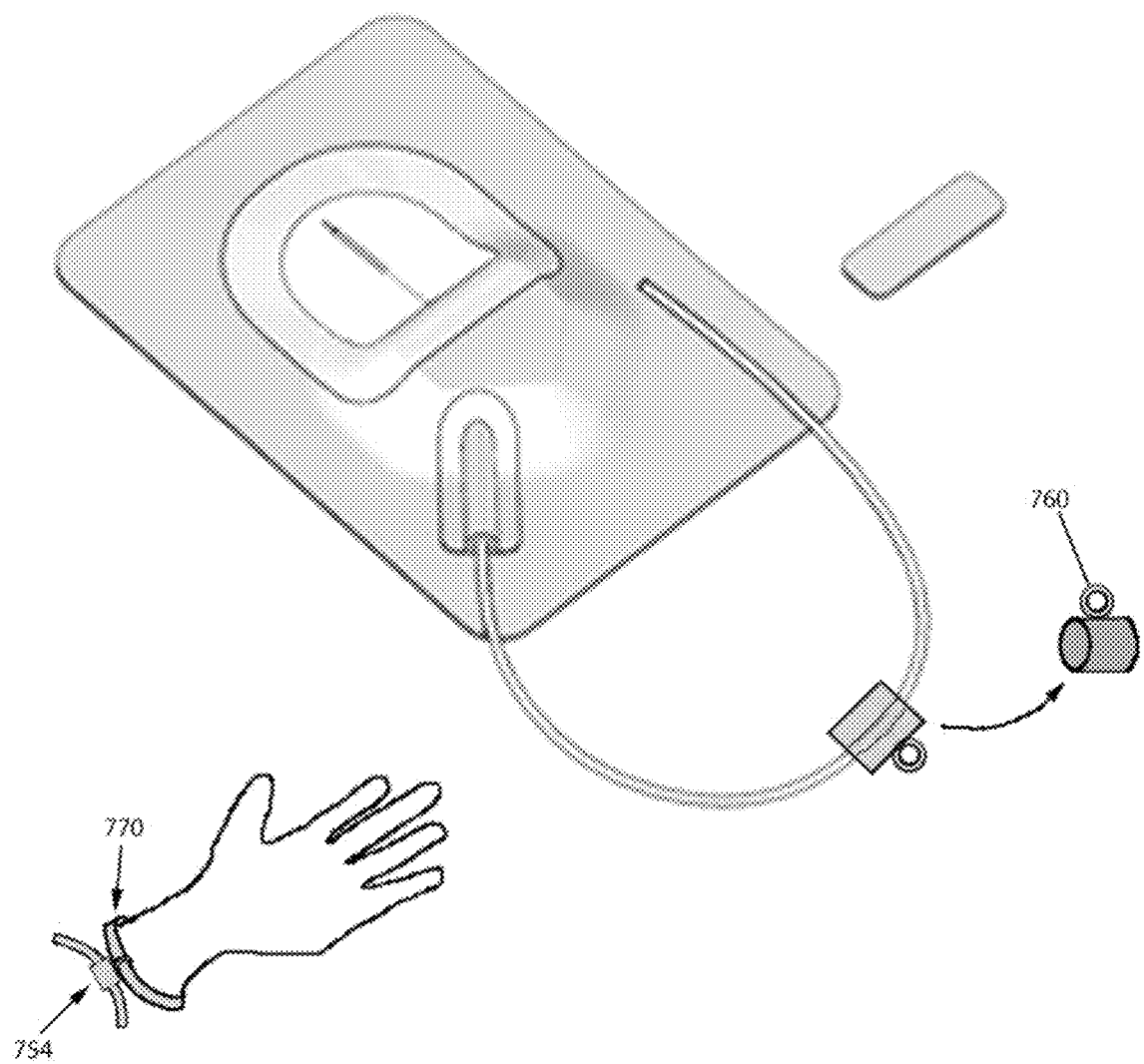
Figure 8:
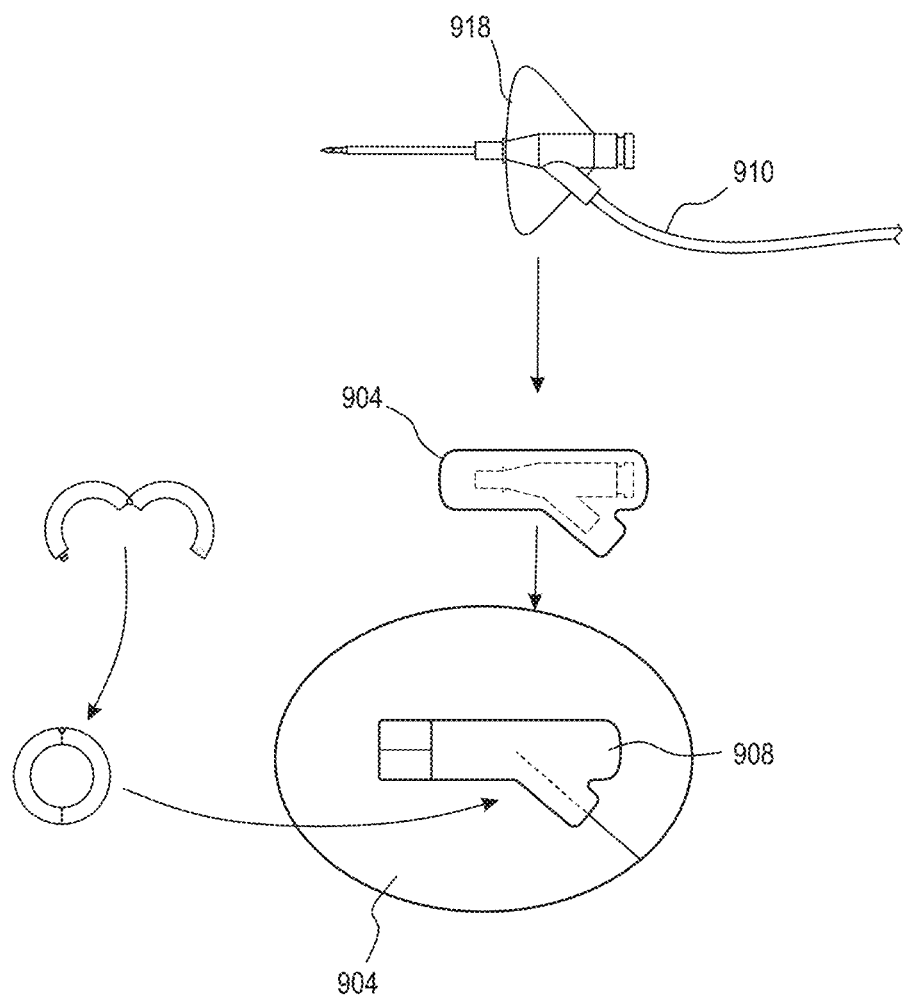
FIG. 8 illustrates another example of sterile dressings according to some embodiments disclosed herein.

FIG. 7E is yet another top perspective view of the dressing 700 according to embodiments disclosed herein. The dressing 700 can include a sliding extension tubing ancillary support collar 760. The sliding extension tubing ancillary support collar 760 can be any suitable attachment mechanism, such as a ring or other attachment mechanism that is directly connected to the sliding collar 760. The sliding collar 760 can be configured to have a length and diameter relative to the tube that requires the sliding collar 760 to be pushed with some force along the tubing to place the sliding collar 760 in position relative to the anchor so that optimal stabilization is achieved. In other words, the sliding collar 760 can be relatively fitted (e.g., be relatively snug) such that specific parallel longitudinal force must be applied with fingers to move the collar 760 along the extension tubing. Acute more perpendicular forces can bind, and therefore stabilize, the collar 760 relative to the tubing. The plastic chosen for this ancillary stabilizing device can be chosen based on its ability to bind with the extension tubing (e.g., PU). FIG. 7E also illustrates an embodiment of the sliding collar anchor point 770. This anchor point 770 take any suitable shape or form available in the art. For example, the anchor point 770 can be a separate piece of adhesive that has a corresponding mating feature, or it can take the form of a wrist or arm bracelet, as illustrated in FIG. 7E.

FIGS. 8 and 9A-9D illustrate other embodiment of the sterile sealing and securing dressing that includes a form fitting (e.g., form fitting to the catheter hub contours) body 908 fused to the underside of the main adhesive plate 904. The side arm portion of this mating body can penetrate the adhesive plate to allow the extension tubing of the catheter 918 to exit the dressing. A slit in the underside of the mating body at the site of the extension tubing 910 can allow the tubing to enter the central channel of the side arm portion of the mating body. A slit in the main dressing adhesive plate adjacent to the slit in the mating body (e.g., a linear continuation of the slit in the mating body) can allow the adhesive plate to be placed past and around the extension tubing as it exits the channel of the side arm. Re-approximation of the slit in the mating body side arm and the adhesive pad can reconstitute a 360 degrees seal. The integrity and durability of this seal can supported by one or more mechanisms including but not limited to: (1) use of a sealing flange support clips 330, and (2) use of one or more mating sliding collar 754 that slides onto the sealing flange of the dressing. The central mating body can take on various forms. For example, the central body can include one to four snap fit clips that clip to specific feature points on a catheter hub, thereby fully attaching the mating body (and its attached dressing) to the catheter (and to the patient once the adhesive plate is adhered to the patient's skin). Alternatively or additionally, a dressing according to the embodiments disclosed herein can include a simple form fit molded central body that form-fits to the catheter hub contour features.

Figure 9A:
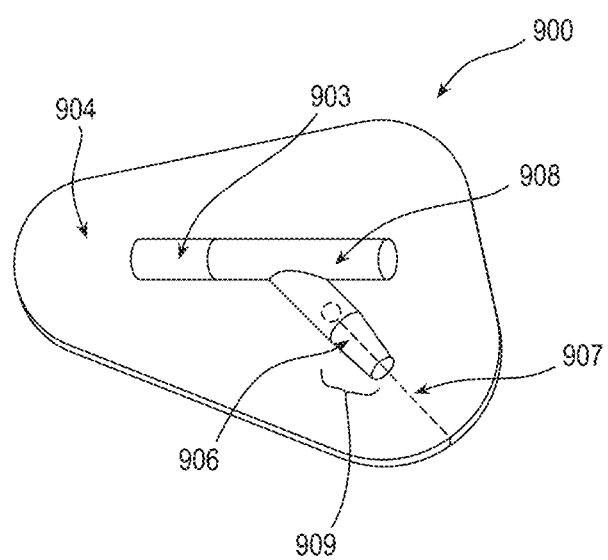
FIGS. 9A-9D illustrate yet another example of sterile dressings according to some embodiments disclosed herein.
Figure 9B:
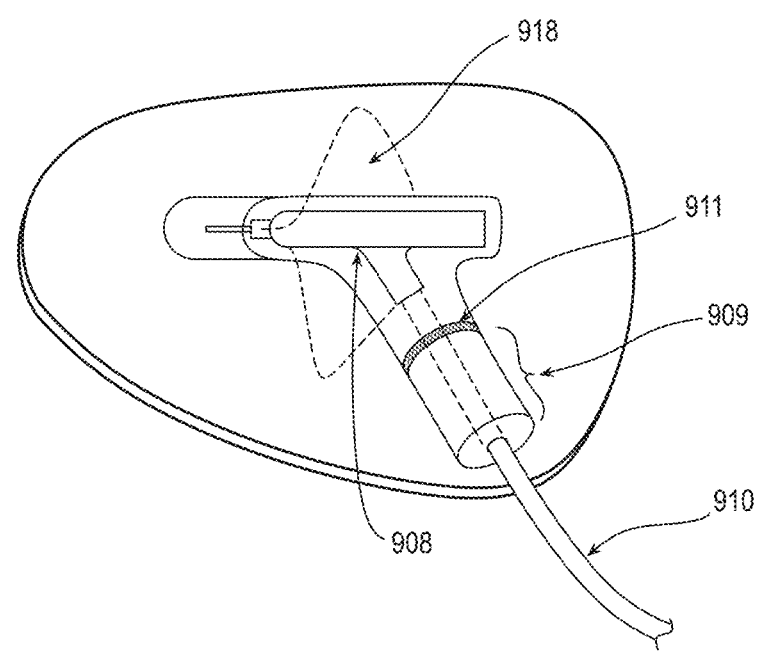
Figure 9C:
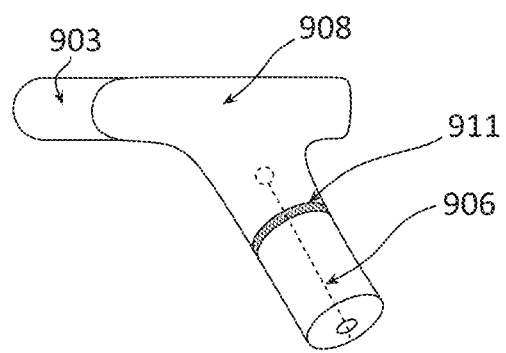
Figure 9D:
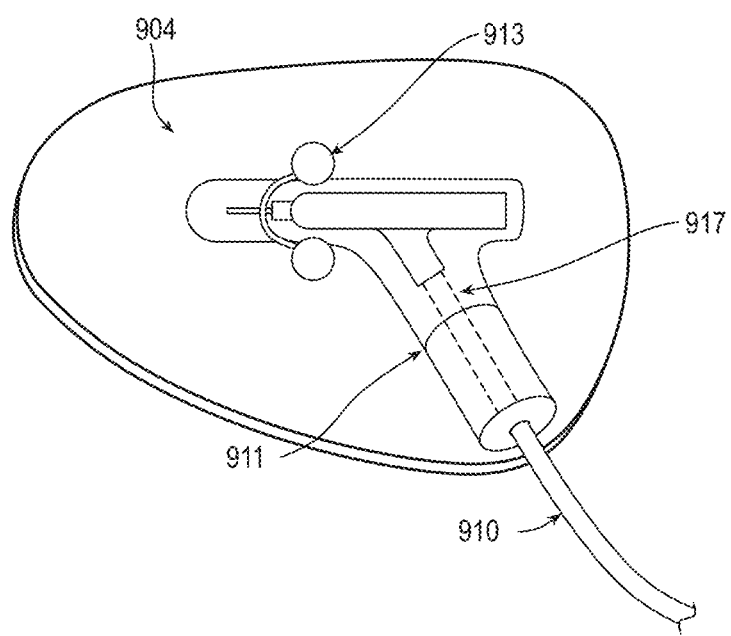

FIGS. 9A-9B illustrate another example of a sterile sealing and securing dressing 900 that can include a flexible or form fitting central mating body 908 fused or otherwise integrated with the main adhesive dressing plate 904. The central mating body 908 can include a splittable seam 906 on a posterior aspect of the extension tubing side arm portion of the central form-fitting body of the dressing. Further, the main adhesive dressing plate 904 can include a split 907 that allows for passing of the extension tubing to the top surface of the adhesive plate. As shown in FIGS. 9A-9B, the dressing 900 can include a transparent insertion site viewing window 903, the extension tubing external circumferential sealing flange 909, and the transition 911 of this sealing flange from the underside 911 to the topside of this dressing, and a catheter in final mating position. FIG. 9C-9D illustrate the detail of the extension tubing support flange portion of the central mating body (circle and slit 906 on the underside in dotted line). FIGS. 9C-9D also illustrate two CHG or other anti-microbial reservoirs 913 that can be activated by finger pressure to emit antimicrobial agent into the sterile sealed viewing chamber. The dressing can also include a circular type opening 917 at the posterior aspect of the central body's sidearm portion that allows the extension tubing to enter the central channel of the circumferential sealing flange. This flange can be a single body that starts beneath the adhesive plate and penetrate the dressing plate to from the anterior surface of the adhesive plate.

Figure 10A:
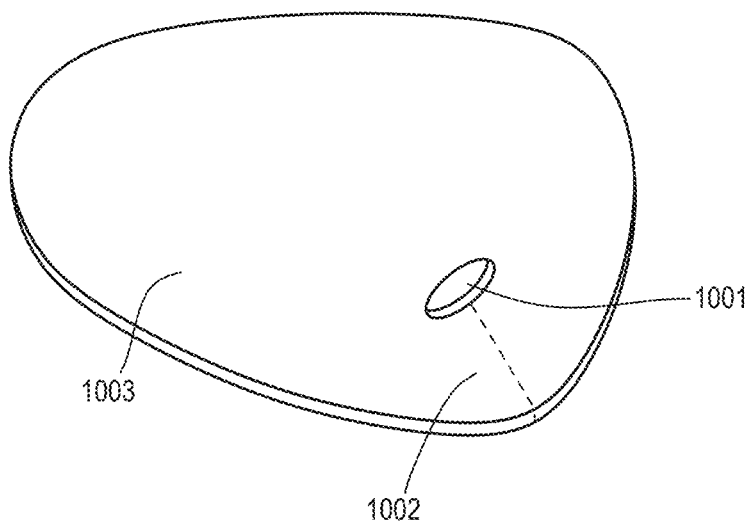
FIGS. 10A-10B illustrate yet an example of an adhesive plate that can be used with a sterile dressing according to some embodiments disclosed herein.
Figure 10B:
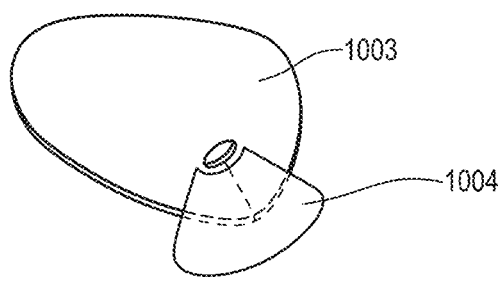
Figure 11:
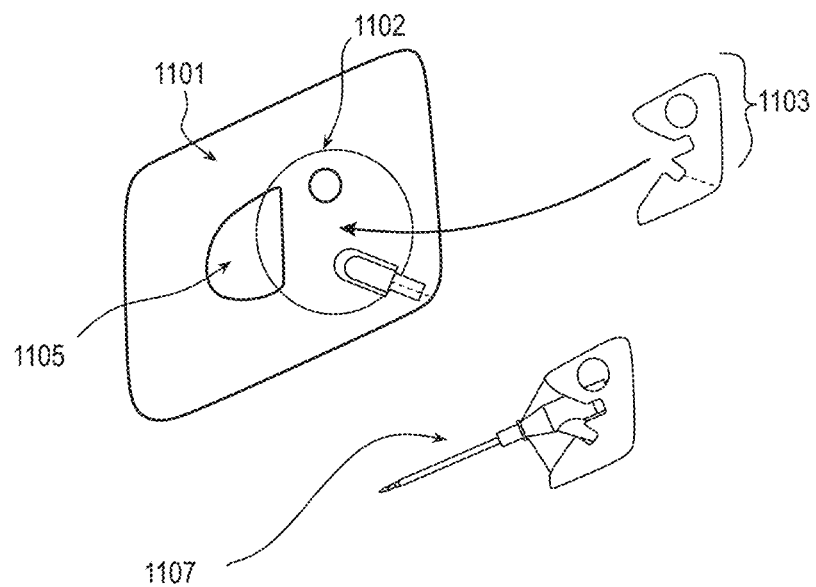

FIGS. 10A-10B illustrate a main adhesive plate 1003 as well as the aperture 1001 through which the central mating body can penetrate form beneath the dressing to on top of the dressing. A slit 1002 in the main adhesive pad can allow a portion of the dressing to pass below the extension tubing as it exits the external flange. The dressing can further include an inset 1004 that can be a specially shaped piece of adhesive pad used to cover, seal, and further support the sealing and securing integrity of the sterile sealing and securing dressing.

Figure 11:
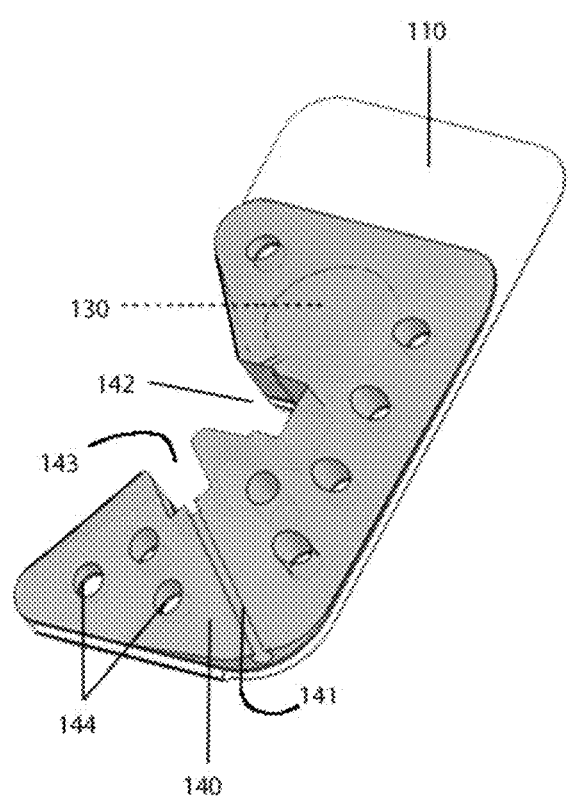
FIG. 11 illustrates another example of sterile dressings according to some embodiments disclosed herein.

FIG. 11 illustrates another example of sterile dressings according to some embodiments disclosed herein. In the example shown in FIG. 11, the dressing comprises of a central mating body 1103 fused to the adhesive plate 1101. The mating body can have a central mating body, having a clear viewing window 1105 that mates with a catheter 1107 by fitting, e.g., to the outline contour of the rear aspect of the catheter. The slit used for the extension tubing can be on the underside of this mating body such that the mating body (with its attached adhesive pad) can be pressed down onto the inserted catheter hub, thereby pushing the extension tubing side arm onto the slot/channel. A slit in the adhesive pad of the dressing can allow the extension tubing to pass to the topside of the dressing. Further, as shown in FIG. 11, the dressing can include a CHG reservoir 1102.

Figure 12:
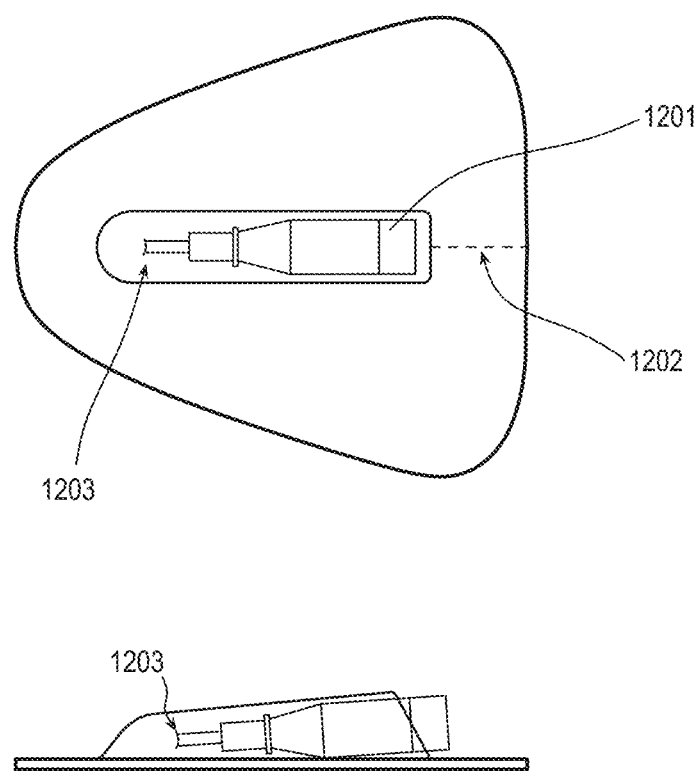
FIG. 12 illustrates another example of sterile dressings according to some embodiments disclosed herein.

FIG. 12 illustrates another example of sterile dressings according to some embodiments disclosed herein. The embodiment shown in FIG. 12 can be viewed as a universal embodiment of the sterile sealing and securing dressing with a viewing window 1203 that can be applied to generally any standard straight peripheral IV catheter 1201. The slit 1202 in the dressing can be seen in the dressing plate. The slit can allow the sealing flange and dressing plate to be passed around the catheter hub into mating and sealing/securing position.

While the preferred embodiments of the invention have been illustrated and described, it will be clear that the invention is not so limited. Numerous modifications, changes, variations, substitutions, and equivalents will occur to those skilled in the art without departing from the spirit and scope of the present invention as defined by the appended claims.

What is claimed is:

1. A dressing for use with an implantable catheter, the dressing comprising:
    a catheter securement plate configured to receive and hold a side-arm catheter, the catheter securement plate having a plate adhesive disposed on at least a portion of its bottom surface to facilitate attachment to skin of a patient at a catheter insertion site;
    a protective sheet for covering the plate adhesive prior to deployment of the catheter securement plate on the skin of the patient; and
    a cover configured for placement over the catheter securement plate to define a sealed chamber at the catheter insertion site, the cover also having a cover adhesive disposed on at least a portion of its bottom surface to contact the catheter securement plate and the skin of the patient to enclose the side-arm catheter;
    wherein the catheter securement plate comprises a top surface that tapers from an area of the plate that is configured to be positioned at the top of a catheter extension tubing of the side-arm catheter to an area of the plate that is configured to be applied to the skin of the patient,
    wherein the catheter securement plate includes a channel within the top surface that is configured to receive and secure a portion of the catheter extension tubing of the side-arm catheter,
    wherein the channel is configured to circumferentially seal around the portion of the catheter extension tubing,
    wherein the catheter securement plate includes a first slot disposed through the catheter securement plate from the top surface to the bottom surface of the catheter securement plate and configured to partially surround a portion of a back-arm of the side-arm catheter allowing the portion of the back-arm to rest on the skin of the patient and to be in contact with the cover, and
    wherein the catheter securement plate includes a second slot disposed through the catheter securement plate from the top surface to the bottom surface and configured to partially surround a portion of a side-arm of the side-arm catheter allowing the portion of the side-arm to rest on the skin of the patient and to be in contact with the cover, the channel extending from a terminating end of the second slot such that at least the portion of the catheter extension tubing is sealed within the channel when the side-arm of the side-arm catheter is disposed within the second slot and the catheter extension tubing is secured to the side-arm.

2. The dressing of claim 1, wherein the securement plate further comprises a recess region spaced laterally from the first slot and configured to receive an antiseptic.

3. The dressing of claim 2, wherein the antiseptic is chlorhexidine, isopropyl alcohol, or a combination thereof.

4. The dressing of claim 1, wherein the plate adhesive comprises a double sided adhesive tape.

5. The dressing of claim 4, wherein the double-sided adhesive tape is a non-woven tape, comprising one or more of silicone and hydrocolloid tape.

6. The dressing of claim 1, wherein the cover further comprises a slit configured to allow a length of the catheter extension tubing to pass through.

7. The dressing of claim 1, wherein the cover is configured to completely cover the catheter securement plate and the skin of the patient surrounding the catheter securement plate.

8. The dressing of claim 1, wherein the cover further comprises at least one window for viewing the catheter insertion site.

9. A catheter dressing, comprising:
a catheter dressing system configured to seal skin of a patient surrounding a side-arm catheter insertion site and to seal around a side-arm catheter extension tubing to prevent contamination of the side-arm catheter insertion site, comprising:
a first layer comprising:
a tube seal and securement member configured to receive and hold a side-arm catheter, the tube seal and securement member having a plate adhesive disposed on at least a portion of a bottom surface of the tube seal and securement member configured to facilitate attachment to the skin of the patient at the side-arm catheter insertion site,
wherein the tube seal and securement member includes a channel configured to receive and secure a portion of the side-arm catheter extension tubing of the side-arm catheter,
wherein the channel is configured to circumferentially seal around the portion of the side-arm catheter extension tubing,
wherein a catheter securement plate includes a top surface including the channel that tapers from the channel to an area that is configured to be applied to the skin of the patient,
wherein the tube seal and securement member includes a first slot disposed through the tube seal and securement member from the top surface to the bottom surface of the tube seal and securement member and configured to partially surround a portion of a back-arm of the side-arm catheter allowing the portion of the back-arm to rest on the skin of the patient and to be in contact with a film, and
wherein the tube seal and securement member includes a second slot disposed through the tube seal and securement member from the top surface to the bottom surface and configured to partially surround a portion of a side-arm of the side-arm catheter allowing the portion of the side-arm to rest on the skin of the patient and to be in contact with the film, the channel extending from a terminating end of the second slot such that at least the portion of the catheter extension tubing is sealed and secured within the channel when the side-arm of the side-arm catheter is disposed within the second slot and the side-arm catheter extension tubing is secured to the side-arm;
a second layer disposed over the first layer, comprising:
the film configured for placement over the tube seal and securement member and a portion of the side-arm catheter to define a sealed chamber at the side-arm catheter insertion site; and
a film adhesive disposed on at least a portion of a bottom surface of the cover and configured to contact the tube seal and securement member, the back-arm and side-arm of the side-arm catheter, and the skin of the patient to enclose the side-arm catheter and the catheter insertion site,
wherein the side-arm catheter extension tubing is partially disposed between the first layer and the second layer.

10. The dressing of claim 9, wherein the tube seal and securement member further comprises a recess region spaced laterally from the first slot and in fluid communication with a third slot, wherein the recess region is configured to receive an antiseptic for release into the sealed chamber through a third slot.

11. The dressing of claim 10, wherein the antiseptic is chlorhexidine, isopropyl alcohol, or a combination thereof.

12. The dressing of claim 9, wherein the plate adhesive comprises a double sided adhesive tape.

13. The dressing of claim 12, wherein the double-sided adhesive tape is a non- woven tape, comprising one or more of silicone and hydrocolloid tape.

14. The dressing of claim 9, wherein the film further comprises a slit configured to allow a length of the catheter extension tubing to pass through.

15. The dressing of claim 9, wherein the film is configured to completely cover the tube seal and securement member and the skin of the patient surrounding the tube seal and securement member.

16. The dressing of claim 9, wherein the film further comprises at least one window for viewing the catheter insertion site.

* * * * *